(12) United States Patent
Brennan et al.

(10) Patent No.: US 10,537,472 B2
(45) Date of Patent: Jan. 21, 2020

(54) OPHTHALMIC SURGICAL SYSTEMS, METHODS, AND DEVICES

(71) Applicant: Alcon Pharmaceuticals Ltd., Fribourg (CH)

(72) Inventors: Jeffrey David Brennan, Los Angeles, CA (US); Mark Humayun, Glendale, CA (US)

(73) Assignee: Alcon Pharmaceuticals Ltd., Fribourg (CH)

( * ) Notice: Subject to any disclaimer, the term of this patent is extended or adjusted under 35 U.S.C. 154(b) by 485 days.

(21) Appl. No.: 14/554,865

(22) Filed: Nov. 26, 2014

(65) Prior Publication Data
US 2015/0148615 A1    May 28, 2015

Related U.S. Application Data

(60) Provisional application No. 61/990,021, filed on May 7, 2014, provisional application No. 61/924,164, filed
(Continued)

(51) Int. Cl.
*A61F 9/007* (2006.01)
*A61B 3/00* (2006.01)
(Continued)

(52) U.S. Cl.
CPC ........ *A61F 9/00736* (2013.01); *A61B 3/0008* (2013.01); *A61B 2017/0003* (2013.01);
(Continued)

(58) Field of Classification Search
CPC ........... A61B 2018/00636; A61B 2018/00654; A61B 2018/00708; A61B 2018/00755;
(Continued)

(56) References Cited

U.S. PATENT DOCUMENTS 3,116,828 A    1/1964    Glassman
3,293,430 A    12/1966    Wustner
(Continued)

FOREIGN PATENT DOCUMENTS

CN    2289530 Y    9/1998
EP    0 876 799    11/1998
(Continued)

OTHER PUBLICATIONS

International Preliminary Report on Patentability and Written Opinion received for International Application No. PCT/US2015/013567, dated Nov. 17, 2016; 17 pages.
(Continued)

*Primary Examiner* — Lynnsy M Summitt

(57) ABSTRACT

The disclosure herein provides ophthalmic surgical systems, methods, and devices. In one embodiment, a handheld medical instrument for surgical procedures comprises a body having an exterior surface shaped to be held and manipulated by a human hand; a surgical tool extending from a distal end of the body; and a pressure-sensitive button for controlling operation of the surgical tool, the pressure-sensitive button comprising an actuation surface positioned adjacent the exterior surface of the body, the pressure-sensitive button further comprising a pressure detection device, the pressure detection device configured to enable output of a signal for controlling a function of the surgical tool, the signal being proportional to a position of the actuation surface.

19 Claims, 30 Drawing Sheets

Related U.S. Application Data on Jan. 6, 2014, provisional application No. 61/910,112, filed on Nov. 28, 2013.

(51) Int. Cl.
*A61F 9/008* (2006.01)
*A61B 17/00* (2006.01)

(52) U.S. Cl.
CPC .............. *A61B 2017/00017* (2013.01); *A61B 2017/00393* (2013.01); *A61F 9/008* (2013.01)

(58) Field of Classification Search
CPC .. A61B 2018/0091; A61B 2018/00916; A61B 2018/00922; A61B 2018/00928; A61B 2018/0094; A61B 2018/00946; A61B 2018/00958; A61B 2018/225; A61B 2017/0003; A61B 2017/00017; A61B 2017/00367; A61F 9/00736; A61F 9/007
See application file for complete search history.

(56) References Cited

U.S. PATENT DOCUMENTS

| | | | |
|---|---|---|---|
| 3,304,609 | A | 2/1967 | Horowitz et al. |
| 3,366,230 | A | 1/1968 | Loran |
| 3,702,940 | A | 11/1972 | Stewart |
| 3,820,656 | A | 6/1974 | Orr |
| 3,884,238 | A | 5/1975 | O'Malley et al. |
| 3,976,195 | A | 8/1976 | Cohen |
| 3,986,263 | A | 10/1976 | Borgelt et al. |
| 4,011,944 | A | 3/1977 | Cooley et al. |
| 4,014,342 | A | 3/1977 | Staub et al. |
| 4,019,514 | A | 4/1977 | Banko |
| 4,108,182 | A | 8/1978 | Hartman et al. |
| 4,112,947 | A | 9/1978 | Nehring |
| 4,117,843 | A | 10/1978 | Banko |
| 4,266,669 | A | 5/1981 | Watson |
| 4,288,733 | A | 9/1981 | Bilanceri et al. |
| 4,293,074 | A | 10/1981 | Dunsky |
| 4,320,761 | A | 3/1982 | Haddad |
| 4,324,243 | A | 4/1982 | Helfgott et al. |
| 4,378,108 | A | 3/1983 | Bailey, Jr. |
| 4,428,748 | A | 1/1984 | Peyman et al. |
| 4,430,062 | A | 2/1984 | Henrichsen et al. |
| 4,479,762 | A | 10/1984 | Bilstad et al. |
| 4,735,610 | A | 4/1988 | Akkas et al. |
| 4,798,580 | A | 1/1989 | DeMeo et al. |
| 4,869,266 | A | 9/1989 | Taylor et al. |
| 4,889,231 | A | 12/1989 | Foote et al. |
| 4,903,710 | A | 2/1990 | Jessamine et al. |
| 4,930,997 | A | 6/1990 | Bennett |
| 4,974,728 | A | 12/1990 | Colton |
| 5,007,535 | A | 4/1991 | Meseke et al. |
| 5,013,240 | A | 5/1991 | Bailey et al. |
| 5,078,677 | A | 1/1992 | Gentelia et al. |
| 5,392,917 | A | 2/1995 | Alpern et al. |
| 5,399,007 | A | 3/1995 | Marconet |
| 5,433,702 | A | 7/1995 | Zelman et al. |
| 5,455,766 | A | 10/1995 | Scheller et al. |
| 5,508,836 | A | 4/1996 | DeCaro et al. |
| 5,554,097 | A | 9/1996 | Guy |
| 5,586,163 | A | 12/1996 | Goldstein |
| 5,627,584 | A | 5/1997 | Nishikori et al. |
| 5,746,719 | A | 5/1998 | Farra et al. |
| 5,779,053 | A | 7/1998 | Partika et al. |
| 5,873,717 | A | 2/1999 | Behringer |
| 5,910,110 | A | 6/1999 | Bastable |
| 5,989,262 | A | 11/1999 | Josephberg |
| 6,022,088 | A | 2/2000 | Metzler |
| 6,024,699 | A | 2/2000 | Surwit et al. |
| 6,037,724 | A * | 3/2000 | Buss .................. A61B 17/1626 310/47 |
| 6,051,011 | A | 4/2000 | Weidenbenner |
| 6,059,792 | A | 5/2000 | Josephberg |
| 6,059,795 | A | 5/2000 | Wallace et al. |
| 6,074,399 | A | 6/2000 | Wallace et al. |
| 6,102,044 | A | 8/2000 | Naidyhorski |
| 6,117,127 | A | 9/2000 | Helmreich et al. |
| 6,158,437 | A | 12/2000 | Vagley |
| 6,185,096 | B1 | 2/2001 | Helot et al. |
| 6,206,014 | B1 | 3/2001 | Cameron, III et al. |
| 6,217,584 | B1 | 4/2001 | Nun |
| 6,251,113 | B1 | 6/2001 | Appelbaum et al. |
| 6,258,111 | B1 | 7/2001 | Ross et al. |
| 6,282,442 | B1 | 8/2001 | Destefano et al. |
| 6,312,258 | B1 | 11/2001 | Ashman |
| 6,355,047 | B1 | 3/2002 | Wallace et al. |
| 6,405,863 | B1 | 6/2002 | Dhindsa |
| 6,428,487 | B1 | 8/2002 | Burdorff |
| 6,508,823 | B1 | 1/2003 | Gonon |
| 6,579,255 | B2 * | 6/2003 | Kadziauskas ....... A61F 9/00745 604/119 |
| 6,616,606 | B1 | 9/2003 | Petersen et al. |
| 6,623,500 | B1 | 9/2003 | Cook et al. |
| 6,641,039 | B2 | 11/2003 | Southard |
| 6,648,223 | B2 | 11/2003 | Boukhny et al. |
| 6,666,875 | B1 | 12/2003 | Sakurai et al. |
| 6,716,219 | B1 | 4/2004 | Koch |
| 6,769,546 | B2 | 8/2004 | Busch |
| 6,896,141 | B2 | 5/2005 | McMichael et al. |
| 6,945,981 | B2 * | 9/2005 | Donofrio ....... A61B 17/320068 604/22 |
| 6,979,328 | B2 * | 12/2005 | Baerveldt ........... A61F 9/00781 606/41 |
| 7,100,771 | B2 | 9/2006 | Massengale et al. |
| 7,114,500 | B2 | 10/2006 | Bonutti |
| 7,165,555 | B2 | 1/2007 | Lee |
| 7,267,246 | B2 | 9/2007 | Eiskant et al. |
| 7,331,463 | B2 | 2/2008 | Hickey |
| 7,362,228 | B2 | 4/2008 | Nycz et al. |
| 7,401,703 | B2 | 7/2008 | McMichael et al. |
| 7,431,157 | B2 | 10/2008 | Porret et al. |
| 7,578,391 | B2 | 8/2009 | Nakamura |
| 7,604,007 | B1 | 10/2009 | Wooley |
| D626,238 | S | 10/2010 | Zinnanti |
| 7,883,465 | B2 | 2/2011 | Donofrio et al. |
| 7,886,743 | B2 | 2/2011 | Cooper et al. |
| 8,002,783 | B2 | 8/2011 | Vercellotti et al. |
| 8,172,834 | B2 | 5/2012 | Bhadri et al. ................. 606/2 |
| 8,177,064 | B2 | 5/2012 | McCormick et al. |
| 8,177,776 | B2 * | 5/2012 | Humayun .............. A61B 90/98 606/1 |
| 8,242,398 | B2 * | 8/2012 | Young ............ A61B 17/320068 200/332.2 |
| 8,323,271 | B2 * | 12/2012 | Humayun ........... A61F 9/00736 606/1 |
| 8,444,629 | B2 | 5/2013 | Manna et al. |
| 8,496,681 | B2 | 7/2013 | Easley |
| 8,525,059 | B2 | 9/2013 | Berger et al. |
| 8,545,440 | B2 * | 10/2013 | Patrick ..................... A61B 8/00 604/131 |
| 8,568,391 | B2 * | 10/2013 | Kerns .................. A61B 50/33 606/1 |
| 8,623,000 | B2 | 1/2014 | Humayun et al. |
| 8,827,945 | B2 * | 9/2014 | Baker ................. A61M 1/0058 604/118 |
| 9,126,270 | B2 | 9/2015 | Nishio et al. |
| 9,138,128 | B2 * | 9/2015 | Teichtmann ....... A61B 1/00025 |
| 9,345,490 | B2 * | 5/2016 | Ippisch ............. A61B 17/1626 |
| 9,393,075 | B2 | 7/2016 | Ghosh |
| 9,526,580 | B2 | 12/2016 | Humayun et al. |
| 9,745,180 | B2 * | 8/2017 | Meijer ..................... B66F 9/12 |
| 9,878,427 | B2 * | 1/2018 | Fuchs .................... B25B 21/00 |
| 2001/0022615 | A1 | 9/2001 | Fernandez et al. |
| 2002/0013517 | A1 | 1/2002 | West et al. |
| 2003/0093503 | A1 | 5/2003 | Yamaki et al. |
| 2003/0159969 | A1 | 8/2003 | McMichael et al. |
| 2003/0165794 | A1 | 9/2003 | Matoba |
| 2003/0178488 | A1 | 9/2003 | Southard |
| 2003/0205233 | A1 | 11/2003 | Aboul-Hosn et al. |
| 2004/0004019 | A1 | 1/2004 | Busch |
| 2004/0116952 | A1 | 6/2004 | Sakurai et al. |

(56) References Cited

U.S. PATENT DOCUMENTS

| | | |
|---|---|---|
| 2004/0138518 A1 | 7/2004 | Rise et al. |
| 2004/0139048 A1 | 7/2004 | Kerr, II et al. |
| 2004/0186683 A1 | 9/2004 | Farber et al. |
| 2004/0208780 A1 | 10/2004 | Faries, Jr. et al. |
| 2004/0243147 A1 | 12/2004 | Lipow |
| 2005/0100719 A1* | 5/2005 | Kanakarajan ......... B32B 15/08 428/209 |
| 2005/0128987 A1 | 6/2005 | Liang |
| 2005/0228326 A1* | 10/2005 | Kalfas ................ A61B 17/7007 602/19 |
| 2005/0245888 A1 | 11/2005 | Cull |
| 2005/0283138 A1 | 12/2005 | Tashiro et al. |
| 2006/0002258 A1 | 1/2006 | Nakamura et al. |
| 2006/0046226 A1 | 3/2006 | Bergler et al. |
| 2006/0086634 A1 | 4/2006 | Steppe |
| 2006/0095066 A1 | 5/2006 | Chang et al. |
| 2006/0100497 A1 | 5/2006 | Sawazaki et al. |
| 2006/0109105 A1 | 5/2006 | Varner et al. |
| 2006/0119481 A1 | 6/2006 | Tethrake et al. |
| 2006/0142739 A1 | 6/2006 | DiSilestro et al. |
| 2006/0235436 A1 | 10/2006 | Anderson et al. |
| 2006/0244593 A1 | 11/2006 | Nycz et al. |
| 2006/0255938 A1 | 11/2006 | Van den Brink |
| 2006/0272979 A1 | 12/2006 | Lubbers et al. |
| 2006/0289016 A1 | 12/2006 | Kammer et al. |
| 2007/0167787 A1* | 7/2007 | Glossop .................. A61B 8/00 600/447 |
| 2007/0282353 A1 | 12/2007 | Surti et al. |
| 2007/0290654 A1 | 12/2007 | Govari et al. |
| 2008/0004608 A1 | 1/2008 | Dacquay et al. ............... 606/4 |
| 2008/0030345 A1 | 2/2008 | Austin et al. |
| 2008/0041282 A1 | 2/2008 | Goschy et al. |
| 2008/0077123 A1 | 3/2008 | Boyden et al. |
| 2008/0077145 A1* | 3/2008 | Boyden ............. A61B 17/3201 606/79 |
| 2008/0120137 A1 | 5/2008 | Nyholm |
| 2008/0125761 A1 | 5/2008 | Weston et al. |
| 2008/0167644 A1 | 7/2008 | Shelton et al. |
| 2008/0208233 A1 | 8/2008 | Barnes et al. |
| 2008/0272023 A1 | 11/2008 | McCormick et al. |
| 2008/0281301 A1 | 11/2008 | DeBoer et al. |
| 2008/0308698 A1 | 12/2008 | Steppe |
| 2009/0163897 A1 | 6/2009 | Skinner .................. 606/4 |
| 2009/0313773 A1 | 12/2009 | Filsouf |
| 2010/0069825 A1* | 3/2010 | Raney ............ A61B 17/320068 604/22 |
| 2010/0134303 A1 | 6/2010 | Perkins |
| 2010/0174415 A1 | 7/2010 | Humayun et al. |
| 2010/0258414 A1 | 10/2010 | Young et al. |
| 2011/0105999 A1 | 5/2011 | Akahoshi ..................... 604/22 |
| 2011/0112518 A1 | 5/2011 | Stanton |
| 2011/0130632 A1* | 6/2011 | McGrail ............ A61B 1/00016 600/188 |
| 2011/0144567 A1 | 6/2011 | Sorensen et al. |
| 2011/0203821 A1* | 8/2011 | Puzio ................. B25B 23/0064 173/1 |
| 2011/0257481 A1 | 10/2011 | Ogawa et al. |
| 2011/0276340 A1 | 11/2011 | DeBoer et al. |
| 2011/0295193 A1 | 12/2011 | Fitzgerald et al. |
| 2012/0022510 A1* | 1/2012 | Welches ................ A61B 18/22 606/3 |
| 2012/0232540 A1 | 9/2012 | Baur et al. |
| 2013/0009606 A1 | 1/2013 | Smith et al. |
| 2014/0238890 A1 | 8/2014 | Kerns et al. |
| 2014/0271251 A1* | 9/2014 | Bourne ................... F04B 43/12 417/53 |
| 2014/0271273 A1* | 9/2014 | Carpenter ........... A61M 1/0064 417/412 |
| 2014/0323813 A1 | 10/2014 | Humayun et al. |
| 2014/0365235 A1 | 12/2014 | DeBoer et al. |
| 2014/0378952 A1 | 12/2014 | Humayun et al. |
| 2015/0144514 A1 | 5/2015 | Brennan et al. |
| 2015/0238264 A1 | 8/2015 | Kerns et al. |

FOREIGN PATENT DOCUMENTS

| | | |
|---|---|---|
| EP | 1 236 439 | 9/2002 |
| EP | 1 813 199 | 8/2007 |
| EP | 2 441 393 | 4/2012 |
| JP | 05-044111 U | 6/1993 |
| JP | 2004-250108 | 6/1993 |
| JP | 3 310 360 | 5/2002 |
| JP | 2002-515293 | 5/2002 |
| JP | 2002/233534 | 8/2002 |
| JP | 3 088 841 | 10/2002 |
| JP | 2002/345839 | 12/2002 |
| JP | 2005-046412 | 2/2005 |
| JP | 2006-511285 | 4/2006 |
| JP | 2007-501055 | 1/2007 |
| JP | 2007167644 A | 7/2007 |
| JP | 2009-219718 | 10/2009 |
| JP | 2010-503513 | 2/2010 |
| JP | 2011/045961 | 3/2011 |
| JP | 2011516120 A | 5/2011 |
| JP | 2012/223243 | 11/2012 |
| JP | 2013516287 A | 5/2013 |
| WO | WO 92/20310 | 11/1992 |
| WO | WO 95/01135 | 1/1995 |
| WO | WO 98/06338 | 2/1998 |
| WO | WO 99/59510 | 11/1999 |
| WO | WO 99/66444 | 12/1999 |
| WO | WO 2000/32115 | 6/2000 |
| WO | WO 01/12098 | 2/2001 |
| WO | WO 02/083021 | 10/2002 |
| WO | WO 03/034213 | 4/2003 |
| WO | WO 2004/060184 | 7/2004 |
| WO | WO 2004/105631 | 12/2004 |
| WO | WO 2005/016183 | 2/2005 |
| WO | WO 2008/036453 | 3/2008 |
| WO | WO 2008/131357 | 10/2008 |
| WO | WO 2008/152378 | 12/2008 |
| WO | WO 2010/030850 | 3/2010 |
| WO | 2012/151062 | 11/2012 |
| WO | 2014/025702 | 2/2014 |

OTHER PUBLICATIONS

International Preliminary Report on Patentability and Written Opinion reeived for International Application No. PCT/US2014/067717, dated Jun. 9, 2016; 11 pages.

Extended European Search Report, dated Nov. 23, 2010, in European Patent Application No. 08746468.1.

International Preliminary Report on Patentability and Written Opinion, dated Apr. 26, 2011, in PCT Application No. PCT/US2008/080832.

International Preliminary Report on Patentability and Written Opinion, dated Oct. 20, 2009, in PCT Application No. PCT/US2008/061058.

International Preliminary Report on Patentability, dated Jan. 10, 2012, in PCT Application No. PCT/US2011/20415.

International Preliminary Report on Patentability, dated Nov. 5, 2013, in PCT Application No. PCT/US2012/034480.

International Search Report and Written Opinion, dated Sep. 2, 2008, in PCT Application No. PCT/US2008/061043.

International Search Report and Written Opinion, dated Aug. 27, 2008, in PCT Application No. PCT/US2008/061058.

International Search Report and Written Opinion, dated Dec. 22, 2008, in PCT Application No. PCT/US2008/061065.

International Search Report and Written Opinion, dated Jul. 29, 2010, in PCT Application No. PCT/US2008/080832.

International Search Report and Written Opinion, dated Jun. 2, 2011, in PCT Application No. PCT/US2011/020415.

International Search Report and Written Opinion, dated Oct. 18, 2012, in PCT Application No. PCT/US2012/034480.

International Search Report and Written Opinion, dated Mar. 5, 2015, in PCT Application No. PCT/US2014/067717.

International Search Report and Written Opinion, dated May 20, 2015, in PCT Application No. PCT/US2015/013567.

(56) References Cited

OTHER PUBLICATIONS

Merriam-Webster.com definition of "tray"; http://www.merriam-webster.com/dictionary/tray.
Partial International Search Report, dated Apr. 27, 2010, in PCT Application No. PCT/US2008/080832.
Partial International Search Report, dated Jul. 6, 2012, in PCT Application No. PCT/US2012/034480.
Supplementary European Search Reported, dated Dec. 10, 2010, in European Patent Application No. 08746468.1.
Extended European Search Report for European Patent Application No. 14866168.9, dated Apr. 7, 2017; 6 pages.
Partial Supplementary European Search Report for European Patent Application No. 15789716.6, dated Jan. 3, 2018; 12 pages.
Office Action for Japanese Patent Application No. 2016-534948, dated Aug. 7, 2018, no English translation; 3 pages.
Office Action received for Australian Patent Application No. 2014354716, dated Jul. 25, 2018; 4 pages.
Office Action received for Australian Patent Application No. 2014354716, dated Aug. 1, 2018; 4 pages.

\* cited by examiner

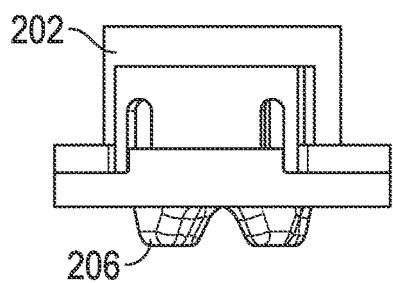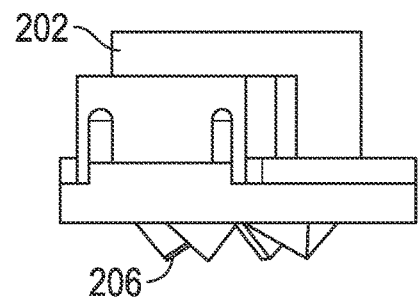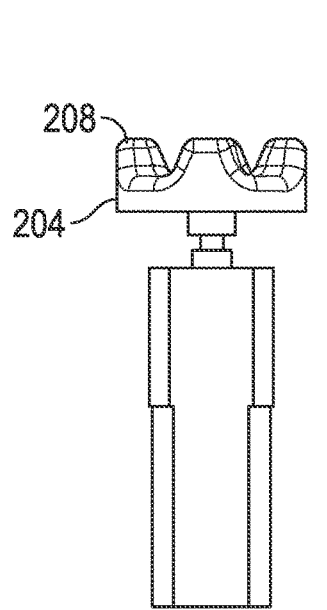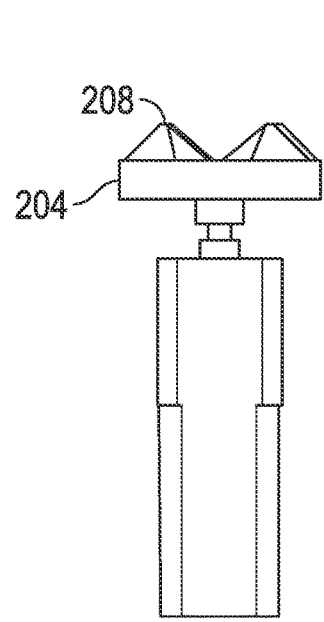
FIG. 2J     FIG. 2K

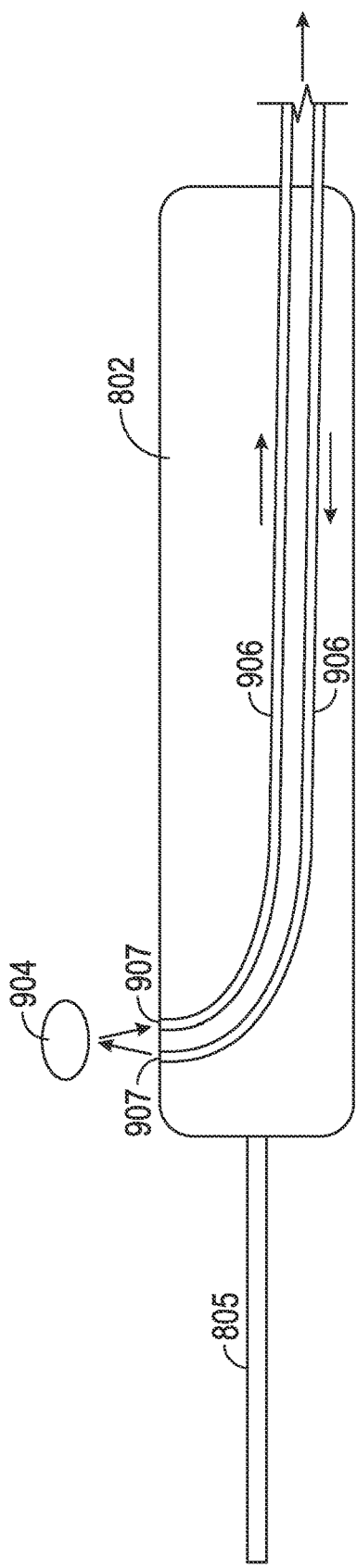
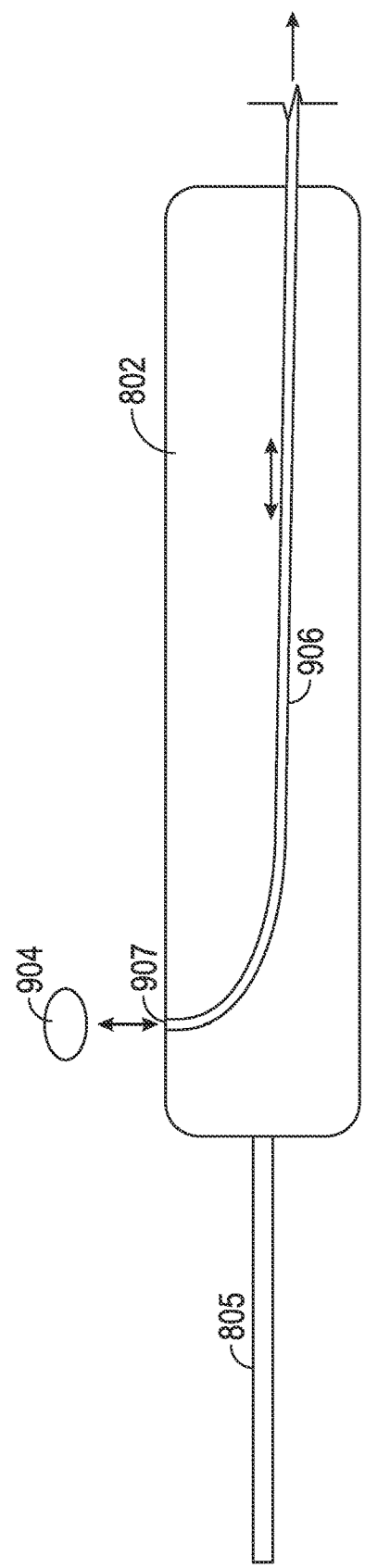
FIG. 9A
FIG. 9B

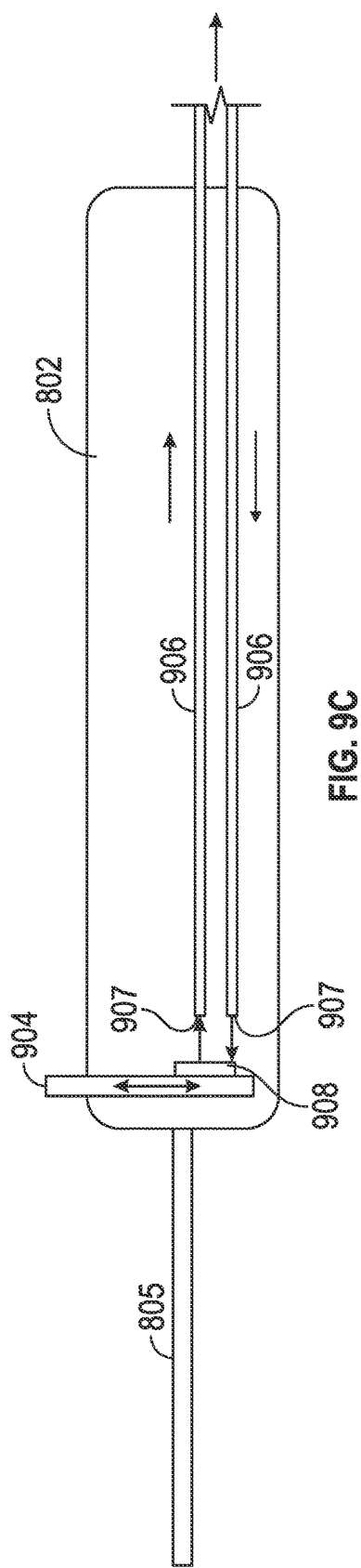
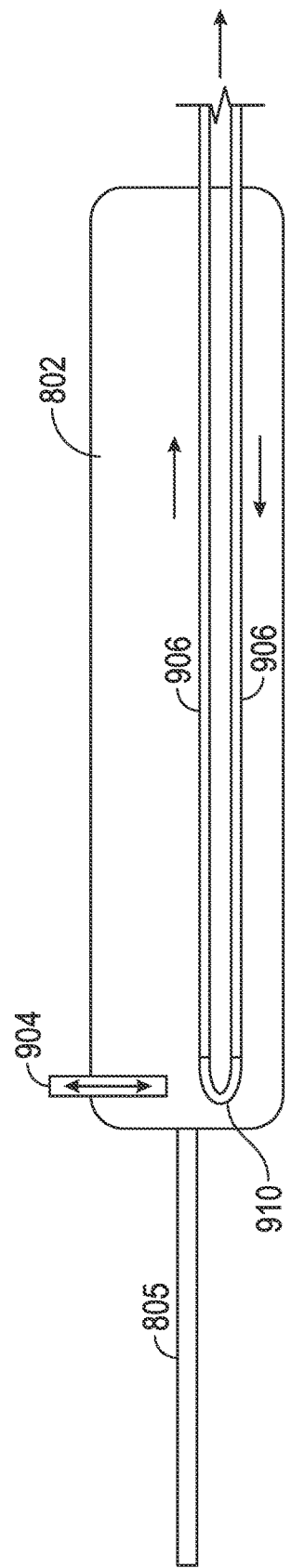

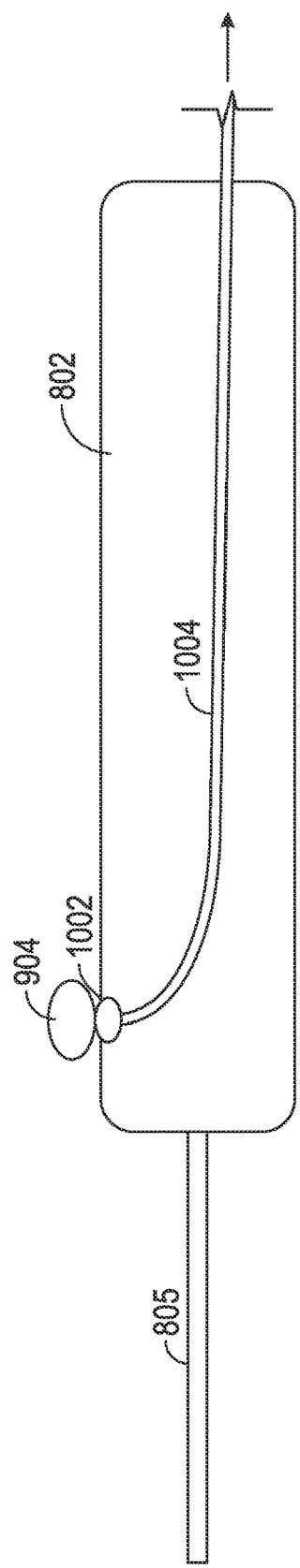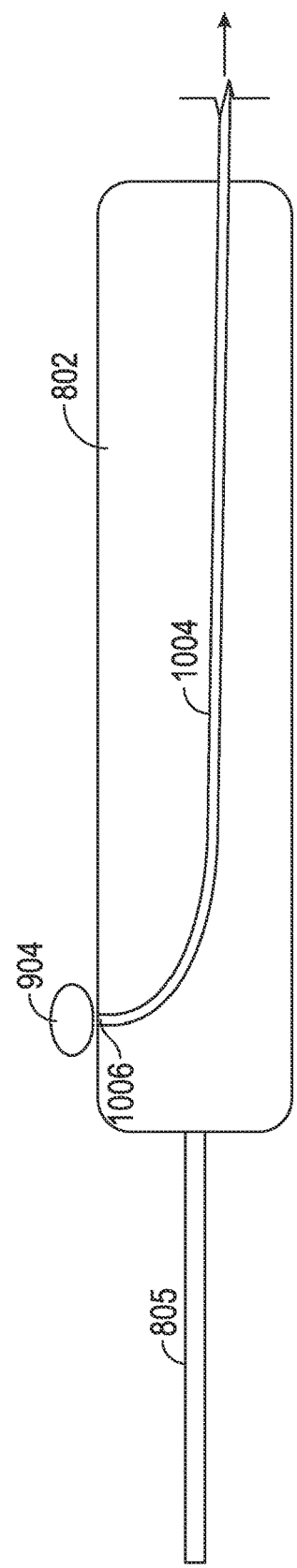

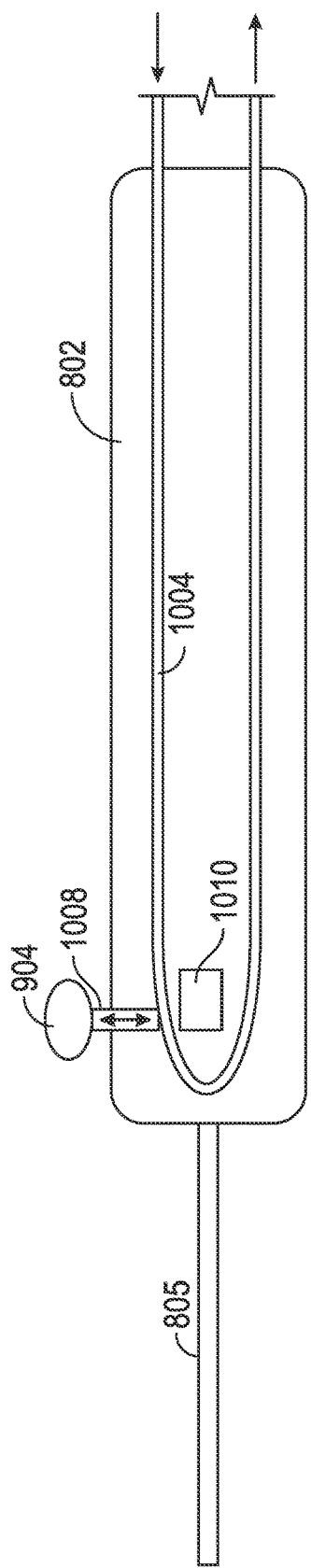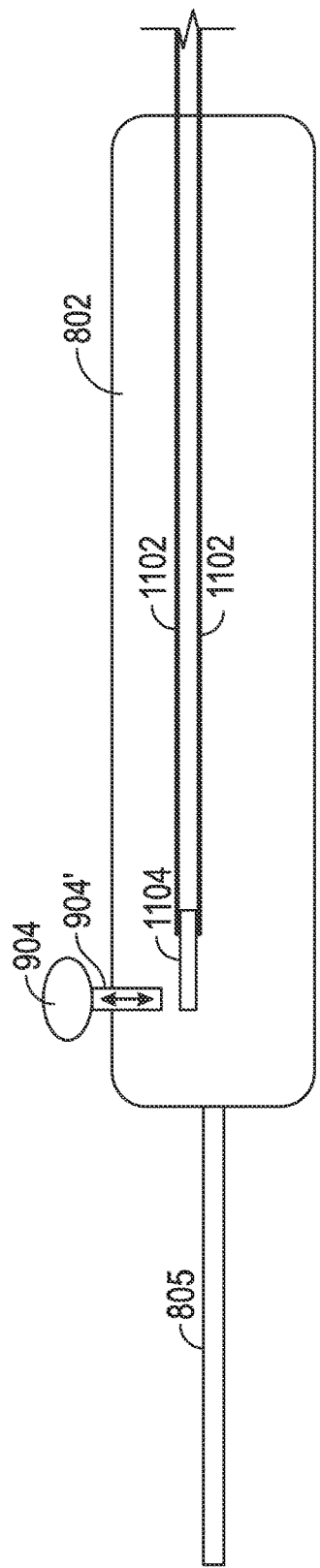

OPHTHALMIC SURGICAL SYSTEMS, METHODS, AND DEVICES

CROSS-REFERENCE TO RELATED APPLICATIONS

This application claims the benefit of U.S. Provisional Application No. 61/990,021, titled OPHTHALMIC SURGICAL SYSTEMS, filed May 7, 2014, and of U.S. Provisional Application No. 61/924,164, titled OPHTHALMIC SURGICAL SYSTEMS, filed Jan. 6, 2014, and of U.S. Provisional Application No. 61/910,112, titled OPHTHALMIC SURGICAL SYSTEMS, filed Nov. 28, 2013. Each of the foregoing applications is hereby incorporated by reference herein in its entirety.

BACKGROUND

Field

The disclosure relates generally to the field of ophthalmic surgery, and more specifically to ophthalmic surgical systems, methods, and devices.

Description

The field of ophthalmology has become increasingly important in today's society as adults are living longer and older generations comprise a growing proportion of the world population. Vision care and the treatment of ocular diseases or conditions have benefited in recent years from advancements in both pharmacology and medical device technologies. Microsurgical instruments and innovative surgical techniques enable surgeons to repair or replace parts of the eye previously considered inaccessible and off-limits. In particular, console systems that provide a variety of functions dedicated to a specific set of procedures (such as vitrectomy or cataract removal procedures) are now available to surgeons, with improvements and updates to the technology occurring on a regular basis. Often times these consoles are very expensive, requiring a large capital expenditure by a surgeon, hospital, or ambulatory surgical center. They also often have high recurring costs for the single-use disposable elements of the system, and may have high maintenance costs as well. The consoles often incorporate a lot of unnecessary or infrequently used functionality in order to differentiate from competing products. Hence, in addition to being costly, the consoles are often large, heavy, bulky, noisy, power-hungry, and bloated machines that contrast sharply with the small, delicate eye they are designed to treat. Furthermore, the drawbacks of these systems often require them to be located some distance from the surgeon, resulting in long tubing sets and/or cables that negatively impact the performance of the system while increasing the cost. Hence, there is a need for smaller, more portable, more self-contained, and more cost-effective systems that incorporate the major functions required to perform certain procedures.

SUMMARY

The disclosure herein provides ophthalmic surgical systems, methods, and devices. In some embodiments, a handheld surgical instrument comprises a pressure sensitive button for controlling a surgical function. In some embodiments, the pressure sensitive button is positioned circumferentially around a body of the surgical tool, such that external pressure applied to the button at any or substantially any location around the circumference (or at any location within a predefined range, such as, for example, about 350, 325, 300, 275, 250, 225, 200, or 180 degrees of the full circumference) is detectable by the pressure sensitive button. In some embodiments, a handheld surgical instrument comprises a nonelectric button, such as, for example, a pneumatic, hydraulic, optical, and/or the like button. In some embodiments, an ophthalmic surgical system is configured to utilize a reusable base and a disposable sterile surgical tray coupled thereto. In some embodiments, some functions are contained within or coupled to the disposable tray, such as, for example, fluidics and/or handpieces; and reusable components, such as, for example, a power source (for example, electrical, mechanical, hydraulic, pneumatic, optical, and/or the like) for the handpieces located in the reusable base. In some embodiments, a custom surgical drape is provided which comprises one or more functional interfaces enabling a function to pass therethrough. In some embodiments, the function configured to pass therethrough may comprise an electrical current, light, pneumatic or fluidic coupling, and/or a mechanical coupling or other feature. In some embodiments, an ophthalmic surgical system is configured to be automatically updated or configured in response to detection of a tag, such as an RFID tag, a near field communication device, a memory card/USB, or other storage device, and/or the like.

According to some embodiments, a handheld medical instrument for surgical procedures comprises: a body having an exterior surface shaped to be held and manipulated by a human hand; a surgical tool extending from a distal end of the body; and a pressure-sensitive button for controlling operation of the surgical tool, the pressure-sensitive button comprising an actuation surface positioned adjacent the exterior surface of the body, the pressure-sensitive button further comprising a pressure detection device, the pressure detection device configured to enable output of a signal for controlling a function of the surgical tool, the signal being proportional to a position of the actuation surface.

In some embodiments, the pressure detection device comprises a force sensitive resistor that changes a resistance based on the position of the actuation surface. In some embodiments, the actuation surface extends circumferentially around an exterior of the body and is positioned at least partially around a conductive surface of the force sensitive resistor. In some embodiments, the pressure detection device comprises an optical fiber positioned such that movement of the actuation surface with respect to the body causes the optical fiber to deform. In some embodiments, the pressure detection device comprises an optical fiber and an optical detection member, wherein movement of the actuation surface with respect to the body causes the optical detection member to move in a way that affects a light signal of the optical fiber. In some embodiments, the pressure detection device comprises a deformable member coupled to the actuation surface such that movement of the actuation surface with respect to the body deforms the deformable member, causing a change in pressure within the deformable member. In some embodiments, the pressure detection device comprises a piezoelectric material coupled to the actuation surface such that movement of the actuation surface with respect to the body causes deformation of the piezoelectric material. In some embodiments, the surgical tool comprises at least one of: an aspiration device, an endoillumination device, a laser therapy device, a lens removal device, a trabecular meshwork removal device, and a vitreous cutting device. In some embodiments, the controlled function of the surgical tool comprises at least one of: a speed and an intensity. For example, the controlled function can be configured to be controlling the intensity of infusion pressure or aspiration vacuum. In some embodiments, the proportionality of the signal in relation to the position of the actuation surface is linear. The term "linear" as used herein is a broad term, and unless otherwise indicated, the term can include within its meanings, without limitation, a reference to the concept of a variable output that is proportional to some input (for example, the applied force or deflection), but in some embodiments, the term "linear" can refer to a response that is not necessarily a linearly proportional response and can include a non-linear response (for example, logarithmic or exponential response based on a linear input), and in some embodiments, the term "linear" can refer to a response that is a combination of a linear and non-linear response (for example, the initial range of an input produces an initial response that is linear and a second range of the input produces a response that is non-linear). In some embodiments, the actuation surface is movable between a fully outward position and a fully depressed position, wherein the actuation surface is biased outward, such that the actuation surface remains in the fully outward position until an external force is applied that overcomes a biasing force. In some embodiments, the signal is configured to control simultaneously the function of the surgical tool and at least one other surgical function. In some embodiments, the handheld medical instrument further comprises a second pressure-sensitive button comprising a second actuation surface and second pressure detection device configured to enable controlling of a second surgical function. In some embodiments, the handheld medical instrument further comprises a tether coupled to a surgical tray. In some embodiments, the pressure detection device is configured to transmit the signal to a processor external to the medical instrument for interpretation of the signal for controlling of the function of the surgical tool. In some embodiments, the signal controls the function of the surgical tool without the signal being transmitted to a processor external to the medical instrument for interpretation. In some embodiments, the body comprises at least one of the following: an elongate cylindrical shape and an elongate rounded shape.

According to some embodiments, a handheld medical instrument for surgical procedures comprises: a body having an exterior surface shaped to be held and manipulated by a human hand; a surgical tool extending from a distal end of the body; a button for controlling operation of the surgical tool, the button positioned adjacent the exterior surface of the body, wherein the button comprises a non-electrical detection mechanism; and a signal transfer conduit configured to enable output of a signal from the non-electrical detection mechanism for controlling a function of the surgical tool.

In some embodiments, the signal transfer conduit comprises an optical fiber, and the detection mechanism comprises an end surface of the optical fiber. In some embodiments, the signal transfer conduit comprises an optical fiber, and the detection mechanism comprises an optical detection member, wherein movement of the optical detection member with respect to the body affects a light signal of the optical fiber. In some embodiments, the signal transfer conduit comprises an optical fiber, and the detection mechanism comprises a portion of the optical fiber that is deformable by movement of an actuation surface with respect to the body. In some embodiments, the signal transfer conduit comprises one of a pneumatic and a hydraulic tube, and the detection mechanism comprises an opening of the tube or an opening fluidly coupled to the tube, the opening positioned adjacent the exterior surface of the body. In some embodiments, the signal transfer conduit comprises one of a pneumatic and a hydraulic tube, and the detection mechanism comprises an actuation surface movably coupled to the body, wherein movement of the actuation surface with respect to the body causes to deform one of a portion of the tube and a deformable member fluidly coupled to the tube. In some embodiments, the surgical tool comprises at least one of: an aspiration device, an endoillumination device, a laser therapy device, a lens removal device, a trabecular meshwork removal device, and a vitreous cutting device. In some embodiments, the controlled function of the surgical tool comprises at least one of: a speed and an intensity. In some embodiments, the handheld medical instrument further comprises a tether coupled to a surgical tray. In some embodiments, the pressure detection device is configured to transmit the signal to a processor external to the medical instrument for interpretation of the signal for controlling of the function of the surgical tool. In some embodiments, the body comprises at least one of the following: an elongate cylindrical shape and an elongate rounded shape.

According to some embodiments, a surgical drape for use in a sterile operating field comprises: a flexible sheet sized to be at least partially sandwiched between first and second surgical devices and to at least partially cover the second surgical device to maintain a sterile barrier between the first and second surgical devices; and at least one access interface integrally formed or coupled to the flexible sheet, wherein the access interface is configured to enable at least one of the following to pass therethrough while maintaining the sterile barrier: electrical current, light, a mechanical coupling, an optical coupling, a fluid coupling, and a pneumatic coupling.

In some embodiments, the access interface is positionable at an electrical interface of the first and second surgical devices, and the access interface comprises electrical contacts configured to enable electrical current to pass therethrough. In some embodiments, the access interface is positionable at an electrical interface of the first and second surgical devices, and the access interface comprises an anisotropically conductive material. In some embodiments, the access interface comprises an optically-transparent window. In some embodiments, the access interface comprises a perforated region. In some embodiments, the functional interface comprises a sealing feature that forms a seal around the perforated region. In some embodiments, the access interface comprises a region to be punctured. In some embodiments, the functional interface comprises a sealing feature that forms a seal around the punctured region. In some embodiments, the second surgical device comprises a reusable base, and the first surgical device comprises a sterile surgical tray configured to be releasably coupled to the base, wherein the flexible sheet is form-fitted to the reusable base.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects, and advantages of the present invention are described in detail below with reference to the drawings of various embodiments, which are intended to illustrate and not to limit the invention. The drawings comprise the following figures in which:

FIGS. 2A-2K illustrate a variety of embodiments of coupling mechanisms.

FIGS. 9A-9D illustrate example embodiments of handpieces comprising one or more optical buttons.

FIGS. 10A-10C illustrate example embodiments of handpieces comprising pneumatic or hydraulic buttons.

FIG. 11 illustrates an embodiment of a handpiece comprising a piezoelectric button.

DETAILED DESCRIPTION OF THE EMBODIMENTS

Although several embodiments, examples, and illustrations are disclosed below, it will be understood by those of ordinary skill in the art that the invention described herein extends beyond the specifically disclosed embodiments, examples, and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

Surgical Tray Console

Some embodiments comprise a surgical tray or console that is located adjacent to the surgical site or nearby (e.g. adjacent to or around the patient's head during eye surgery). The tray may be U-shaped, L-shaped, or otherwise curved or angled to accommodate the anatomy of the surgical site. Some embodiments comprise a surgical tray that is mounted, secured, or otherwise attached to the patient gurney, patient headrest, surgeon's armrest, or surgical microscope through a temporary, semi-permanent, or permanent means. Some embodiments comprise a separate permanent or semi-permanent base unit that is securely mounted to the gurney, armrest, or other fixture such that the tray can be securely seated or positioned on the base. In some embodiments, the base replaces the surgeon's armrest or is mounted to the armrest and is therefore designed with the strength to support the surgeon's arms and hands. In other embodiments, the tray itself mounts directly to the fixture (armrest, gurney, microscope, etc.), for example using clips, straps, clamps, or other features to enable a secure mounting.

FIGS. 1A-1F illustrate an embodiment of a surgical tray 10 that may be used for an ophthalmic surgical procedure.

Figure 1A:
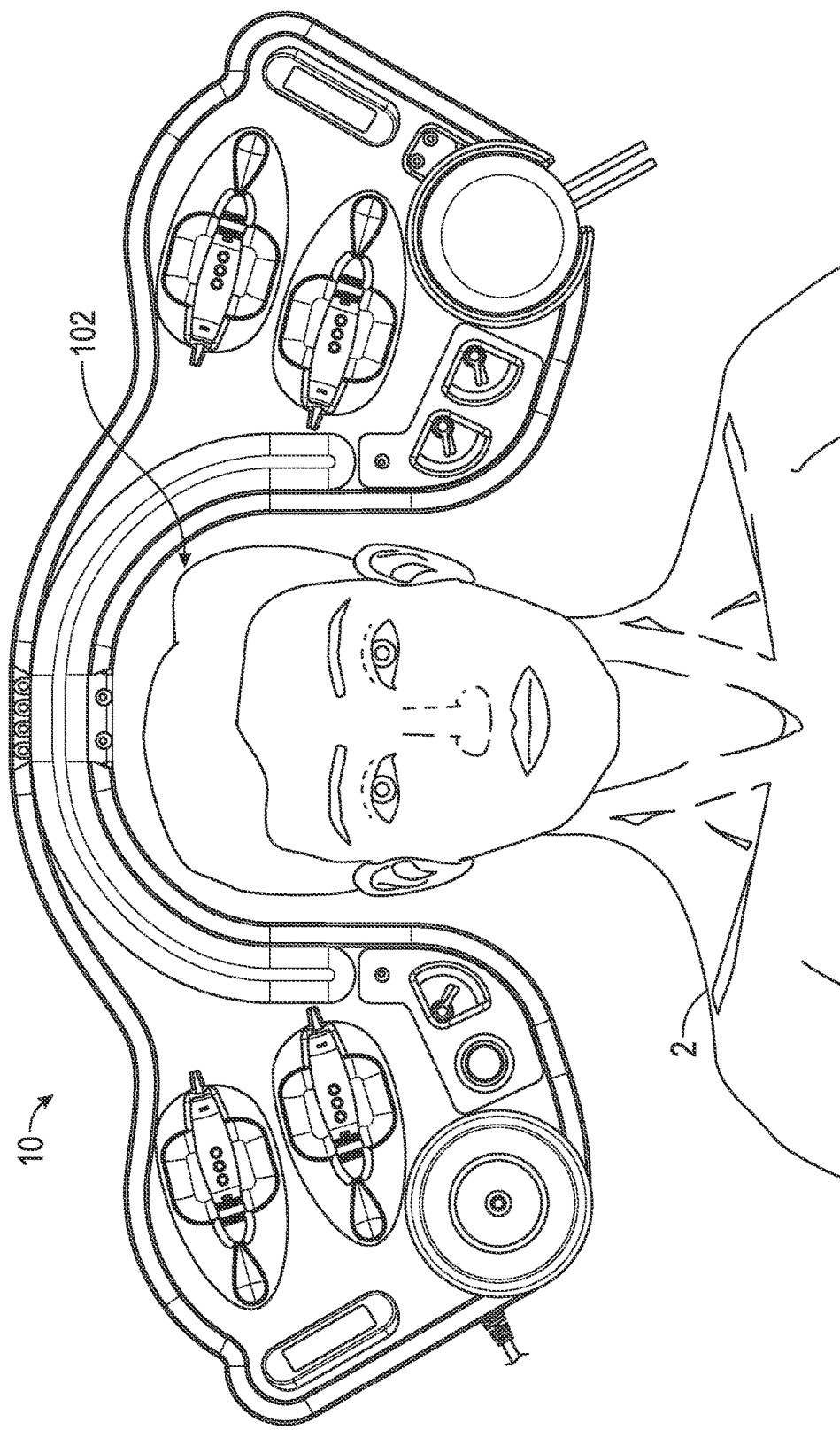
FIGS. 1A-1F illustrate an embodiment of a surgical tray that may be used for an ophthalmic surgical procedure.
Figure 1C:
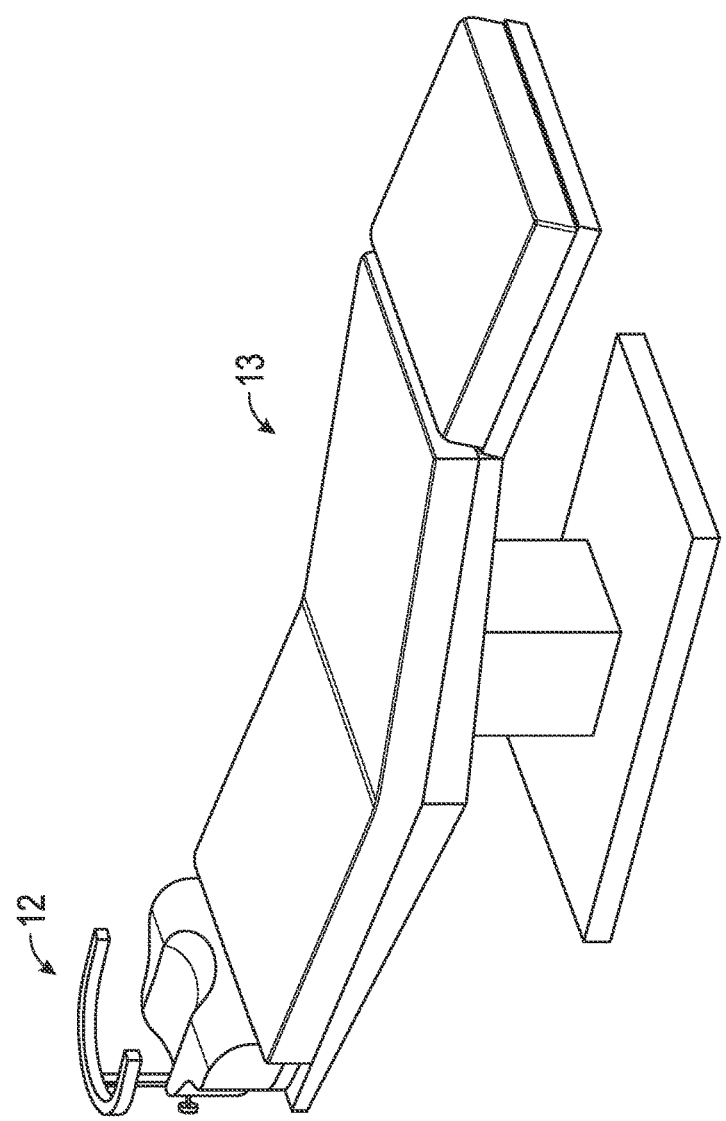
Figure 1B:
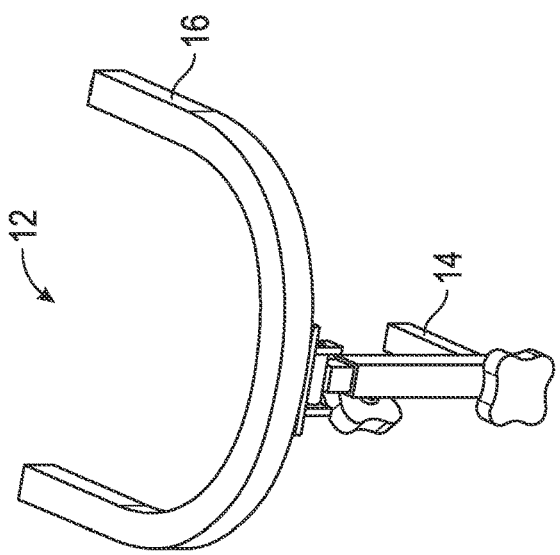
Figure 1D:
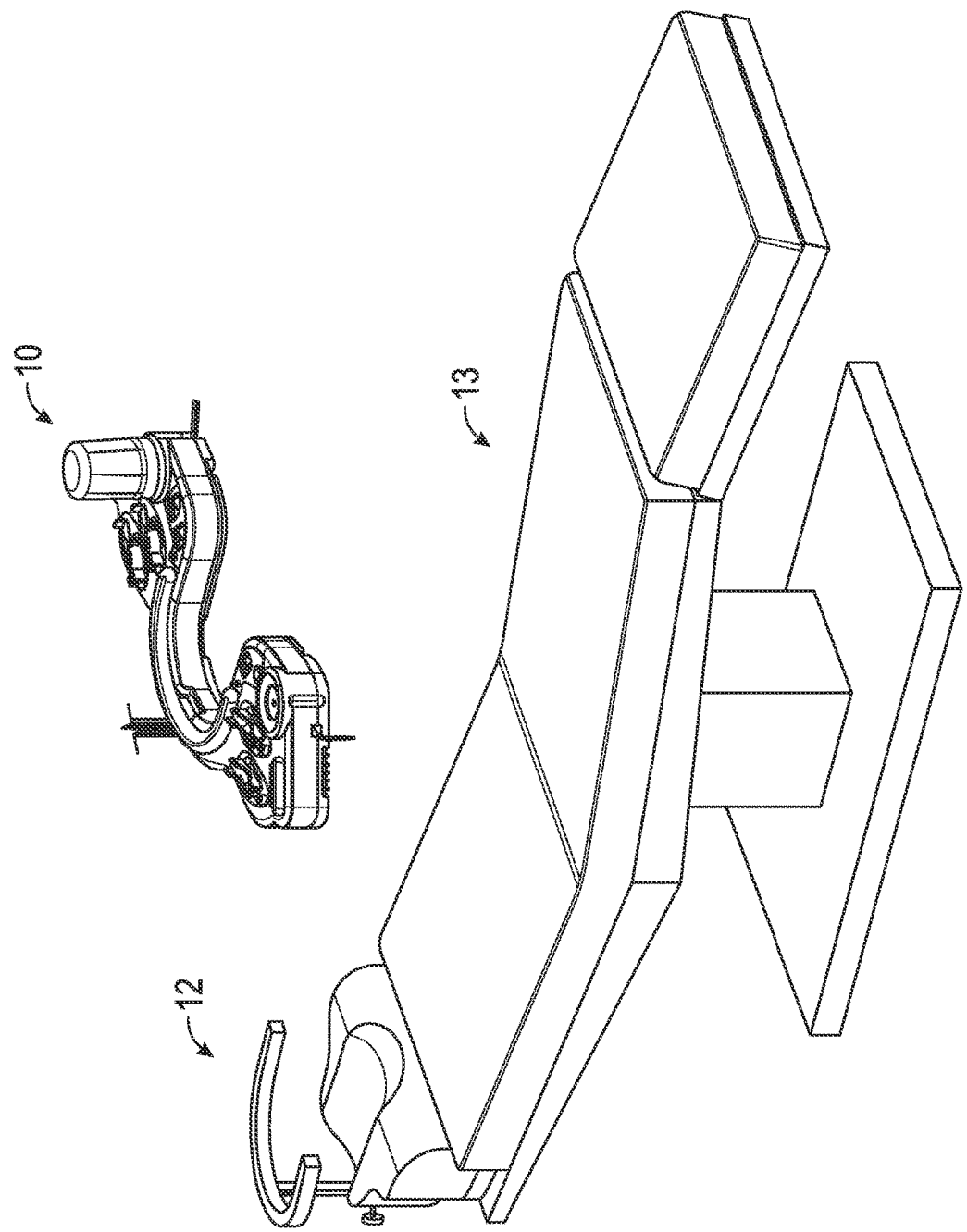
Figure 1E:
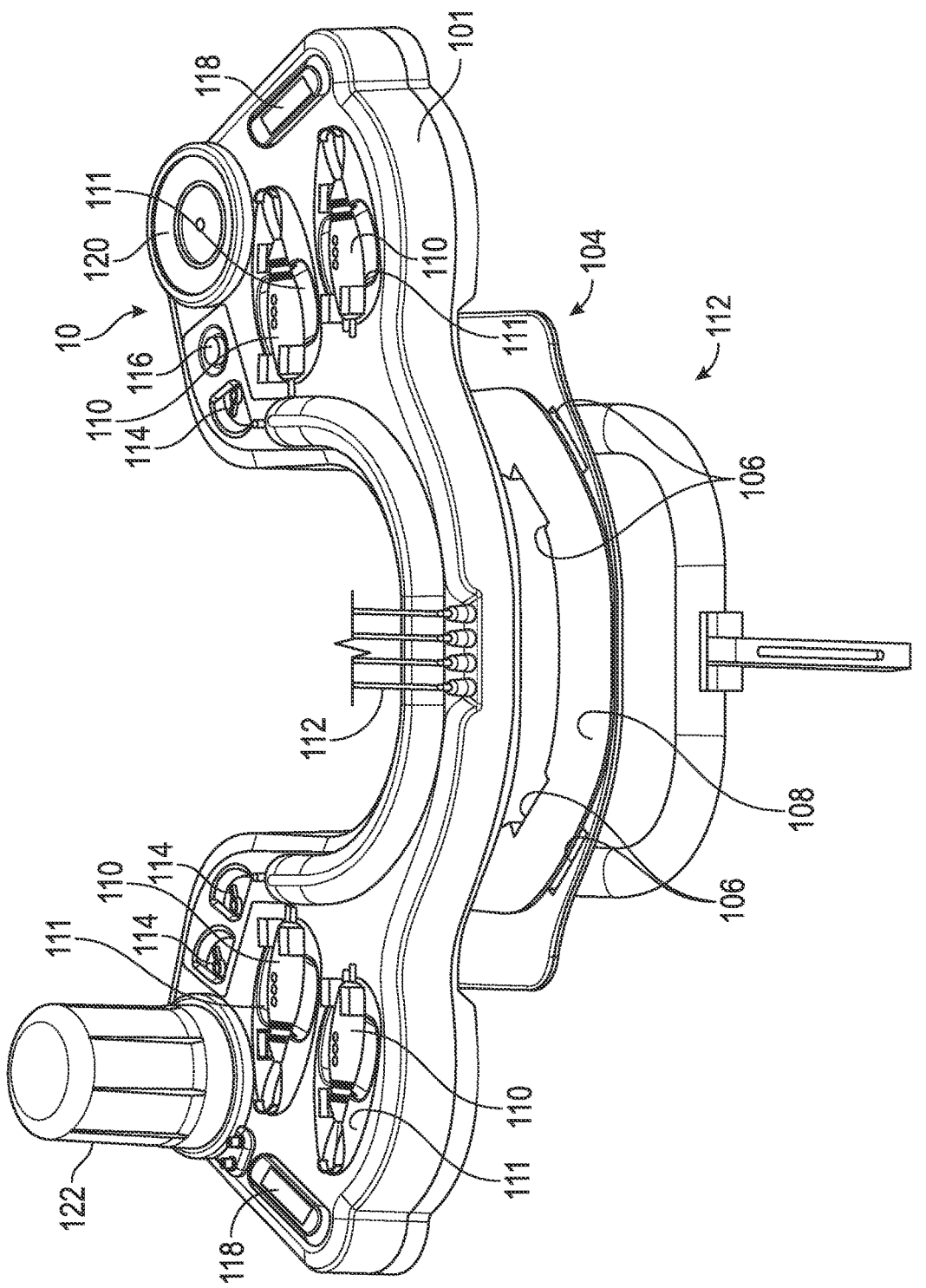

FIG. 1A illustrates an overhead or top view of the surgical tray 10 in use with a patient 2. In this embodiment, the surgical tray 10 comprises a void or cutout 102 shaped to be positioned around the patient's head. FIGS. 1B-1F further illustrate the surgical tray 10 and one way the surgical tray 10 may be mounted to a surgical table, chair, or gurney 13. In some embodiments, a surgical table 13 as shown in FIG. 1C comprises a support 12, such as a wrist support, shown in more detail in FIG. 1B. The support 12 comprises a support bar 16 and an end 14 configured to connect to a head of the surgical table 13. As shown in FIG. 1E, in some embodiments, a surgical tray 10 may comprise a top portion 101 configured to mate with a base portion 104. In the presently illustrated embodiment, the base 104 is desirably intended as a mounting structure to enable efficient and configurable mounting of the top portion 101 to the table 13. In some embodiments, as further described herein, a base portion may comprise more functional features, such as, for example, a motor and/or pump, electronics, and/or the like. The base 104 may comprise one or more slots 106 or other features configured to enable the base 104 to attach or couple to the support 112 of the table 13. In some embodiments, straps are used to hold the base 104 to the support 112, with the straps passing through the slots, grooves, or recesses 106. In some embodiments, the surgical tray 10 comprises a pad 108 positioned on top of the base 104 to, among other things, help remove any slack between the top portion 101 and the base 104 to maintain a sturdier connection between the top portion 101 and base 104.

Figure 1F:
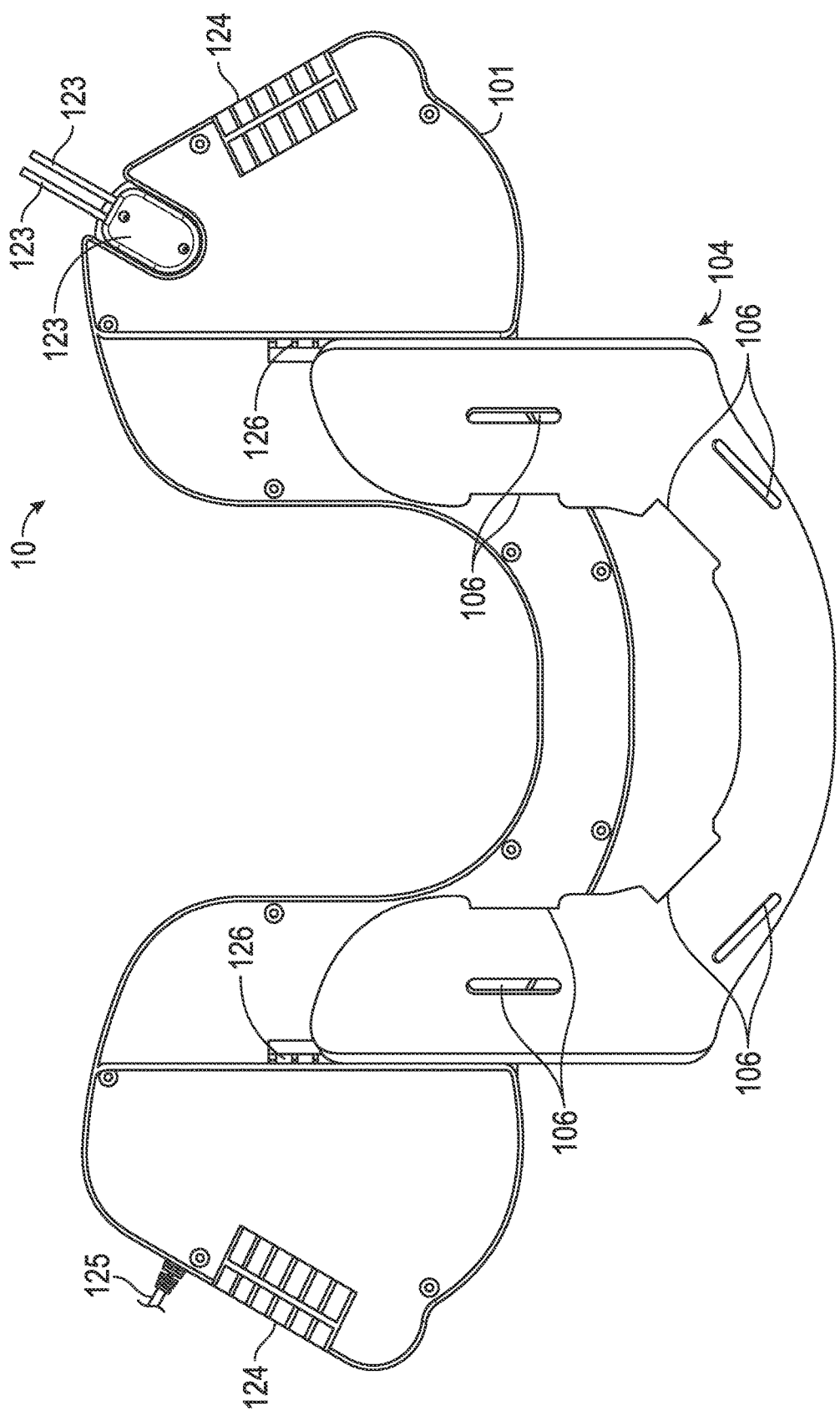

As can be seen in FIG. 1F, in some embodiments, a surgical tray is configured to slidably engage a base. In this embodiment, the surgical tray top portion 101 comprises latches 126 which engage the base 104. In some embodiments, levers or switches or handles 124 enable a user of the surgical tray 10 to selectively engage or lock the top portion 101 in position with the base 104. In some embodiments, the latches 126 are adjustable to enable the top portion 101 to lock in a plurality of positions, such as to accommodate patients of different sizes and/or a preference of the user. For example, in the embodiment illustrated in FIG. 1F, which is a bottom view of the surgical tray 10, the top portion 101 is illustrated locked in place in a position approximately halfway to a full engagement position.

FIG. 1E, which is an exploded view of the top portion 101, base 104, and support 112, illustrates several features of the surgical tray 10. For example, the surgical tray 10 comprises one or more handpieces or surgical tools 110, in this embodiment four handpieces 110. The handpieces 110 may comprise one or more tools for performing surgical functions, such as, for example, vitreous cutting, diathermy or electrocautery, illumination, and/or the like. In some embodiments, the handpieces 110 are tethered to the top portion 101 through cables or tethers 112. In some embodiments, a cable or tether 112 comprises one or more features, such as, for example, power transmission, electronic communication, communication through other methods, such as pneumatic or optical, and/or the like.

The surgical tray 10 further comprises a plurality of recesses or storage structures 111 configured to engage the handpieces 110 to hold the handpieces in place until they are needed and/or between surgical procedures. The surgical tray 10 further comprises a plurality of controls 114 to control a plurality of functions of the surgical tray 10, such as, for example, fluid infusion, oil infusion, air infusion, and/or the like. The surgical tray 10 further comprises a power button 116 configured to operate power to one or more devices of the surgical tray 10. One or more displays or indicators and/or light sources 118 of the surgical tray 10 enable information to be communicated to, for example, a user or surgeon during a surgical procedure. In some embodiments, one or more displays or indicators 118 may be located separate from the surgical tray 10, for example on the microscope or on the wall and connected to the tray via a wired or wireless connection. The surgical tray 10 further comprises a fluid reservoir receiver 120 and a balanced salt solution (BSS) bottle, container, sterile enclosure, or other holder 122. In this embodiment, a motor may be configured to be removable and/or removably coupled to a pump head 123, shown in FIG. 1F. The pump head further comprises pump input and/or output tubes 123. In some embodiments, it may be desirable to make a motor removable from the surgical tray 10 and/or pump head 123, so that, for example, a relatively expensive and/or higher-quality motor may be utilized, while a rest of the surgical tray 10, including the pump head 123, is disposable after a single procedure or a predetermined number of procedures. Various embodiments of coupling mechanisms that may be used to couple the motor to the pump head 123 are described in further detail below with reference to FIGS. 2A-2K.

In some embodiments, one or more surgical trays disclosed herein, such as, for example, the surgical tray 10 illustrated in FIGS. 1A-1F, may comprise one or more features similar to and/or one or more features that may operate similarly to those disclosed in U.S. Pat. No. 8,568,391, entitled STERILE SURGICAL TRAY, which is hereby incorporated by reference herein in its entirety.

Different embodiments may comprise removable and/or non-removable electronics that control the functions of the tray. The electronics may comprise one or more microcontroller(s) or microprocessor(s); the electronics may include any of a variety of sensors, including but not limited to pressure, vacuum, flow, temperature, light intensity, voltage/current/power, and inertial measurement. The electronics may also be designed to be low cost and therefore disposable after a single use or a limited number of uses. The electronics may comprise software or hardware features that prevent the use of the electronics beyond what was intended by the manufacturer. For example, the electronics may become inoperable after a single use to prevent reuse which can pose a safety risk to the patient (for example, because the system is no longer sterile) and protect sales revenue for the manufacturer. The electronics may also in some embodiments be designed to work for a limited number of uses, a limited amount of time, or until a pre-defined expiration date. For example, this would be useful to prevent the use of the system beyond what is considered reliable (for example, certain components may have a limited number of uses before the probability of failure becomes a risk, or the efficacy or sterility of certain components of the system may have a limited shelf-life). This could also be used in a subscription-style sales model, wherein the surgeon or hospital can purchase additional credits to use the system for additional surgical procedures or add/unlock additional functionality of the system. Some embodiments may also utilize non-electronic and non-software means of limiting reuse; for example the handpieces and/or tray components may be manufactured from materials that do not survive autoclave sterilization.

A tray in some embodiments may incorporate an internal power supply or transformer and rectifier that converts AC wall power to lower voltage DC. The tray may alternatively utilize a power supply separate from the tray (e.g. a "wall-wart" transformer or external brick power supply). The tray may also be powered by one or more single-use (primary) batteries (for example, alkaline, lithium manganese, or other chemistry) or rechargeable (secondary) batteries (for example, Li-ion, Li-Poly, NiMH, NiCd, or other chemistry). The batteries may, in some embodiments, be configured as a self-contained battery pack that can be removed from the tray itself. The tray may also derive power (electrical, pneumatic, and/or otherwise) from a separate console system to which the tray is coupled or from the surgical microscope.

In embodiments that comprise a reusable permanent or semi-permanent base that is separate from the tray itself, the base may be designed to incorporate any one or several of the following for benefits that include reducing the manufacturing cost of the tray, reducing waste, and using higher quality reusable components: electronics; displays; sensors (e.g. pressure, flow); power supply; one or more primary or secondary batteries or battery packs; pumps or components and sub-assemblies of a pump (e.g. the motor and drive circuitry) for example to be used for infusion, aspiration, and/or driving a pneumatic or hydraulic instrument; handpiece drive motors (e.g. for moving or rotating a transmission cable or torque coil connected to a vitreous cutter or other mechanical instrument); endoillumination light source; photocoagulation laser. The base and tray may implement features that allow the tray to be temporarily but reliably attached to the base, as well as to adjust or otherwise translate the position of the tray, for example to accommodate different patient geometries. In yet another embodiment, some or all of these features may be located in a footpedal (or more than one footpedal) that is used to control the functions of the surgical tray and handpieces. The footpedal may be tethered to the tray and/or handpieces through electrical connections (e.g. a cable assembly), pneumatic/hydraulic connections (e.g. tubing), optical connections (e.g. one or multiple optical fibers for broadband or narrow wavelength light that can be used for illumination, laser therapy, imaging, etc.), and mechanical linkage connections (e.g. transmission cables or torque coils for transferring the motion of a motor, piston, etc. located in the footpedal enclosure to the tray or handpieces.) In related embodiments, the footpedal may contain some of these elements but connect to pumps (e.g. for infusion and/or aspiration) that are located in the base unit or tray such that the tubing lengths between the pump and the patient are minimized.

Figure 2C:
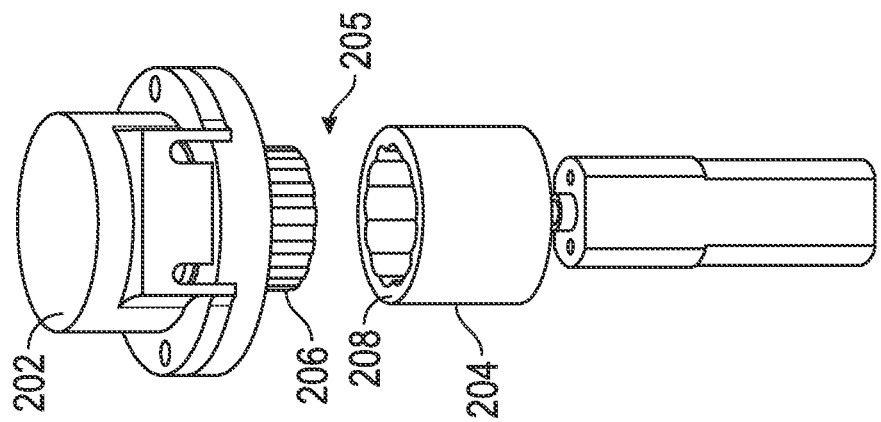
Figure 2B:
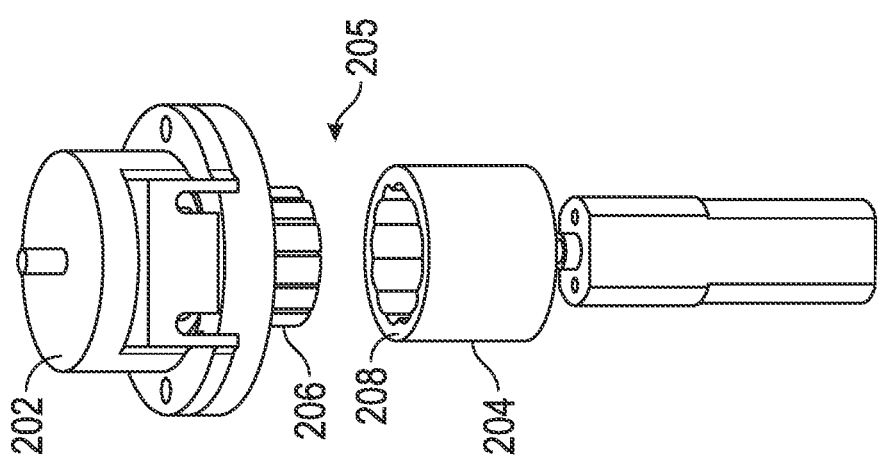
Figure 2A:
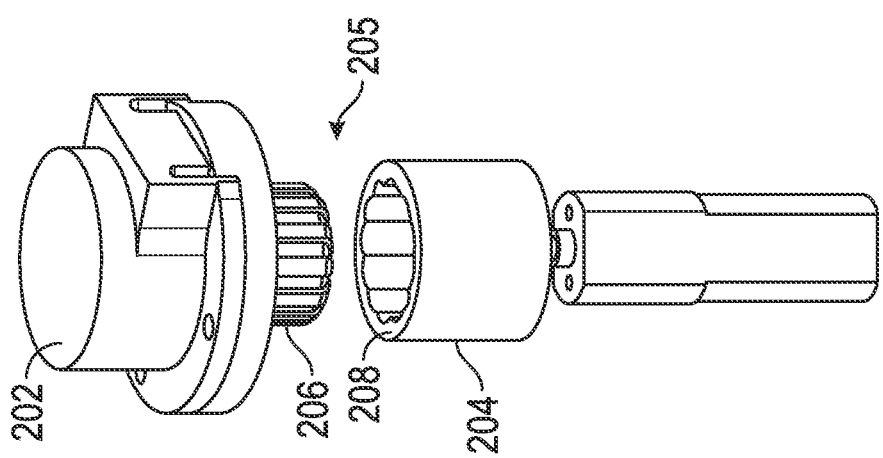
Figure 2F:
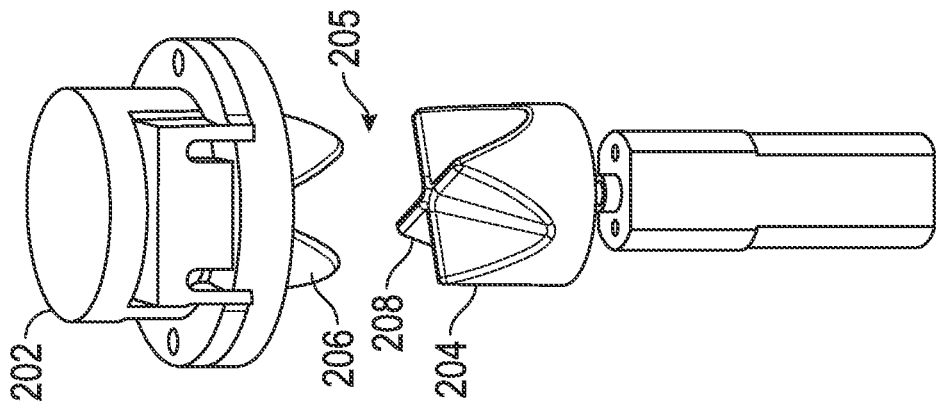
Figure 2E:
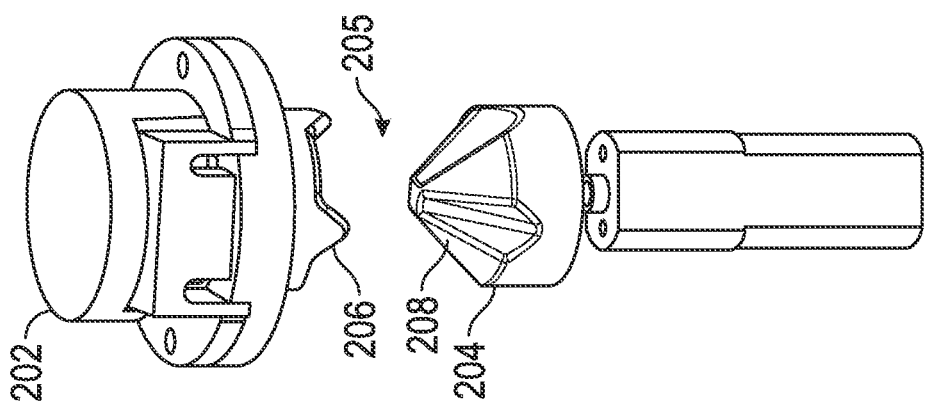
Figure 2D:
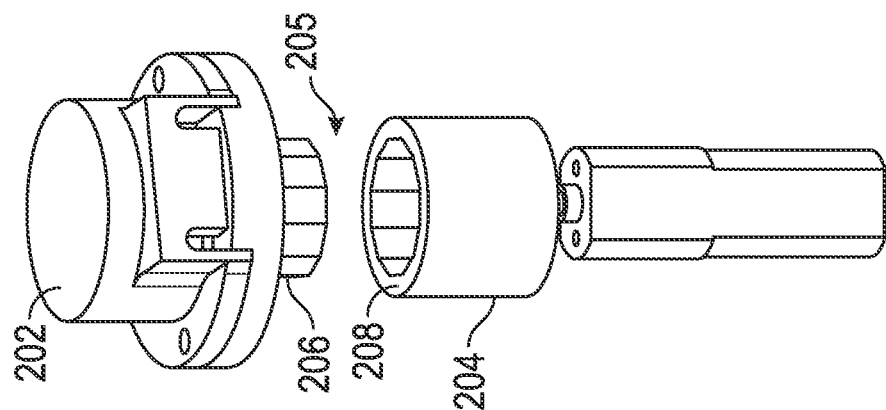
Figure 2I:
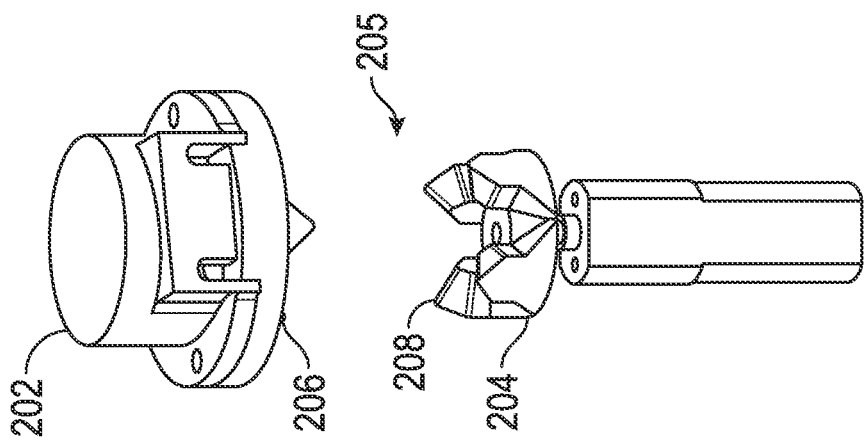
Figure 2H:
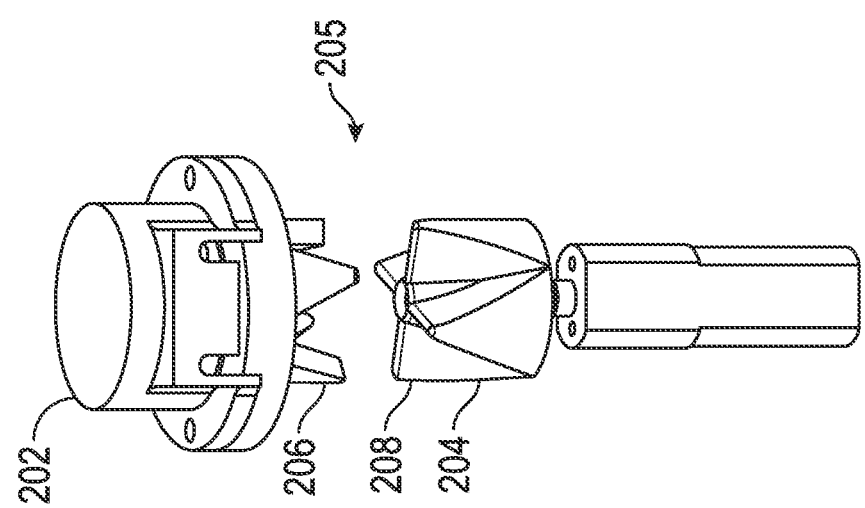
Figure 2G:
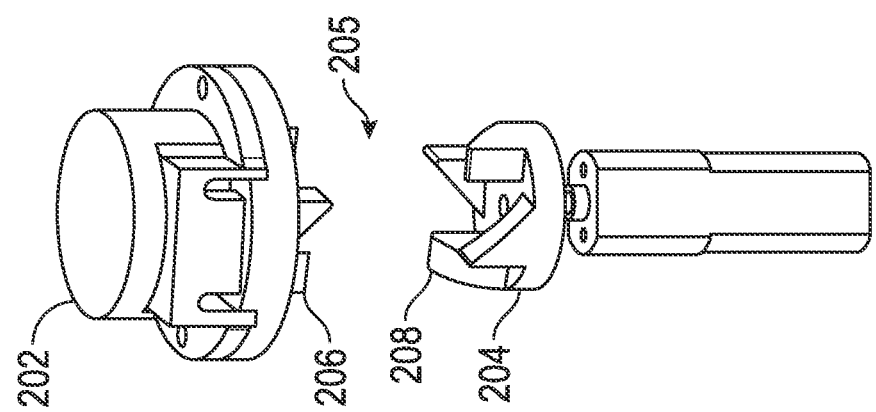

In embodiments with pump motors and/or handpiece drive motors in a separate base, the pump motors may couple to the pump heads in the tray and the drive motors may couple to the transmission cable or torque coil via spline couplings, shaft couplings, or similar that are aligned and engage when the tray is mounted or positioned on the base. FIGS. 2A-2K illustrate a variety of embodiments of couplings or coupling mechanisms 205 that may be configured to enable removable coupling of a motor output shaft and/or torque transfer mechanism 204 to a pump head 202. The embodiments illustrated herein comprises a pump-side coupling portion 206 and a motor-side coupling portion 208. In the embodiments illustrated in FIGS. 2A-2C, the pump-side coupling portion 206 comprises a male spline configured to couple with a female spline of the motor coupling portion 208. The male splines 206 are configured to slidably coupled with the female splines 208 to enable a torque to be transferred from the motor to the pump head 202. FIG. 2D illustrates an embodiment of a coupling 205 wherein a male portion 206 and a female portion 208 comprise mating flats, similar to a hex head bolt and socket that enable transfer of torque therethrough. FIGS. 2E-2K illustrate a variety of embodiments wherein alternating peaks and voids of a pump-side portion 206 engage alternating peaks and voids of a motor-side portion 208 to enable transfer of torque therethrough. Various other removable torque transfer couplings may alternatively be used. In other embodiments, the pump motors and pump heads are not readily separable and instead the pump tubing is separable from the pump head.

Functional Sterile Barrier

In some embodiments, an ophthalmic surgical system comprises a custom sterile barrier, such as a drape, that can be used to drape the non-sterile permanent base to create a sterile barrier before placing the tray on the base. The drape may in some embodiments be form-fitted to the base and tray. The drape may in some embodiments comprise one or more functional features, such as one or more features enabling light, electricity, a mechanical device, and/or the like to pass therethrough. For example, the drape may comprise one or more transparent windows to enable displays in the base to be viewed. In some embodiments, the drape may comprise perforations that are broken or pierced when the tray is mounted to the base to enable electrical, mechanical, and/or fluidic/pneumatic connections to be made between the tray and the base. In some embodiments, the drape may lack any perforations but nonetheless be punctured or perforated in specific areas when the tray and the base are mated. In some embodiments, the tray and the base may form a seal around the area to be perforated before the perforation occurs to ensure that a sterile barrier is maintained during the setup process. In some embodiments, the drape may have integrated electrical contacts such that one or more electrical connections can be made between the base and the tray without breaking or piercing the drape or otherwise compromising the sterile barrier. These electrical contacts may be formed, in some embodiments, by integrating separate contacts into the drape material, or the drape material itself may be made of a material or incorporate a material in the appropriate regions that is anisotropically conductive, such that electrical current can flow through the thin drape material but multiple adjacent current paths do not interact with each other. In other embodiments, electrical power is wirelessly transferred through the drape via inductive coupling of two antennas located on opposite sides of the drape or via similar wireless power transmission methods.

Figure 3A:
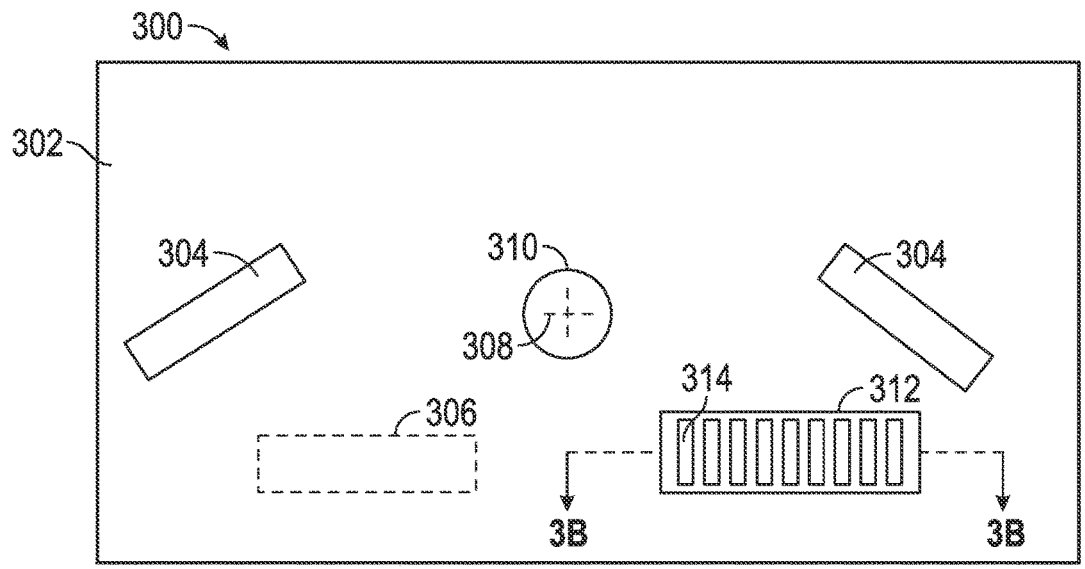
FIGS. 3A-3C illustrates embodiments of functional surgical drapes.

FIG. 3A illustrates a top view of an embodiment of a drape 300 incorporating a plurality of functional features. Drape 300 comprises a sheet of flexible material 302 configured and/or shaped and/or sized to be draped over, for example, a base portion of a surgical tray and or a patient's head to enable maintaining a sterile barrier during surgery. In some embodiments, the drape is configured to be positioned at least partially between a base portion and a top portion of a surgical tray, such as is illustrated in FIG. 4F, as further discussed below. In the embodiment illustrated in FIG. 3A, the drape 300 is illustrated as a rectangle for simplicity; however, in other embodiments, the drape 300 may be shaped differently and/or custom-fitted such that the drape is able to be positioned in a predetermined configuration over at least a portion of a surgical tray.

The drape 300 comprises two windows 304, such as transparent regions positioned to enable a user to view one or more displays of a surgical tray therethrough. For example, the windows 304 may be positioned to enable a user to view the displays 118 illustrated in FIG. 4A, as further described below. The drape 300 further comprises a perforated area 306 comprising a perforation enabling the perforated area 306 to be breached and/or removed when the drape 300 is placed into position, enabling a functional device to pass therethrough. For example, an electrical connection may pass therethrough, a mechanical coupling may pass therethrough, a pneumatic and/or hydraulic coupling may pass therethrough, an optical coupling may pass therethrough, and/or the like. The drape 300 further comprises an alternative perforation configuration 308. The perforation 308 comprises a perforation in the shape of a cross, such as to enable a tubular or other functional member to pass therethrough.

In some embodiments, one or more functional areas of a drape 300 comprise a sealing portion 310, shown in FIG. 3A as a circular area around the perforation 308. The sealing portion 310 may comprise, for example, a material that enables or aids in forming a sterile seal between, for example, a top portion and bottom portion of a surgical tray prior to the perforation 308 being breached or torn or opened. In some embodiments, the sealing portion 310 may comprise a resilient material, such as a rubber. In some embodiments, the sealing portion 310 comprises a ring of material (or otherwise shaped) that is stiffer than the primary drape material 302.

Figure 3B:
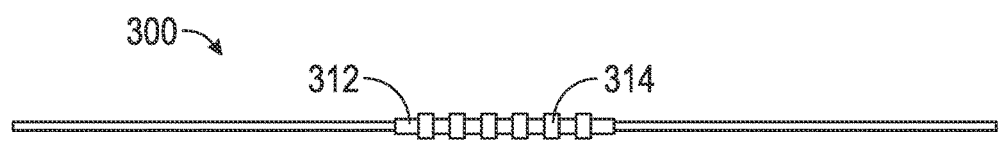

In some embodiments, the drape 300 comprises an electrical contact portion or region or block 312. The electrical contact portion 312 in this embodiment comprises a plurality of electrical contacts 314, such as electrically conductive material that enables a mating contact on one side of the drape 300 to be in electrical communication with a mating contact on an opposite side of the drape 300. FIG. 3B illustrates a cross section of the electrical contact portion 312. It can be seen in FIG. 3B that, in this embodiment, the plurality of electrical contacts 314 pass from one side of the drape 300 to another side of the drape 300, thus enabling electrical current to pass also from one side of the street 300, such as a sterile side, to another side of the drape 300, such as a nonsterile side.

Figure 3C:
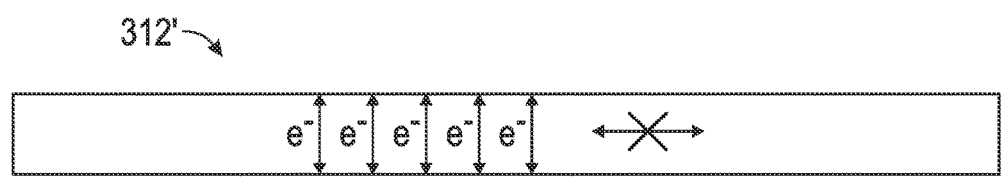

FIG. 3C illustrates a cross section of an alternative embodiment of an electrical contact portion 312'. In this embodiment, the electrical contact portion 312' comprises an anisotropically conductive material that, as illustrated schematically in FIG. 3C, enables electrical current to pass in one direction, such as from one side of the drape 300 to another side of the drape 300, but not in a transverse or perpendicular direction. Accordingly, a plurality of electrical contacts of a top portion of a tray may be configured to be in electrical communication with a plurality of electrical contacts of a bottom portion of a surgical tray through the electrical contact portion 312' without requiring a plurality of discrete electrical contacts on the electrical contact portion. This may, among other things, enable reduced manufacturing costs and/or an increased tolerance of positioning of the drape with respect to the surgical tray.

Modular Surgical Tray System

In some embodiments, a surgical tray as disclosed herein may be a modular system, with a base or reusable portion that is configured to have one or more modules coupled to it. In some embodiments, a base portion is configured to be reusable, at least for a predetermined number of procedures and/or length of use, while one or more in embodiments of modules are configured to be disposable, such as after a single use. In some embodiments, a module surgical tray system comprises a disposable top tray portion that couples to a reusable bottom tray portion. In some embodiments, a modular surgical tray system comprises a reusable tray having one or more locations for insertion of one or more functional modules, such as a motor/pump module, a fluid reservoir receiver module, a power adapter module, a modular tool insert comprising one or more handpieces, and/or the like.

In some embodiments, a reusable portion of a modular surgical tray system, such as a base portion, comprises one or more reusable functional units configured to couple to, communicate with, and/or the like, one or more disposable functional units of one or more modules. For example, in some embodiments, a reusable base portion may comprise a motor that is configured to couple with a disposable pump housing of a disposable module portion. In some embodiments, a reusable portion, such as a base portion of a surgical tray system or assembly, may comprise an electrical processing unit configured to control operation of one or more surgical tools and/or to detect inputs or conditions from one or more controls and/or surgical tools of a disposable portion. In some embodiments, a modular surgical tray system comprises a custom surgical drape, such as described above with reference to FIGS. 3A-3C, that is configured to be positioned between a reusable or base portion and a disposable or top portion or module.

Figure 4A:
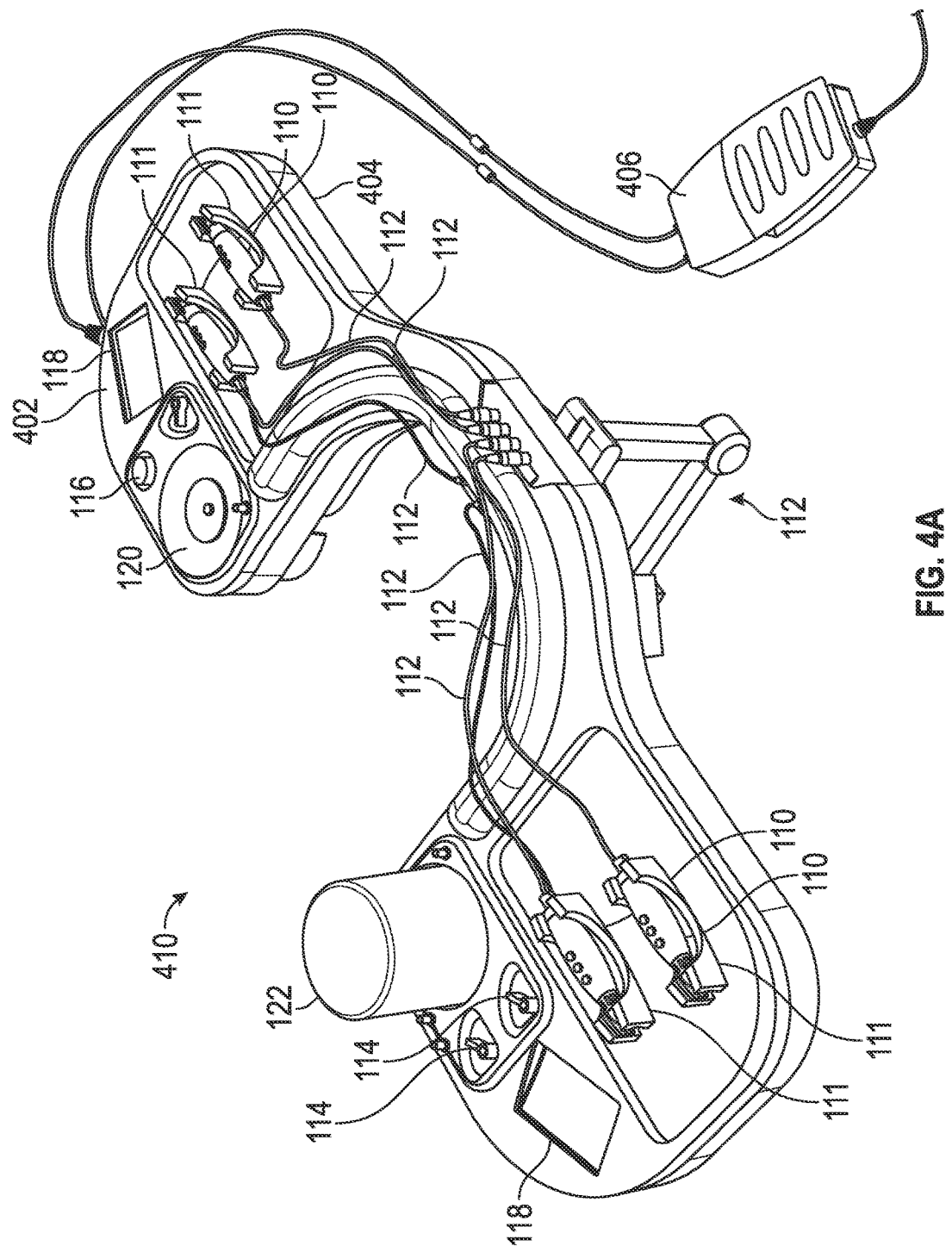
FIGS. 4A-4F illustrate embodiments of a modular surgical tray system.

FIG. 4A illustrates a perspective view of an embodiment of a modular surgical tray system comprising a top or disposable portion 402 coupled with a bottom or reusable portion 404. The bottom portion 404 is coupled to a support 112, such as a support at a head of a surgical table. The bottom portion 404 may be configured to mate with the support 112 in a variety of ways, such as, for example, straps that pass through slots, such as the straps 412 illustrated in FIG. 4B. The surgical tray 410 illustrated in FIG. 4A comprises a plurality of features similar in design to those of other embodiments described herein, such as, for example, a plurality of handpieces 110, storage or support locations for the handpieces 111, a plurality of tethers or cables 112 connecting the handpieces 110 to, in this embodiment, the bottom portion 404, a plurality of controls 114, a power button 116, two displays 118, a fluid reservoir receiver 120, and a BSS bottle 122. The embodiment illustrated in FIG. 4A additionally comprises a foot pedal 406 tethered to or in communication with the bottom portion 404 to enable control of one or more features of the surgical tray system 410.

Figure 4B:
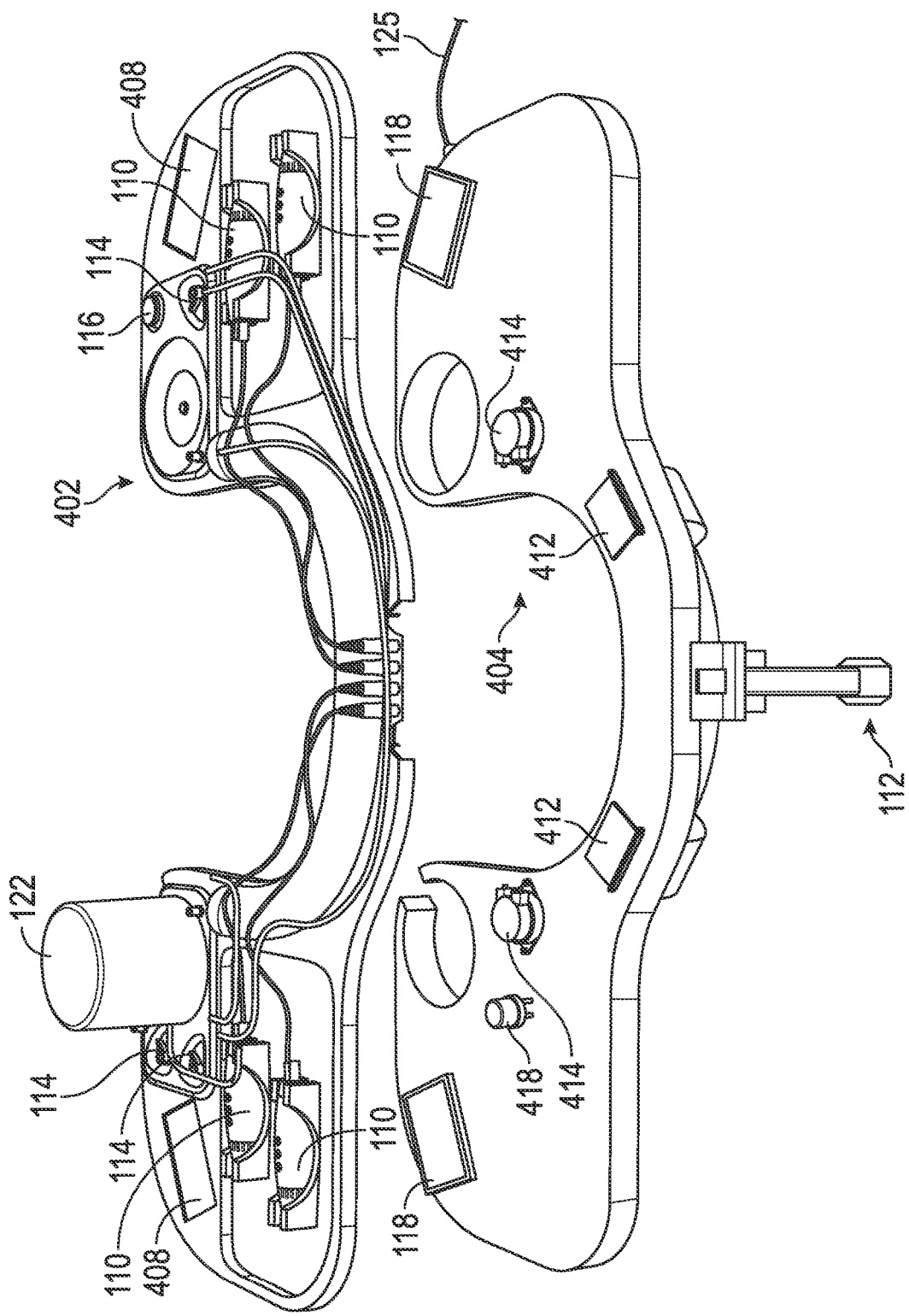
Figure 4C:
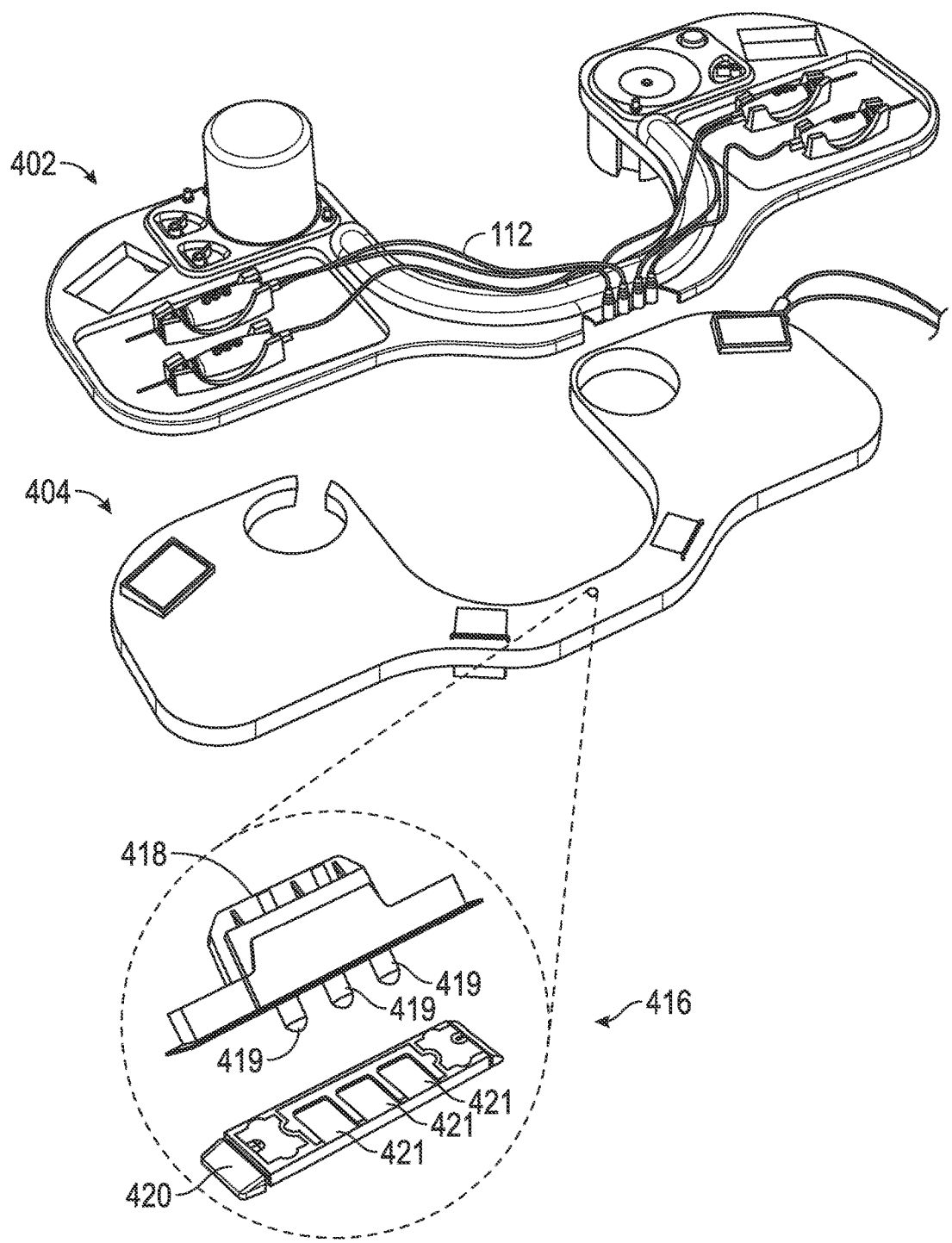

FIG. 4B illustrates an exploded view of the surgical tray system 410 showing the base portion 404 attached to the support 112, but the top or disposable portion 402 not yet coupled to the base portion 404. In this embodiment, some functional features of the base portion 404 are illustrated, including the displays 118, a light source 418 (in this embodiment an LED and in other embodiments the light source can be a laser, halogen lamp, or the like), and two pumps 414. FIG. 4C illustrates another example of a functional feature that enables electrical connection between the top portion 402 and the base portion 404. In this embodiment, the tethers or cables 112 are connected to a top electrical connector 418 that is part of or coupled to the disposable tray portion 402. The top connector portion 418 comprises a plurality of electrical contacts or pins 419 protruding therefrom and configured to engage mating electrical contacts 421 of a bottom connector portion 420 that is part of or coupled to the base portion 404. Accordingly, in this embodiment, the handpieces may be automatically connected to electronics or other features of the base portion 404 upon coupling of the top portion 402 to the base portion 404. In other words, a user of the system may not have to individually plug-in each handpiece after positioning the surgical tray top portion 402 over the base portion 404. In some embodiments, such a configuration can be advantageous to enable, for example, more expensive and/or durable components to be part of or coupled to the base or reusable portion 404, while the top or disposable portion 402 may be supplied as a single sterile assembly ready to be utilized for a single surgery and disposed of after surgery.

Figure 4D:
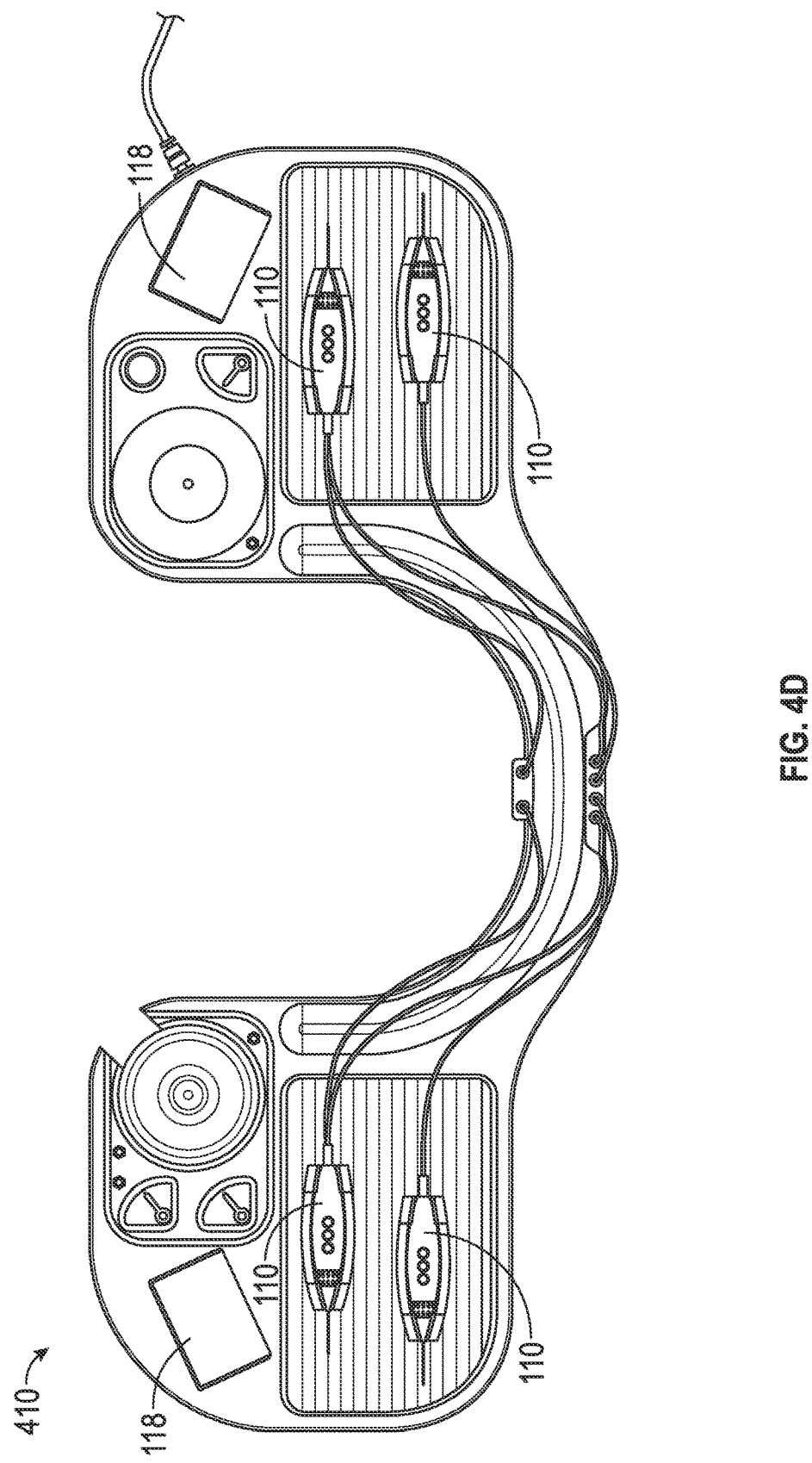
Figure 4E:
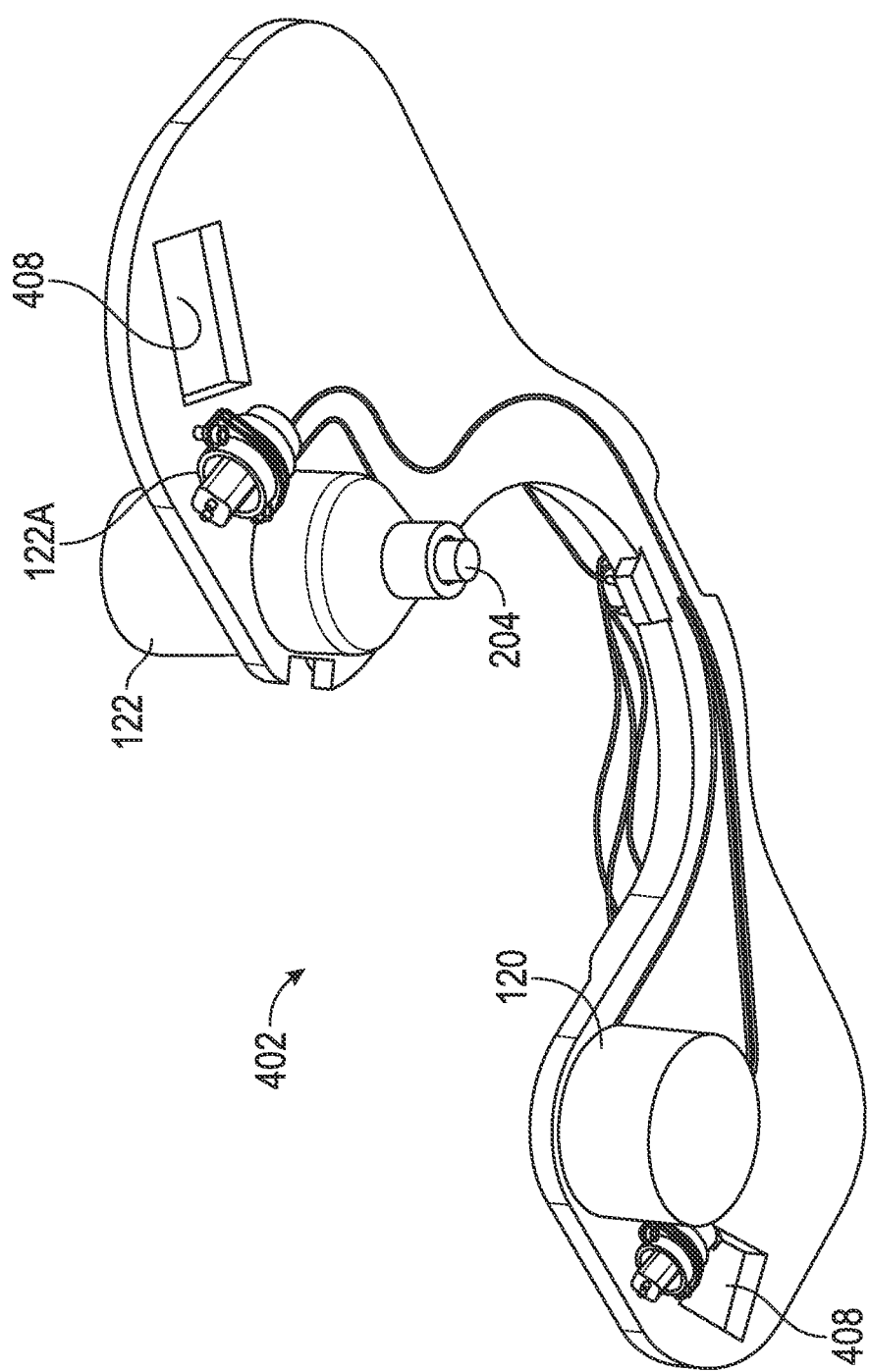
Figure 4F:
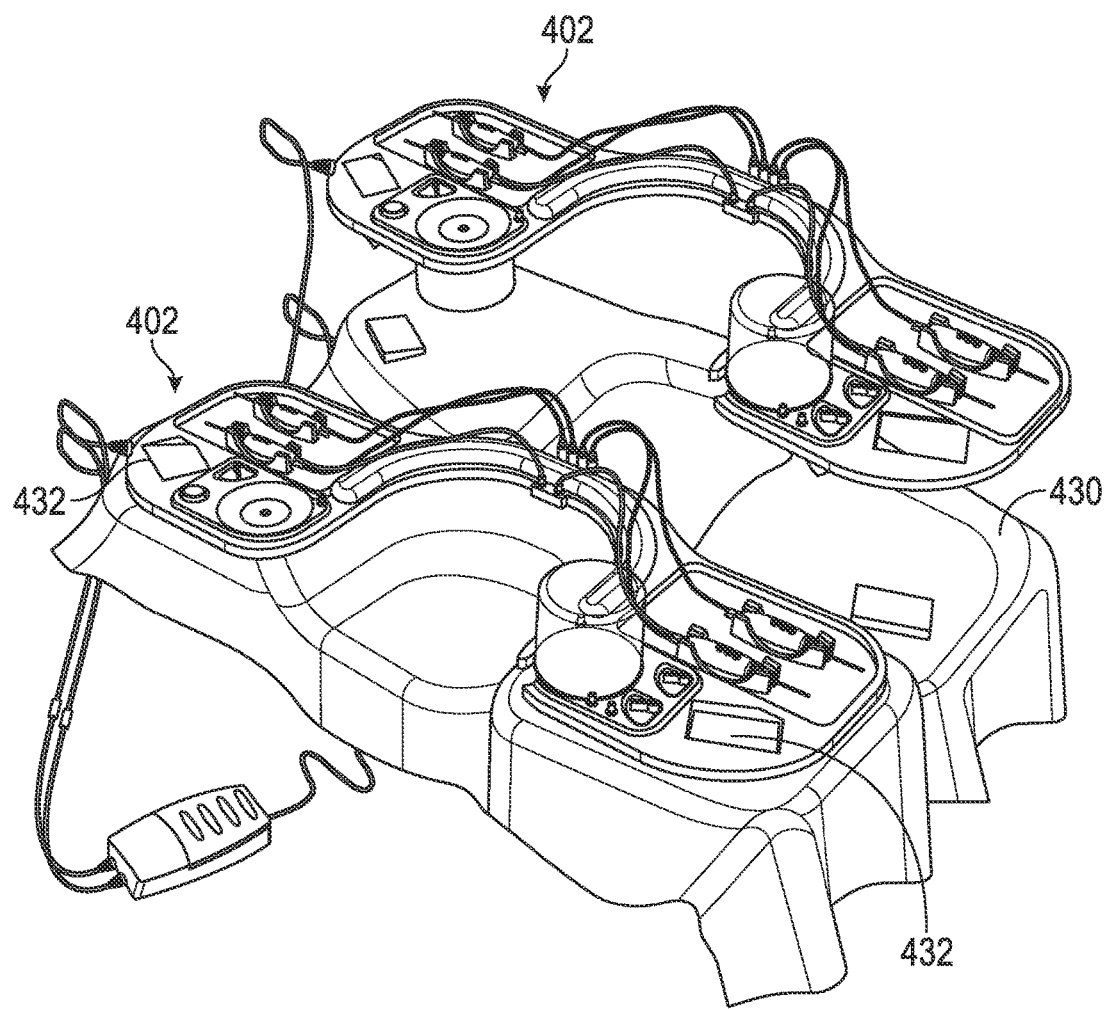

FIG. 4D illustrates a top view of the surgical tray system 410. FIG. 4E illustrates a bottom perspective view of the top or disposable portion 402 of the surgical tray system 410. The view in FIG. 4E illustrates in more detail openings 408 for viewing of the displays 118, and a drive portion 204 of the motor 122A, such as a coupling configured to mechanically coupled to a pump head coupled to a BSS bottle 122. In some embodiments, as described above, the motor 122A may be configured to be reusable and/or may be configured to be removable from the top or disposable portion 402 for use with another disposable portion 402.

FIG. 4F illustrates a fully assembled view and an exploded view of the top or disposable portion 402 of the surgical tray system 410 being positioned over the bottom portion 404 with a drape 430 positioned therebetween. It can be seen in FIG. 4F that the drape 430 comprises display windows 432 enabling viewing of displays of the bottom portion 404 through the drape 430. The drape 430 may further comprise one or more additional functional interfaces, as described above with reference to FIGS. 3A-3C.

Figure 5A:
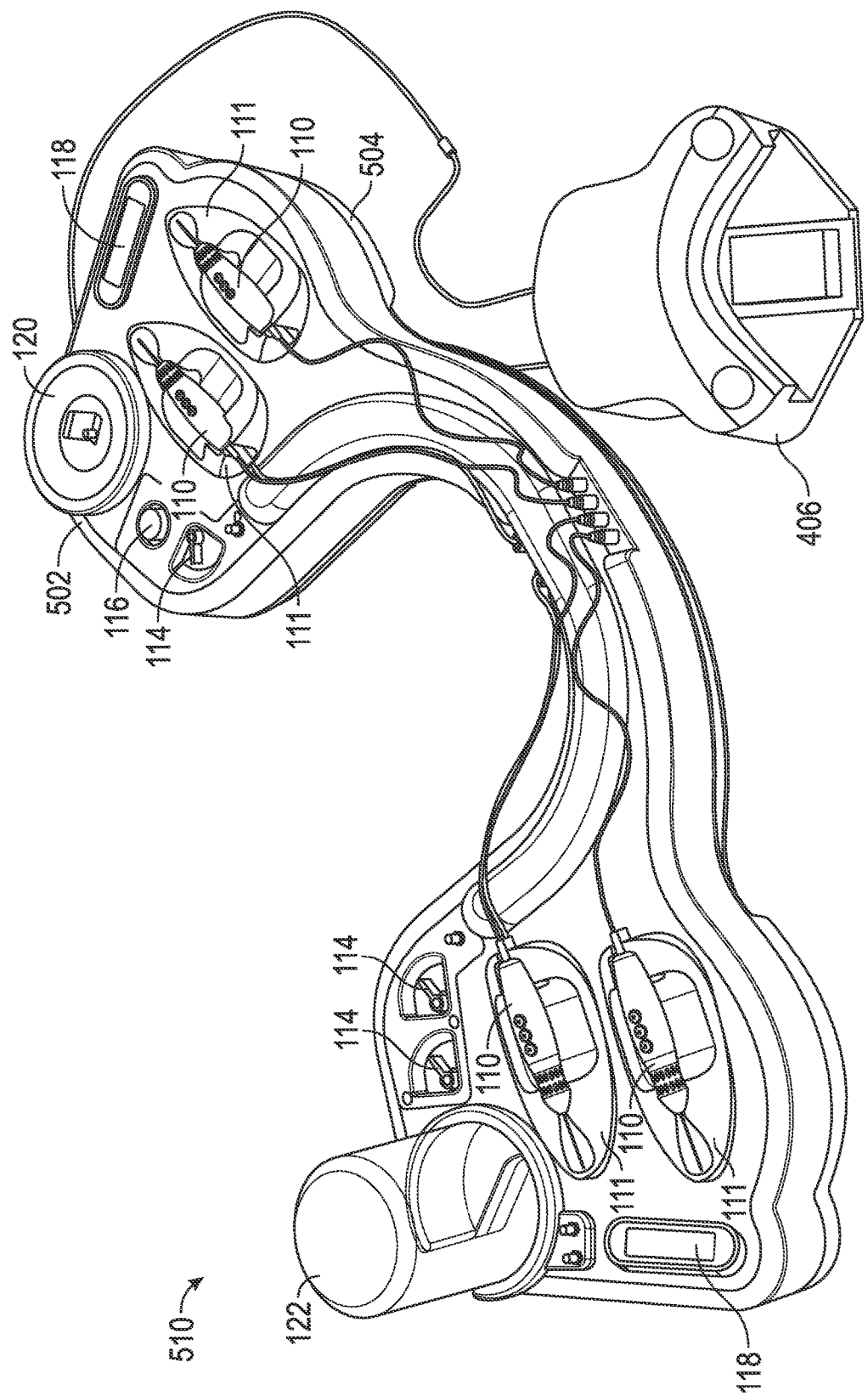
FIGS. 5A and 5B illustrate another embodiment of a modular surgical tray system.
Figure 5B:
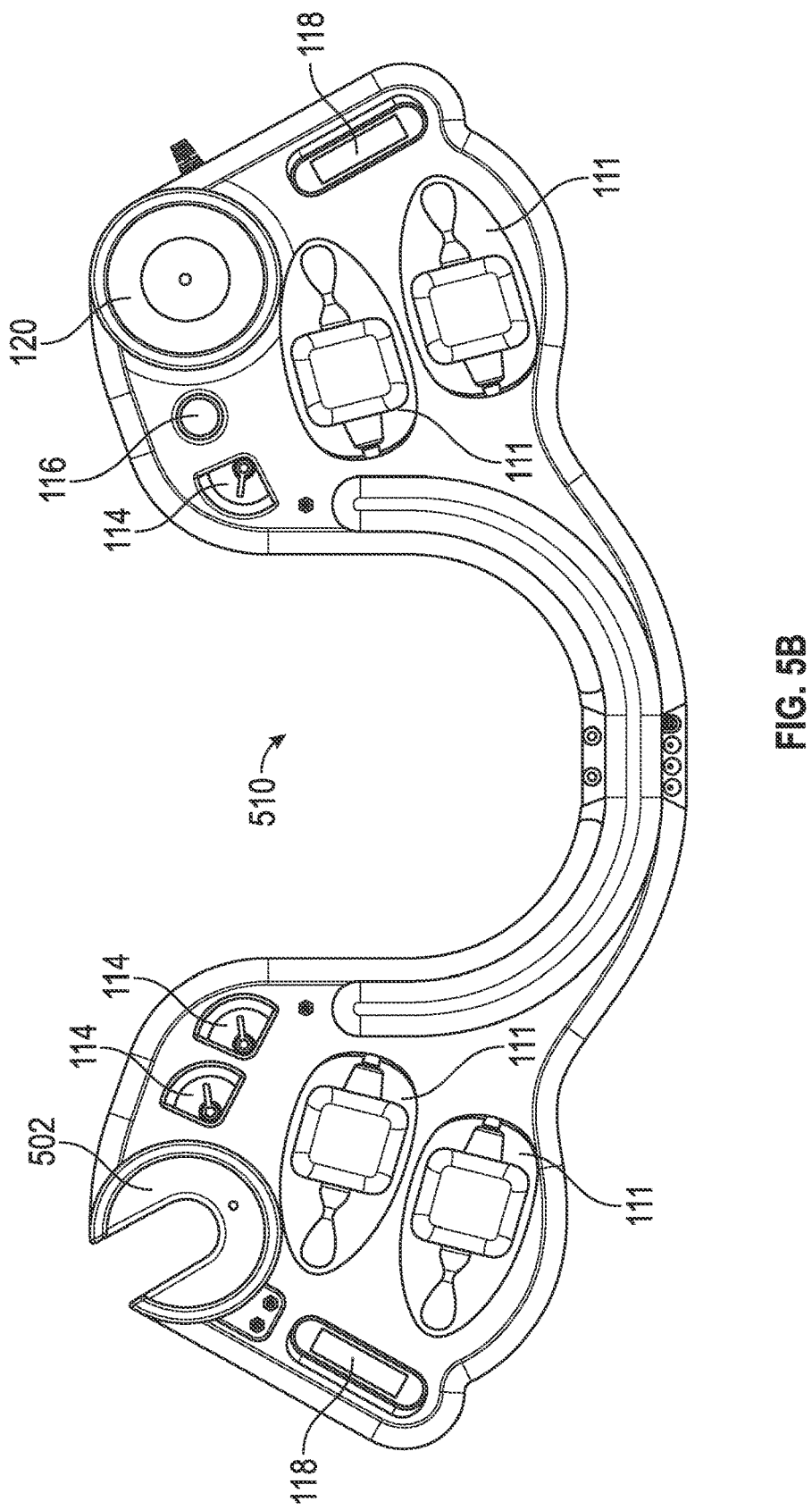

FIG. 5A illustrates another embodiment of a modular surgical tray system 510 comprising a top or disposable portion 502 coupled to a bottom or reusable portion 504. The modular surgical tray system 510 is similar functionally to the modular surgical tray system 410 described above, but with a different layout of and/or design of some of the features. Various elements of the surgical tray system 510 utilize similar reference numerals to represent features similar to those of the surgical tray system 410. FIG. 5B illustrates a top view of the surgical tray system 510 wherein the handpieces have been removed, illustrating the full handpiece support or storage locations 111. Further, the BSS bottle 122 has been removed, showing more detail of the motor receiving pocket or area 502.

Figure 6A:
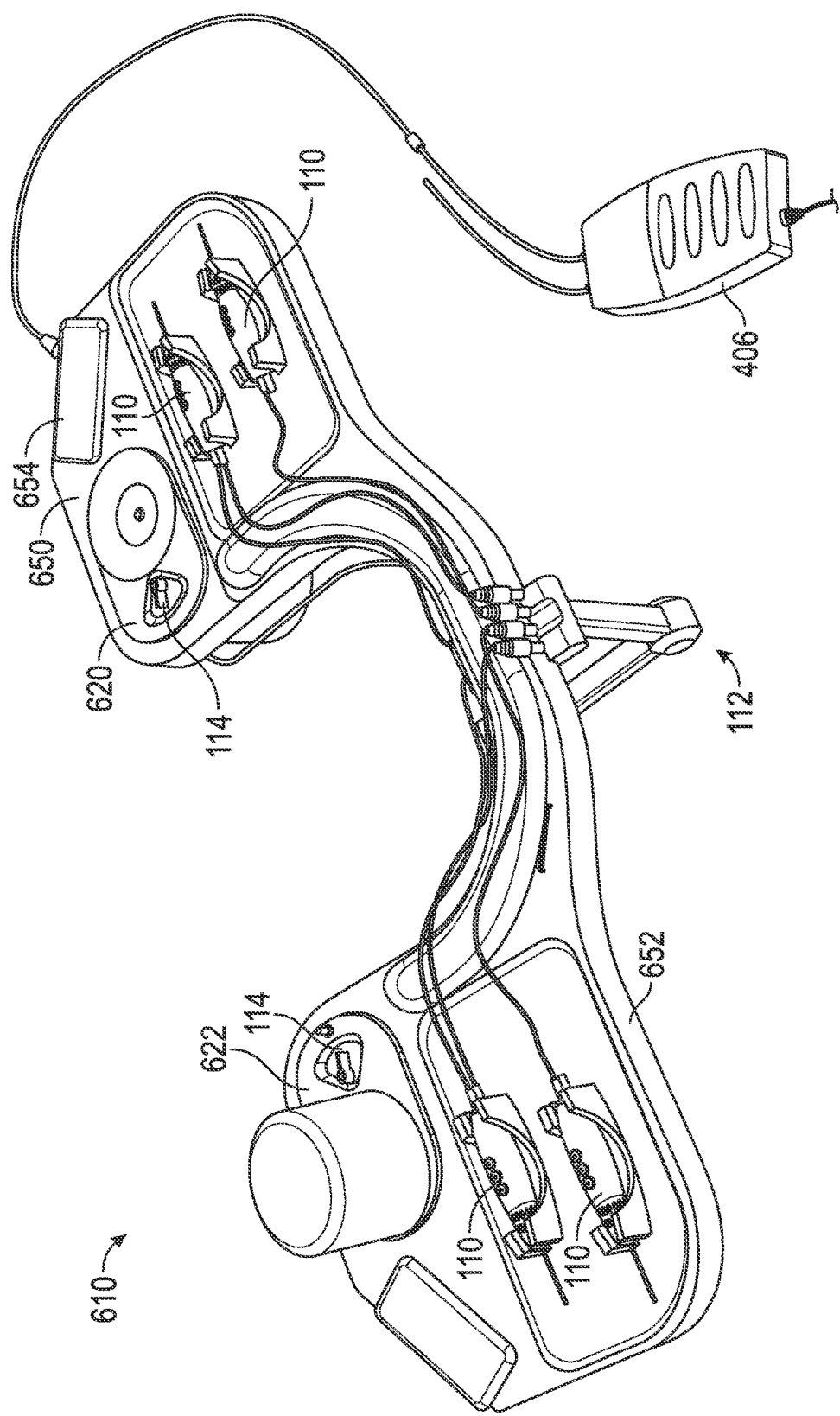
FIGS. 6A-6F illustrate another embodiment of a modular surgical tray system.
Figure 6B:
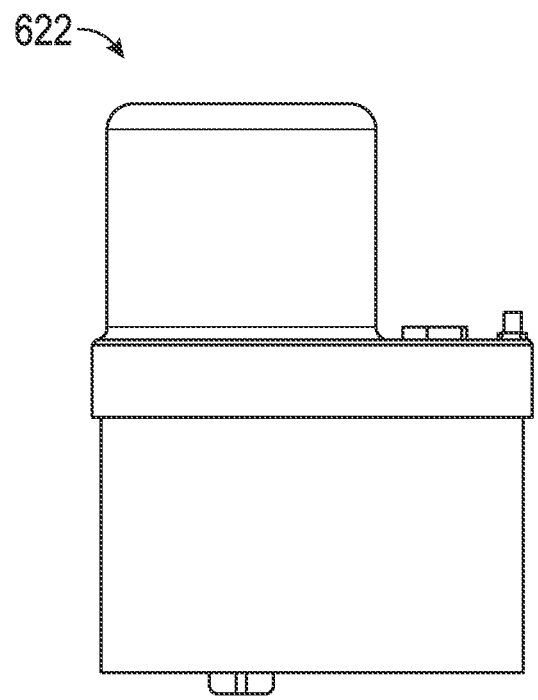
Figure 6C:
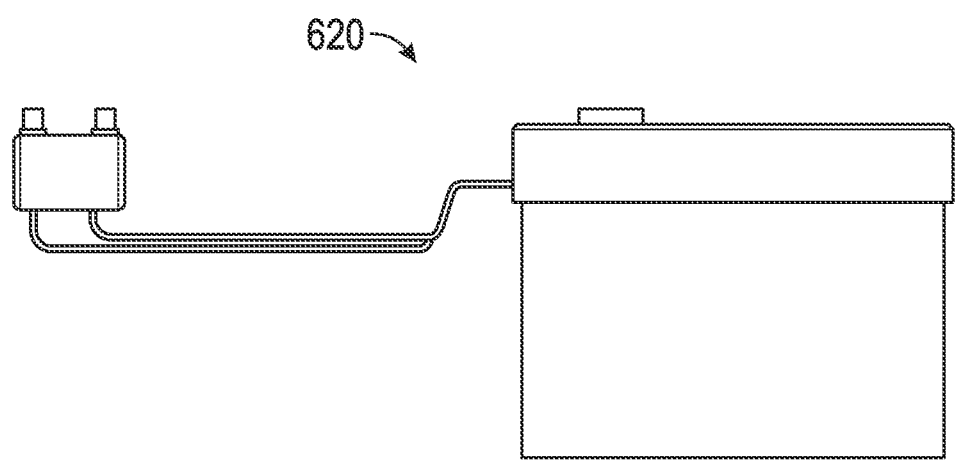
Figure 6D:
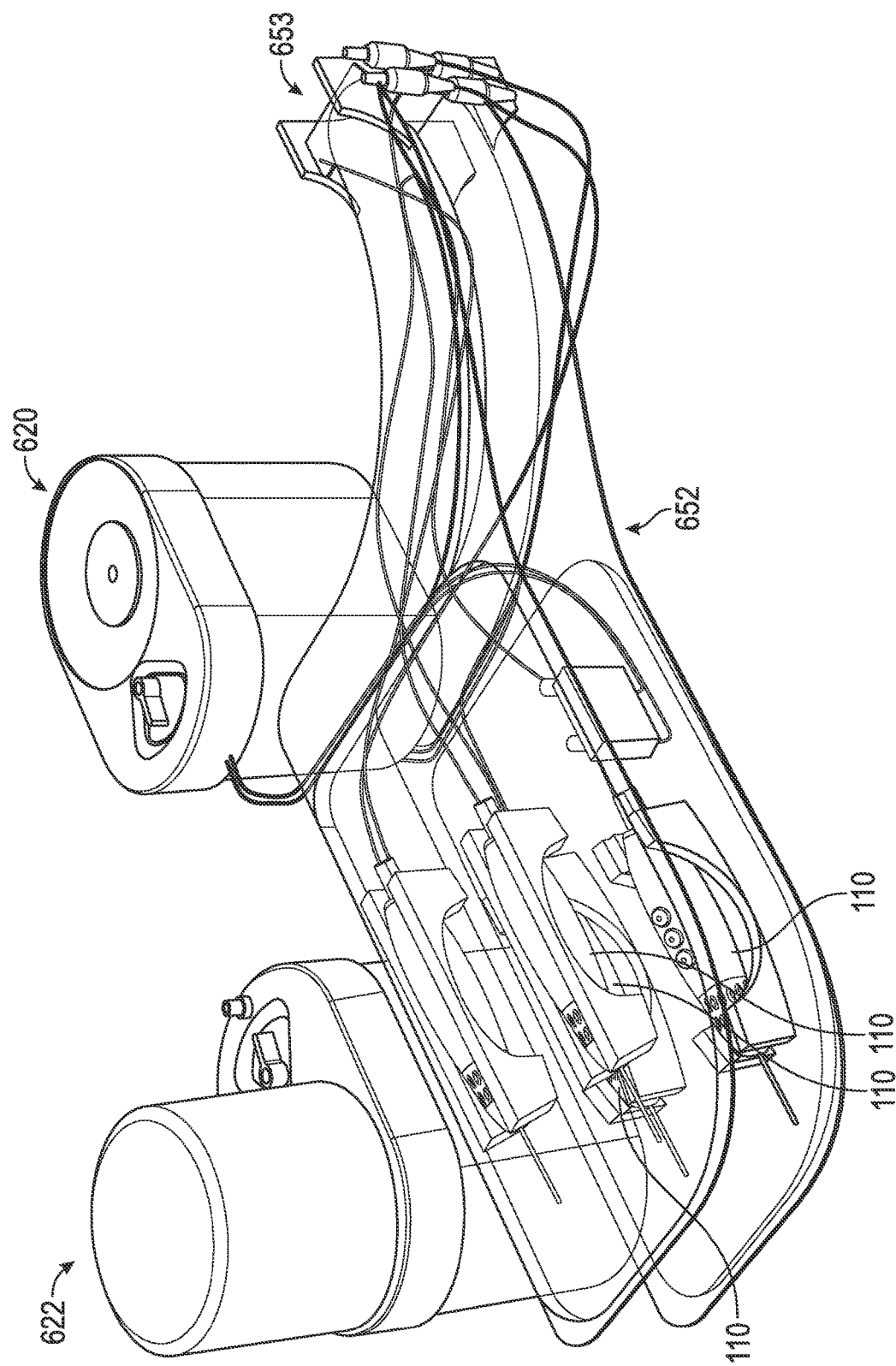

FIGS. 6A-6F illustrate another embodiment of a modular surgical tray system 610. In this embodiment, the modular surgical tray system 610 comprises a reusable or base portion 650 having a plurality of locations or interfaces configured for acceptance of or coupling to one or more modules. In this embodiment, the system 610 comprises a motor and pump module 622, a fluid reservoir receiver module 620, a power adapter module 654, and a modular tool insert 652. In an embodiment, the motor and pump module 622 can comprise a BSS bottle holder. In an embodiment, the motor and pump module 622 can comprise drive electronics for the infusion pump and/or the pressure sensor. In an embodiment, the drive electronics and/or the pressure sensor can be located in the reusable portion of the tray. In an embodiment, the fluid reservoir receiver module 620 can comprise the aspirated fluid reservoir and the aspiration pump. In an embodiment, the fluid reservoir receiver module 620 can comprise the drive electronics for the aspiration pump and the pressure sensor (or one or both of these may be instead located in the reusable portion of the tray). In an embodiment, the power adapter module 654 can be incorporated into one of the displays. In an embodiment, the power adapter module 654 can be located underneath the tray (in the reusable portion) or elsewhere (for example, on the ground, or the like). FIG. 6B illustrates a side view of the motor and pump module 622. FIG. 6C illustrates a side view of the fluid reservoir receiver module 620. FIG. 6D illustrates a perspective view of the motor and pump module 622, the fluid receiver module 620, and the modular tool insert 652, such as may come as a sterile package or assembly ready for use in a sterile operating environment. In this embodiment, it can be seen that the modular tool insert 652 comprises a folding or hinged joint 653 enabling the insert to be folded upon itself to reduce an overall package size of the insert, for example, to reduce a size during storage or shipping.

Figure 6E:
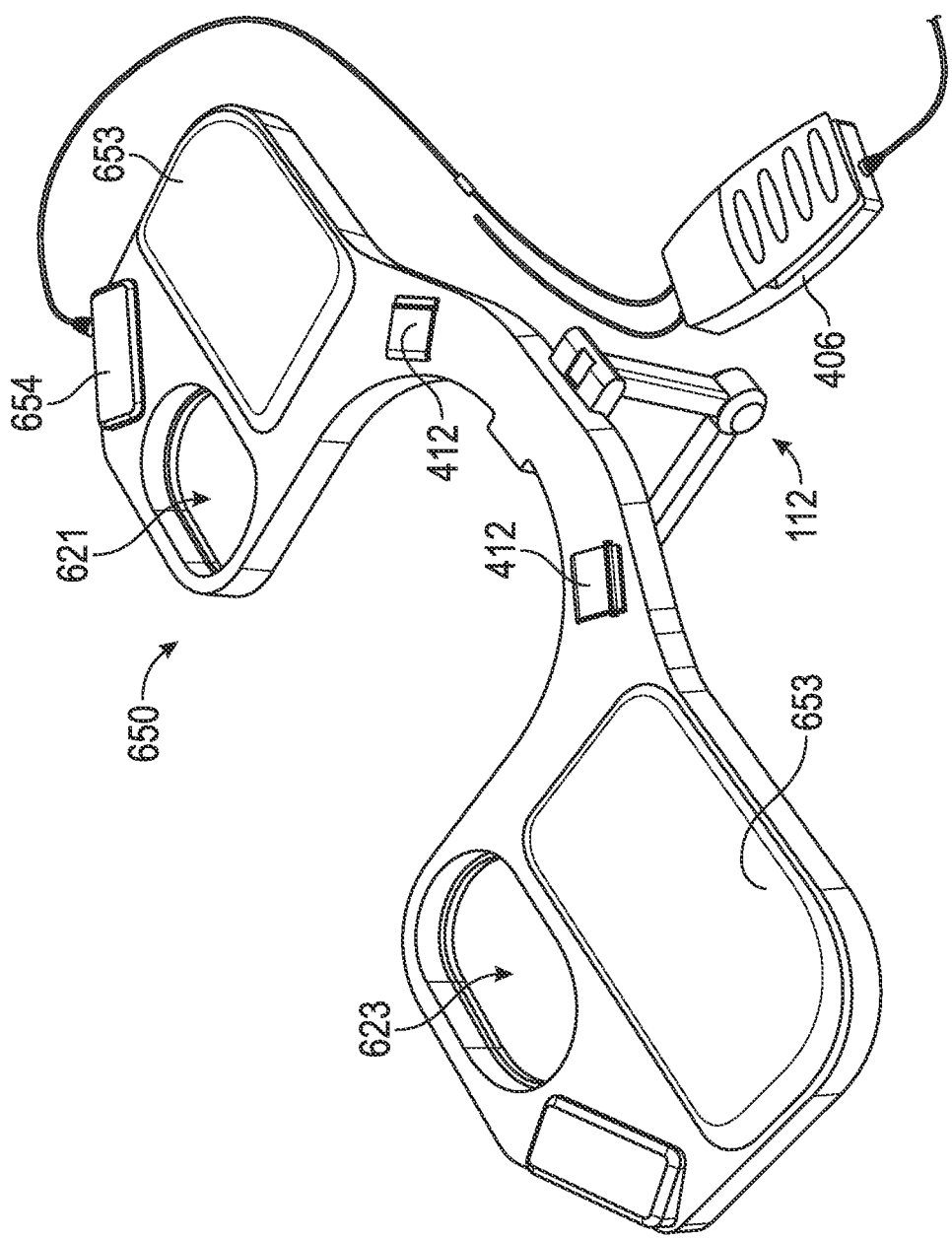
Figure 6F:
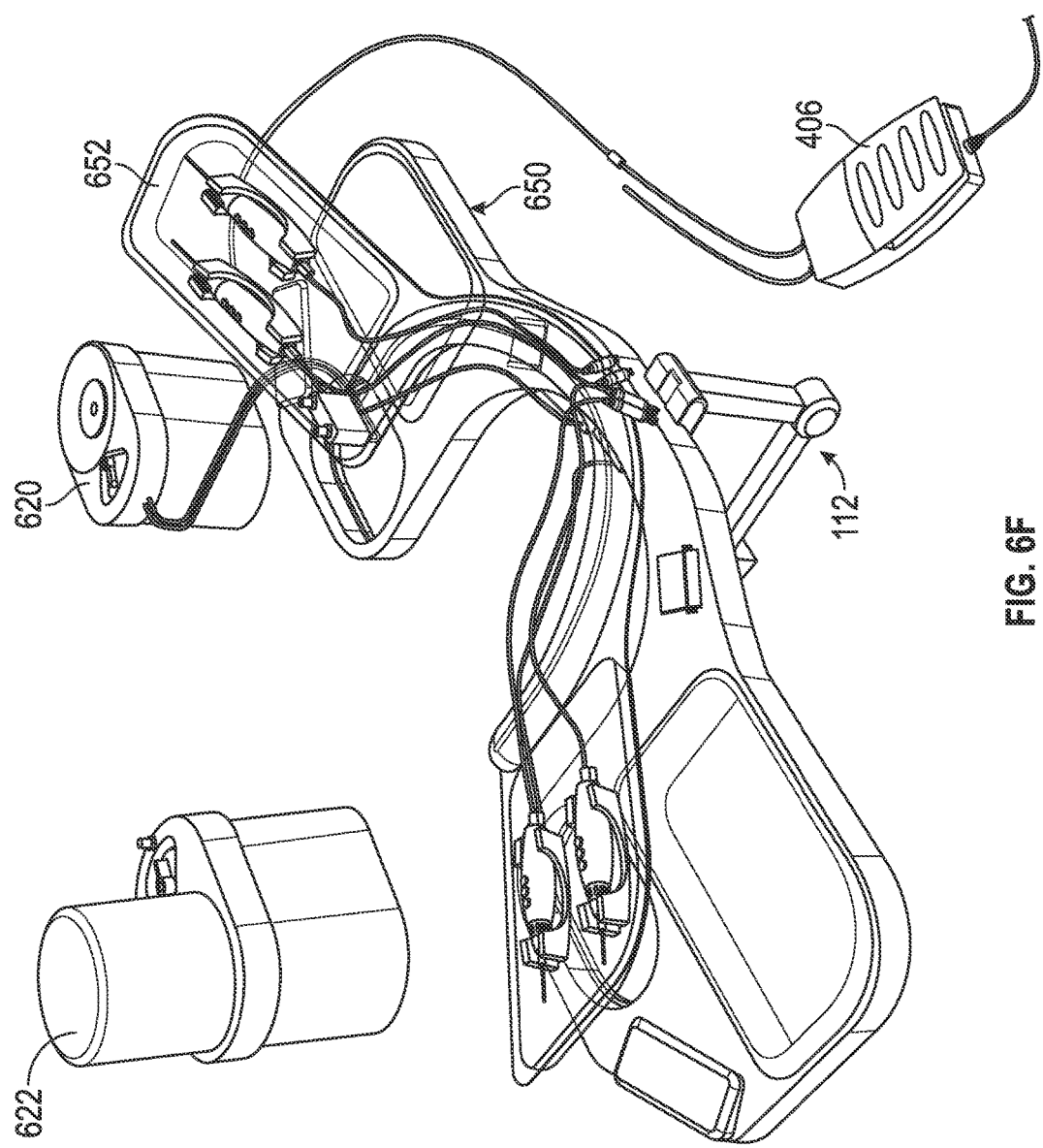

FIG. 6E illustrates a perspective view of the base portion 650 without the BSS holder, fluid receiver, or tool insert modules coupled thereto. The base portion 650 comprises a fluid receiver interface 621 shaped or configured to couple with the fluid receiver module 620, and a motor interface 623 configured or shaped to couple with the motor and pump module 622. The base portion 650 further comprises two tool insert interfaces 653 comprising recessed areas for locating and/or retention of the tool insert 652. FIG. 6A further illustrates straps 412 configured to retain the base portion 652 to a support 112. In some embodiments, the straps 412 (or another portion of the base 650) may comprise a feature that helps to retain the modular tool insert 652 to the base portion 650, such as a hook and loop fastener, a magnet, and/or the like. FIG. 6F illustrates an exploded view of the modular surgical tray system 610.

The tray in some embodiments may also be designed to connect to or otherwise mate with a separate surgical console. The tray and console may share electrical, mechanical, pneumatic, hydraulic, wireless, or other interfaces with each other. For example, in some embodiments the tray may provide a "docking station" or hub for the handpieces that can be conveniently located near the patient. This hub can be connected to the separate surgical console (electrically, pneumatically, and/or the like) and distribute the power (electricity, illumination, pneumatic/compressed air, hydraulic, mechanical, and/or the like) to the appropriate handpieces. The tray can also in some embodiments communicate information to the console, for example to control the power sources (voltage, current, pneumatic pressure, light intensity, and/or the like) and/or to display information on the surgical console's display.

The tray may also be designed in some embodiments to connect, mount, or otherwise mate to a surgical microscope or portion thereof. For example, the tray may be mounted to the optical head of the surgical microscope so that it hangs adjacent to the surgical site, or the tray may be mounted to the base or upright section of the microscope so that it is positioned adjacent to the surgical site. The tray may also be designed in some embodiments to tether power (electrical, laser, illumination, pneumatic, hydraulic, or other) and/or other functionality (e.g. data communication) from the microscope or a module connected to or mounted on the microscope.

Configuration of Profiles

The tray and/or base unit may also in some embodiments comprise a method of enabling the user to load specific settings and/or a user profile. For example, the tray or base may in some embodiments comprise a wireless RFID reader or near field communication (NFC) link that reads a "tag" (e.g. located on the user's ID badge) which is programmed with the user's preferences such as aspiration and infusion ranges, button functions, handpiece settings, and/or the like. In some embodiments, the tag comprises an identifier associated with the user's preferences, instead of the tag itself being programmed with the user's preferences. In some embodiments, the system is configured to automatically apply a user's preferences and/or to load settings associated with a specific user or tag when the tag is read by the wireless reader. In some embodiments, the tray comprises an antenna portion of the wireless reader, and the base comprises another portion of the wireless reader, such as a processing unit, which can be electrically connected to the antenna portion when the tray is connected to the base. Such a design can be advantageous to enable a more expensive portion of the wireless reader, such as the processing unit, to be reusable. The tray and/or base unit may in some embodiments comprise a USB or memory card interface or similar means of allowing the user to transfer information to the tray or base to, among other things, load or set settings and/or a user profile.

Figure 7:
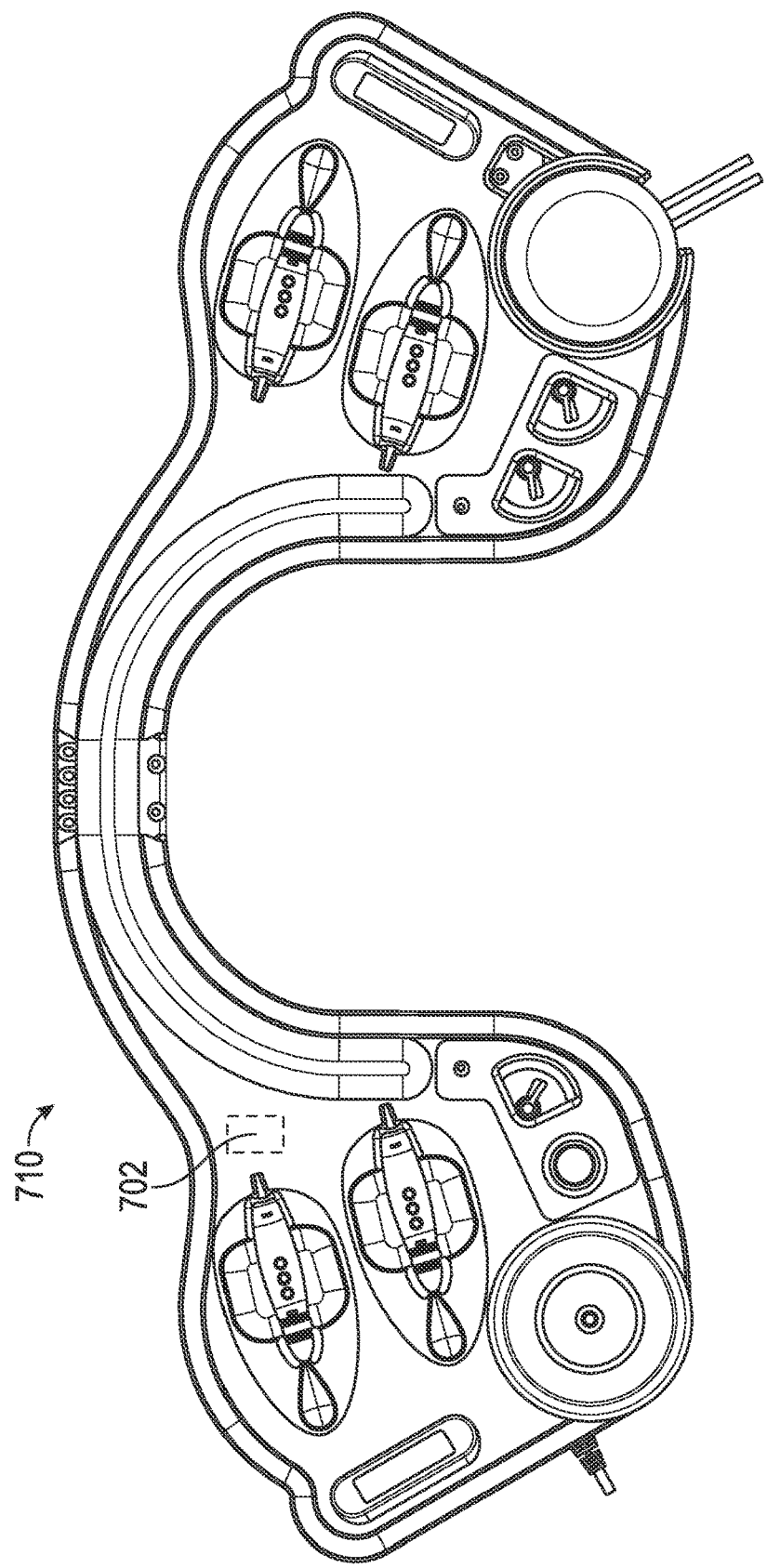
FIG. 7 illustrates another embodiment of a surgical tray system.

FIG. 7 illustrates a top view of a surgical tray 710 similar in design to the surgical tray 10 illustrated in FIG. 1A. The surgical tray 710, however, further comprises an antenna 702 configured to communicate wirelessly with a tag, near field communication device, and/or the like to enable configuration of parameters, user preferences, and/or the like. In some embodiments, the antenna 702 may be electrically coupled to a processing unit to enable the processing unit to configure the parameters, preferences, and/or the like.

Surgical Tray Components/Functions

A surgical tray in various embodiments can be configured to provide one or more of a multitude of components and/or functions for performing a surgical procedure. In addition to components and functions described above, the components and/or functions may comprise, but are not limited to: infusion, aspiration, one or more handpieces, illumination, laser therapy, display, audio feedback, one or more footpedals, and storage. These components and functions are described in greater detail below.

Infusion

The tray in some embodiments may provide infusion of fluids (balanced saline solution aka BSS and other fluids, including silicone oil, viscoelastic gels, dyes/stains, and/or the like) and/or gases into the eye, either the posterior or anterior chamber, for example by using a handpiece, such as one of the various handpiece embodiments disclosed herein. The infusion source (for example, a bottle or bag) may include a light (for example, an LED) to illuminate fill level, preferably but not necessarily the color red to minimize the impact on the surgeon's low light vision. The infusion fluid pathway may comprise in some embodiments a pressure and/or flow sensor to determine infusion and/or intraocular pressure and/or infusion flow rate. The fluid pathway and sensor may in some embodiments be separated by a filter or membrane to prevent contamination of the fluid and/or damage to the sensor, or in some embodiments non-contact measurement methods may be utilized. The tray may comprise in some embodiments a means of holding or securing the infusion fluid bottle or bag, such as a cup-holder or hook and/or the like, and a spike, needle, or fluidic attachment for extracting the contents of the bottle or bag. The tray may comprise one or more infusion systems to provide infusion for different fluids or gases simultaneously, on demand, or in a particular order. The tray may comprise stopcocks or other valves (manual or automated) to enable selection between different infusion sources (e.g. BSS or oil) or infusion locations (e.g. an infusion port next to the left eye vs. an infusion port next to the right eye).

In some embodiments, the tray may comprise multiple infusion systems, for example two separate systems located on opposite sides of the tray, each system designated for use with the adjacent eye. This can be advantageous to help ensure the tubing length from the infusion system to the patient's eye is minimized. The tray may also in some embodiments comprise multiple infusion systems (e.g. one for BSS and one for silicone oil) that are optimized for different viscosity fluids. In preferred embodiments, the total tubing length or fluid path length from either the infusion source (e.g. BSS bottle) or the infusion pump to the infusion cannula (which is inserted into the patient's eye) is minimized. Minimizing this fluid path length can improve the overall performance of the infusion system. The responsiveness of an infusion system that is actively maintaining an intraocular pressure level (e.g. via feedback control) during a surgical procedure is directly related to the length of the tubing set connecting the infusion source or infusion pump to the eye. Infusion systems with longer tubing sets, as is typical in commercially-available ophthalmology surgical consoles that are not located immediately adjacent to the patient, result in an undesirable lag or delay when measuring or adjusting the intraocular pressure as compared to those with shorter tubing sets. The infusion cannula can also be primed faster (before insertion into the patient's eye) in an infusion system with short tubing sets. In a preferred embodiment, this length (either source to cannula or pump to cannula) will not exceed 24 inches, but additional embodiments may be utilized that allow this length to reach 36 inches or more.

In one embodiment, the tray system comprises a separate infusion system for injecting silicone oil and similar viscous fluids. The oil infusion system may be a separate module that is utilized only in surgical cases that require oil infusion. The oil infusion system may be connected to a handpiece connector in order to supply power to the oil infusion system and provide a communications interface between the oil infusion system and the tray or base electronics. In some embodiments, the oil infusion system is designed as a handpiece with an endoscopic needle or tube that is used to infuse the oil or fluid into the eye. In other embodiments, the oil infusion system interfaces to the infusion cannula already inserted in the eye for BSS infusion. The infusion of oil may be done manually (for example, by depressing or squeezing a plunger and/or the like), it may be done pneumatically or hydraulically (for example, using a separate pump, compressor, compressed gas source, and/or the like), or it may be done electromechanically, for example with a motor, solenoid, or similar actuator that can infuse the oil (for example, a ballscrew/leadscrew, Hamilton syringe type configuration that moves a plunger to expel the oil from a syringe or cartridge, and/or the like).

Some embodiments utilize a pump or other means to provide fluid infusion. The pump style may be a standard Venturi, peristaltic, or diaphragm design, or another standard or non-standard pump variety. The infusion system may in some embodiments rely on other mechanisms of action to achieve fluid infusion, for example a fluid-filled syringe depressed either manually (for example, by the surgeon or an assistant) or automated (for example, via a syringe pump mechanism, actuator, motor, servo, ballscrew/leadscrew, spring, and/or the like).

Some embodiments may be configured to use a manually or automatically adjustable pole to raise or lower the BSS bottle or bag, exploiting gravity to provide a variable infusion pressure related to the height of the fluid source.

Some embodiments may be configured to pump air into or out of the fluid bottle to control the infusion pressure and therefore intraocular pressure (forced gas infusion). Pumping gas into the bottle increases the infusion pressure, while drawing air out of the bottle via pumping, vacuum, or venting (for example, through a tube or needle whose intake port is located above the water level) decreases the infusion pressure. Using this technique not only enables precise control of the infusion pressure but it also helps dampen pressure spikes and dips. The pulsating flow output of a peristaltic pump can also be minimized when using the peristaltic pump to pump air into the fluid bottle to increase infusion pressure.

Some embodiments utilize a compressed gas, e.g. a nitrogen or other gas (preferably inert) filled cartridge, canister, or tank as a source of pressure to enable fluid infusion (for example, via Venturi action or forced gas infusion). The cartridge, canister, or tank may be reusable/refillable or disposable and intended for single-use or limited use.

Some embodiments utilize a soft infusion fluid bag (as opposed to a glass or rigid plastic bottle). The soft bag may in some embodiments be located in a fixture between two or more plates that can squeeze or otherwise exert pressure on the bag in one or more axes. The distance between the plates (and thus the squeeze force) can be controlled manually by the surgeon or assistant or automatically, for example through a mechanical system comprising one or more of an actuator, motor, servo, cam, solenoid, gear, ratchet, rack and pinion, band, belt, pulley, chain, and/or the like. Increasing the squeeze force increases the infusion pressure; decreasing the squeeze force decreases the infusion pressure. Likewise, a similar mechanism can be used on a smaller container of infusion fluid, for example a reservoir into which infusion fluid drips or flows from the original infusion bottle or bag. A check valve can be included in some embodiments to prevent backflow into the original bottle or bag. The soft bag may also be located in an air-tight rigid container, which can have air pumped in or out (or vented) to increase or decrease the pressure on the external surface of the bag. Since the bag is not rigid, but compressible, the infusion pressure can be adjusted by adjusting the pressure in the rigid container. Likewise, a similar mechanism can be used on a smaller container of infusion fluid, for example a reservoir into which infusion fluid drips or flows from the original infusion bottle or bag. A check valve can be included to prevent backflow into the original bottle or bag.

In some embodiments the infusion fluid(s) are included in or integrated into the tray system so that the tray and fluid are packaged, sterilized, and shipped as a single system that can be disposed of after the surgical procedure. This is in contrast to a system wherein the tray is packaged, sterilized, and shipped as a separate component than the infusion fluid (e.g. BSS bottle) which may be from a different manufacturer altogether. Such a system may also include a separate additional means of introducing infusion fluids into the fluidic path of the system, for example if the included fluids are exhausted during the surgical procedure.

Aspiration

In some embodiments, the tray may provide aspiration functions, for example from a vitreous cutter, soft-tip, or phaco handpiece. The aspiration function may be provided through the use of a pump or by another means. The pump style may be a standard Venturi, peristaltic, or diaphragm design, or another variety. The aspiration pump system may also rely on other mechanisms of action to achieve vacuum draw at the needle tip, for example a syringe with a depressed plunger connected to the aspiration needle either directly or via a tube, the plunger being drawn back to produce a vacuum force, the action of being drawn back accomplished either manually (for example, by the surgeon or an assistant to the surgeon) or through a semi-automated or fully automated process (for example, a syringe pump mechanism, an actuator, motor, servo, ballscrew/leadscrew, spring, and/or the like), and/or the like. Some embodiments may utilize compressed gas (such as previously described), for example to generate a vacuum for aspiration through Venturi action. The aspiration fluid pathway may in some embodiments comprise a pressure or flow sensor to determine aspiration vacuum pressure and/or aspirated fluid flow rate. The fluid pathway and sensor may in some embodiments be separated by a filter or membrane to prevent contamination of the fluid and damage to the sensor, or non-contact measurement methods may be utilized.

In some embodiments, the tray may also incorporate a reservoir tank to hold the waste aspirated fluid and tissue. The tray may comprise a window and/or a light (e.g. LED) preferably but not necessarily the color red to minimize the impact on the surgeon's vision, to enable to the surgeon to visualize the fluid level in the reservoir tank. The reservoir tank may in some embodiments comprise a fluid level sensor to measure the level of aspirated fluid and remaining free volume. This may be utilized, for example, to alert the surgeon if the reservoir tank is near full capacity. The reservoir tank in some embodiments may be configured to expand as the volume of fluid inside increases (for example, as a balloon or bladder style reservoir, a reservoir with accordion-style collapsible walls, and/or the like).

Locating the aspiration pump and waste reservoir in or near the tray and in close proximity to the patient or within the sterile field can be preferable in some embodiments to, among other things, minimize the tubing length required, which improves the performance and responsiveness of the aspiration system. This reduces the path length of the aspirated fluid, thereby reducing the requirements of the aspiration mechanism and eliminating long tubing sets that slow the response time (for example, when the surgeon changes the rate of aspiration or switches from aspiration to reflux) and can entangle the surgeon and assistants in the operating room.

The tray may in some embodiments comprise stopcocks or other valves (manual or automated) to select between different aspiration intake sources (for example, a vitreous cutter handpiece and a soft trip extrusion handpiece).

Handpieces

In some embodiments, the tray system may comprise one or more handheld probes or handpieces that may comprise a needle (for example, 18 gauge, 20 gauge, 23 gauge, 25 gauge, 27 gauge or other size) inserted into either the anterior or posterior chamber of the eye during a surgical procedure (such as, for example, one or more of the various handpieces described herein with reference to FIGS. 1E, 4A, 5A, 6A, and 8A). Handpieces in some embodiments may comprise one or more of vitreous cutters/aspirators, endoilluminators, laser therapy/photocoagulation probes, diathermy/electrocautery/ablation probes, scissors, soft-tip extrusion probes, phacoemulsification/phacomorcellation probes, intraocular lens (IOL) inserters, forceps, mechanical probes, and/or other commonly used instruments. Some handpieces may incorporate more than one function. A handpiece may in some embodiments comprise one or more buttons and/or other user interfacing features that allow the surgeon to control the functions of that specific handpiece and/or possibly other functions as well (such as, for example, rates of infusion or aspiration).

Vitreous Cutter Handpiece

In some embodiments, a tray system comprises a vitreous cutter handpiece for removal of vitreous during a vitreoretinal procedure. The handpiece may in some embodiments be tethered to the tray via a multi-conductor cable that provides power and an optional communications interface (for example to communicate with the tray or base unit electronics, for example the status of button presses on the handpiece). In some embodiments, the cutter mechanism may be powered by a motor or motor and gear assembly inside the handpiece. In some embodiments, the cutter mechanism may be powered pneumatically by an external pneumatic source (for example, a pump, compressor, compressed gas source, and/or the like) that is connected to the handpiece via one or more flexible pneumatic tubes. The external pneumatic source may be located within the tray or the non-disposable base unit (for embodiments that incorporate a base as previously described). The cutter mechanism may in some embodiments be powered by a transmission cable or torque coil that rotates, reciprocates, or translates in one or more axes. Using the principles of electromagnetism, the cable or coil may be used to supply electrical power to the handpiece as well, for example by rotating or otherwise moving a magnet in proximity to a wire coil and generating a current that can power the electronics of the handpiece. The cable or coil may be driven by a motor, solenoid, electromagnet, linear actuator, and/or the like that is located external to the handpiece, for example in the tray or non-disposable base unit. The cable or coil connected to the handpiece may be coupled to the motor or drive actuator in the base via a shaft coupling, spline coupling, or similar to enable ease-of-setup by a surgeon or assistant in the operating room. In some embodiments, a magnetic coupling may be used to maintain a sterile field between the motor and the cable or coil. The cut speed, rate of aspiration and other functions may be controlled by buttons or other user interfaces on the handpiece itself, or through a footpedal.

Similar drive configurations may also be used for lens removal or phacomorcellation handpieces as well as other mechanically-driven instruments.

Figure 8A:
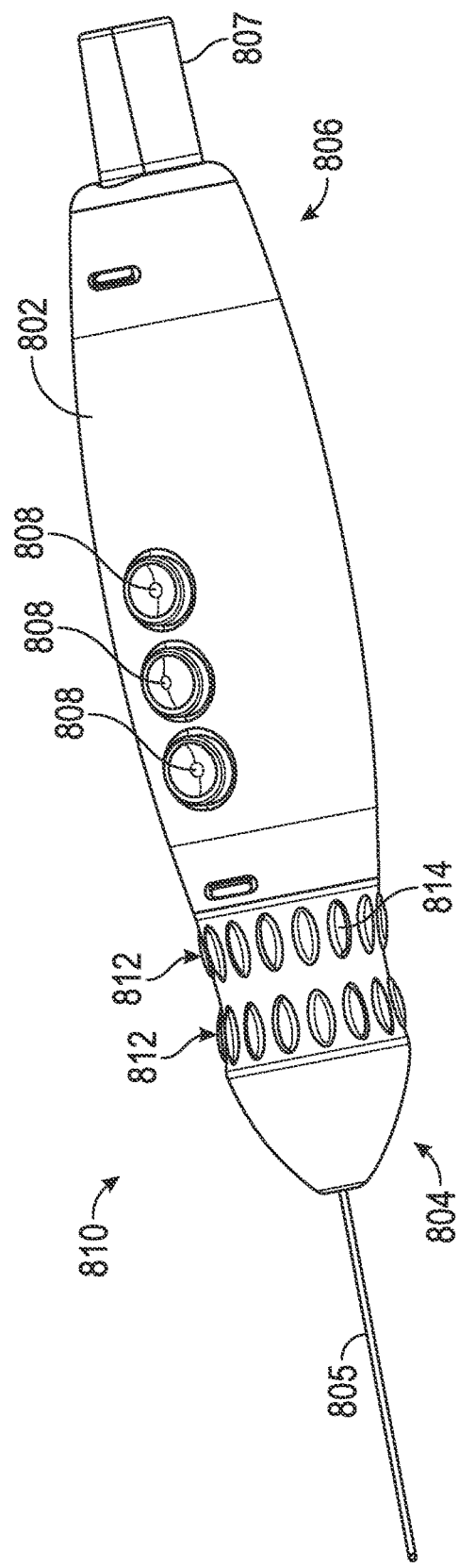
FIGS. 8A and 8B illustrate an embodiment of a handpiece having a plurality of buttons.
Figure 8B:
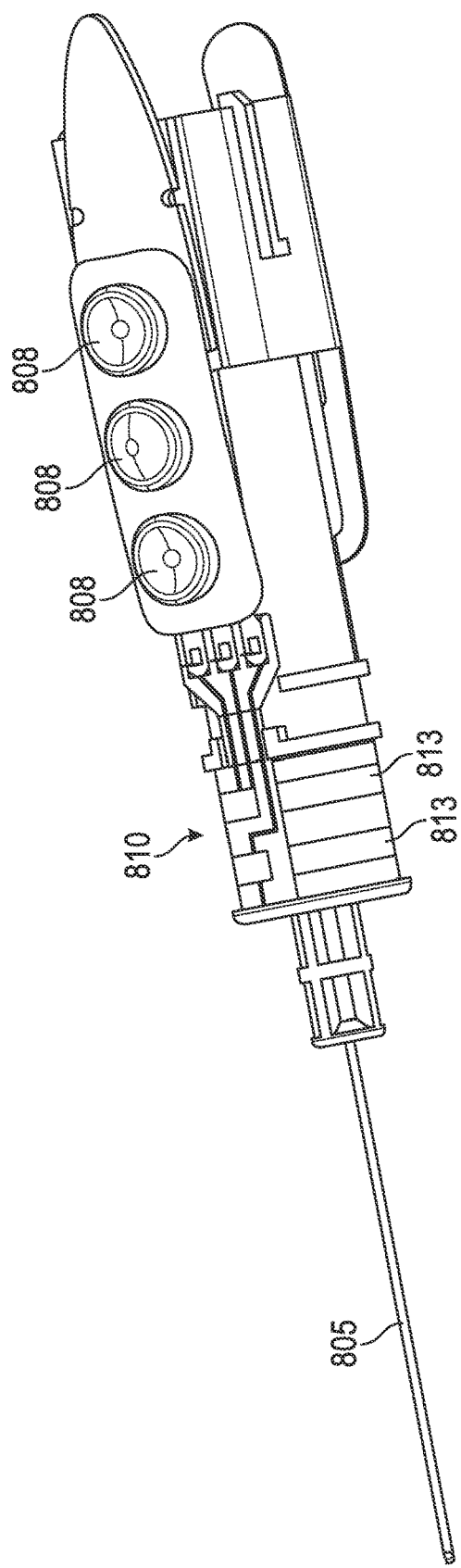

In some embodiments, a vitreous cutter handpiece may be a handpiece 810 as illustrated in FIGS. 8A and 8B, as further described below. In some embodiments, a vitreous cutter handpiece may comprise one or more features similar to as disclosed in U.S. Patent Application Publication No. 2008/0208233, entitled DISPOSABLE VITRECTOMY HANDPIECE, which is hereby incorporated by reference herein in its entirety.

Endoilluminator Handpiece

In some embodiments, a tray system may comprise an endoilluminator handpiece that provides illumination inside the eye. The handpiece may be tethered to the tray in some embodiments via a multi-conductor cable that provides power and an optional communications interface (for example to communicate with the tray or base unit electronics, for example the status of button presses on the handpiece). The endoilluminator may in some embodiments incorporate a light source (for example, white LED or RGB LED) that is coupled to a fiber or fiber bundle installed in an endoscopic needle. Alternately, the light source may be located in the tray or base unit and coupled (either permanently or using a detachable interface) to a fiber or fiber bundle that terminates in an endoscopic needle in the handpiece.

In some embodiments, an endoillumination handpiece may comprise one or more features similar to as disclosed in U.S. Pat. No. 8,172,834, entitled PORTABLE HANDHELD ILLUMINATION SYSTEM, which is hereby Incorporated by reference herein in its entirety.

Soft-Tip Extrusion Handpiece

The tray system may in some embodiments comprise a soft-tip extrusion handpiece that incorporates a soft tubing material (for example, silicone or the like) for aspirating vitreous and fluids from the retina. The handpiece may in some embodiments be tethered to the tray via a multi-conductor cable that provides power and an optional communications interface (for example, to communicate with the tray or base unit electronics, for example the status of button presses on the handpiece). The rate of aspiration and other functions may be controlled by buttons or other user interface features on the handpiece itself, or through a footpedal. The endoillumination power output and other functions (such as infusion rate) may in some embodiments be controlled by buttons or other user interface features on the handpiece itself, or through a footpedal.

Diathermy/Electrocautery Handpiece

The tray system in some embodiments may comprise a bipolar electrocautery handpiece that is capable of controlled cauterization of tissues. The handpiece in some embodiments may comprise two nested needles or tubes separated by an insulating layer (such as, for example, polyimide tubing or the like). The exposed distal end of the two needles or tubes act as electrodes for the bipolar electrocautery. The handpiece may in some embodiments be tethered to the tray via a multi-conductor cable that provides power and an optional communications interface (for example to communicate with the tray or base unit electronics, for example the status of button presses on the handpiece). The handpiece may in some embodiments have integrated electronics for generating the high voltage waveform required for electrocautery, or alternately the electrocautery circuitry may be located in the tray or base unit and supplied to the handpiece via insulated wires. The diathermy/electrocautery function and other functions may be controlled by buttons or other user interface features on the handpiece itself, and/or through a footpedal.

Laser Therapy Handpiece

The tray system in some embodiments may comprise a fiber-based laser handpiece that is capable of photocoagulation. The handpiece may in some embodiments be tethered to the tray via a multi-conductor cable that provides power and an optional communications interface (for example to communicate button presses and system status with the tray electronics). The handpiece may in some embodiments incorporate a light source, such as a laser diode, that has sufficient power for photocoagulation. The laser diode may in some embodiments be coupled to a fiber or fiber bundle that is mounted inside an endoscopic needle for insertion into the eye or other surgical site. Alternately, the light source and associated optics may in some embodiments be located in the tray or base unit with either a permanent or interchangeable optical interface to a fiber or fiber bundle that terminates in an endoscopic needle located in the handpiece. The laser therapy power output and other functions may be controlled in some embodiments by buttons or other user interface features on the handpiece itself, or through a footpedal.

Scissors

The tray system in some embodiments may comprise a powered scissors handpiece that enables the surgeon to cut tissue without requiring manual manipulation, for example using fingers to squeeze, slide, or otherwise activate the cutting mechanism of the scissors. In one embodiment, the scissors are tethered to the tray via a multi-conductor cable that provides power and an optional communications interface (for example with the tray electronics). Power to the cutting mechanism is provided in some embodiments by the tray via the tethered cable. The cutting mechanism may in some embodiments comprise a motor, solenoid, linear actuator, nitinol or shape memory alloy wire (for example, a wire that contracts when a current is passed through the wire and expands when the current ceases and the wire cools), and/or the like. Alternate embodiments may position the actuator in the tray or base, and mechanical cutting may be provided via a linkage, such as a transmission cable or torque coil that is rotated, reciprocated, or translated along one or more axes.

Handpiece Storage

In some embodiments, a tray may comprise space configured to hold the handpiece(s) when they are not in use (such as, for example, the spaces 111 illustrated in FIG. 1E), and/or may provide connectivity to the handpiece(s) via one or more of an electrical, fluidic, pneumatic, optical, and/or mechanical interface. The spaces to hold the handpieces and the top surface of the tray in general may in some embodiments comprise features to cope with undesired fluids that may be present on the tray during the procedure. For example, the tray top and handpiece areas (which may be recessed pockets or wells) may have recessed channels or holes to drain any fluids or carry any fluids away. Likewise, any recessed areas may include absorbent or sponge-like materials to absorb any unwanted fluids. The handpieces may be mounted in the tray prior to packaging and sterilization to simplify the pre-op setup procedure. The tray may in some embodiments include clips, straps, or other locking mechanisms that enable the handpieces to be secured in place, for example during shipment or movement of the tray. Additional handpieces may be packaged and sterilized separately, for example to enable replacement of a failed handpiece during a procedure without having to open an entire new tray system.

Handpiece User Interface Features

Some embodiments of handpieces comprise one or more means of acquiring user input, such as one or more buttons or switches (including, for example, membrane, tactile, pushbutton, rotary, joystick, hall sensing, capacitive touch, pressure sensitive, and/or the like) located on the handpiece, and/or inertial sensors (including gyro(s), accelerometer(s), magnetometer(s), and/or the like). These input methods can be used to control one or more functions of the handpiece and/or console, such as, for example, activating, deactivating, and controlling the probe tip motion and aspiration functions. For example, in some embodiments, the surgeon may press and hold one button to activate emulsification/morcellation, and release the button to stop emulsification/morcellation. The surgeon may press and release another separate button repeatedly to cycle through aspiration rates. The inertial sensors can be used in some embodiments for position tracking as well as user input. For example, the surgeon may orient or move the handpiece in a particular manner to perform a function; an example would be deactivating the system when the handpiece is placed upside down on a tray or table (the system would recognize the upside down orientation of the handpiece and the lack of motion/movement); a second example would be lightly tapping on the handpiece with a finger to activate or deactivate a function (the accelerometer will detect the handpiece deflection caused by the tapping); yet another example would be rotating the handpiece in a clockwise fashion to increase the rate aspiration or some other function and rotating the handpiece in a counter-clockwise fashion to decrease the rate of aspiration or some other function (where the angular motion is detected by the gyro). The user input may in some embodiments be processed or otherwise acted upon internally within the handpiece, or the input may in some embodiments be relayed to a separate console or tray via a tethered electrical connection (for example, conductive wires/cables) or wireless connection (for example, RF, inductive, or infrared) for example. The handpiece may in some embodiments comprise a microcontroller or microprocessor for registering user input, controlling the functions of the handpiece, and/or communicating with external components of the system (for example a console or tray). The handpiece may in some embodiments comprise wireless capabilities to transmit and receive information to/from a separate console, tray, display, and/or other handpieces.

Some embodiments comprise analog buttons (such as, for example, a pressure or deflection sensitive button) that provide finer control over the handpiece functions than a standard binary (on/off) or momentary switch. For example, one or more analog buttons sensitive to pressure or deflection may be used to provide fine control of functions such as, for example, cut speed, aspiration, or illumination/laser power output. In one embodiment, one or more pressure-sensitive buttons in the grip of the handpiece can be used to control rate of aspiration or cut speed; the harder the surgeon squeezes, the higher the cut speed or rate of aspiration for example. Likewise, other sensors can be incorporated that measure flexion, deflection, or translation such that the further a surgeon pushes, slides, or otherwise moves a button, the higher the rate of, for example, aspiration or cut speed. This can be achieved, for example, with button implementations that vary a parameter (such as resistance or capacitance) based on an applied input (such as pressure or deflection). For example, one button implementation may be sensitive to pressure such that the harder the surgeon squeezes, the lower (or higher) the resistance, which can be measured by the handpiece electronics (and/or remote electronics, such as electronics located in a tray or base). Another implementation utilizes a change in capacitance, such that the distance (and therefore capacitance) between two parallel conductive plates varies with the force applied to a button. Another implementation may connect different circuits depending on how far a button is depressed or moved. Yet another implementation may utilize magnetic sensors to detect the location of a magnet and/or magnetic field strength to determine how far a button has been depressed or moved. Yet another implementation utilizes capacitive touch technology to provide analog control.

FIGS. 8A and 8B illustrate an embodiment of a handpiece or surgical instrument 810 comprising a housing or body 802 having a plurality of buttons 812, 808. FIG. 8A is a perspective view of the handpiece 810, and FIG. 8B is a perspective view of the handpiece 810 with the housing or body 802 removed to enable visualization of features positioned beneath the housing 802. The handpiece 810 comprises a proximal end 806 adjacent a cable interface 807, and a distal end 804 having a surgical tool 805, such as a needle, extending therefrom. In some embodiments, the surgical tool 805 is permanently or semi-permanently installed. In some embodiments, the distal end 804 is configured to enable a surgical tool 805 to be positioned in a coupled engagement with the distal end 804.

The handpiece 810 comprises three buttons 808 positioned adjacent to an exterior surface of the housing 802. In this embodiment, the buttons 808 comprise digital, binary, or momentary buttons or switches, meaning they have two states, namely on or off, for controlling of a feature. The buttons 808 may, for example, comprise mechanical switches that selectively open and close an electrical circuit when an actuation surface of the button 808 is moved relative to the housing 802.

The handpiece 810 further comprises in this embodiment two pressure sensitive buttons 812. In other embodiments, the handpiece may comprise fewer or more pressure sensitive buttons. Each of the two pressure sensitive buttons 812 comprises a circumferential force-sensitive resistor 813 that is configured to change a resistance value based on a magnitude of pressure applied against a surface of the force sensitive resistor 813. In some embodiments, the force sensitive resistor 813 comprises a thin multilayer polyimide sheet. In some embodiments, as can be seen in FIG. 8A, the buttons 812 comprise an actuation surface extending circumferentially around the handpiece 810 and/or housing 802 that, when depressed, presses against the force sensitive resistor 813. In some embodiments, the exterior surface of the buttons 812 comprise tactile regions or features 814, illustrated in FIG. 8A as a plurality of raised bumps spaced circumferentially around the handpiece 810 and/or housing 802. Such a configuration may be advantageous to, for example, enable a user or surgeon to precisely control a feature when the handpiece 810 is in any rotational position with respect to the user's hand.

As used herein, the word "button" may be used interchangeably with other words or phrases, such as switch, selector, user input, and/or the like. One of skill in the art will recognize that a variety of user interface features, including buttons or other similar features, may be used with the techniques disclosed herein to detect a user input.

In addition to traditional on/off or momentary buttons and analog buttons that depend on some type of electrical or electromechanical contacts, additional user input solutions are feasible that eliminate the need for electronics in the handpiece and/or the need for tethered power and communication interfaces to the handpiece. Such embodiments may be advantageous to, among other things, increase manufacturability and/or reduce cost of disposable components of the system, such as, in some embodiments, the handpieces.

Optical Buttons

In some embodiments, user input can be detected using buttons that rely on principles of optics and optical fiber, instead of (or in some embodiments, in addition to) electrical or electromechanical features. For example, in some embodiments, one or more buttons may have one or more fibers, light pipes, or optical waveguides associated with it, the fibers extending from the handpiece to the tray or base unit electronics (either as a continuous fiber or one or more fiber sections optically connected together). The fiber may be coupled to a light source (such as a light source located in the tray or base unit) and may propagate light to the button location. A button may be designed to bend or otherwise flex the fiber when the button is depressed, reducing or eliminating the light propagation through the fiber and/or changing the polarization of the light through the fiber, both of which are detectable by the electronics and can be used to indicate a button press. Other embodiments instead alter or route/reroute the light path (e.g. a reflective surface on a button, the surgeon's fingertip, etc.) such that the change can be detected and identified as a button press. The principles of fiber interferometry can also be used, such that a button press sufficiently alters the fiber so that the changes to phase altering interference fringes and the location thereof can be detected and interpreted as button presses. In a similar fashion, fiber Bragg grating sensors, long-period fiber grating sensors, and similar embodiments can be integrated into the fiber(s) to measure strain, thereby detecting changes in the fiber and their location(s). Some embodiments may utilize one of the optical techniques disclosed herein, and some embodiments may utilize more than one of the optical techniques and/or may utilize one or more of the optical techniques and one or more non-optical techniques.

In some embodiments, one or more buttons each have a single continuous fiber associated with it. The fiber is routed from the electronics in the tray or base to the handpiece button and back to the tray or base (either as a continuous fiber or as two or more sections optically coupled together). When the button is pressed, the fiber is bent in such a manner as to decrease or eliminate the light propagation, change the polarization of the light in a detectable manner, or induce strain in the fiber that alters the interference fringes in a detectable manner. In other embodiments, one or more buttons each have two fibers associated with it (each either as a continuous fiber or as two or more sections optically coupled together), one that carries the light from the tray to the button and another that acts as a return for the light back to the tray. The button is designed such that when it is depressed, light is allowed to propagate from the source fiber to the return fiber. This can be accomplished, for example, with a reflective surface or a transmissive or light pipe material that is angled or positioned properly when depressed, or even using the surgeon's fingertip to redirect the light from the source fiber to the return fiber.

Another embodiment comprises a single fiber for both the source and return path of the light, since fiber can simultaneously propagate light in both directions. For example, an optical circulator can be configured to allow light to be injected into the fiber at the source (such as the tray or base unit) while simultaneously separating any reflected light along the same fiber to be detected by a photodetector or other sensor in the electronics. Such reflections could be caused by a reflective surface (or even fingertip) at the end of the fiber, or even a bend, flex, or twist of the fiber.

In another embodiment, a single fiber or optical waveguide provides the source light to each button, and each button has an additional individual return fiber to indicate button presses.

In other embodiments, instead of individual fibers for each button, a single fiber is routed from the tray or base to each button in series and back to the tray or base. Different buttons are designed to alter the polarization or light propagation different amounts, such that each button can be distinguished from each other. Alternately, the optical path distance (such as the fiber length) between each button can be adjusted such that the principles of optical time domain reflectometry or similar can be used to determine the location along the fiber of the button press, and hence which button was pressed.

FIGS. 9A-9D illustrate example embodiments of handheld medical instruments or handpieces comprising one or more optical buttons. FIG. 9A illustrates schematically a handpiece comprising a housing or enclosure 802 having two optical fibers 906 passing therethrough. In this embodiment, an actuating member 904, when placed close to tips or ends 907 of the optical fibers 906 is configured to reflect light from one optical fiber 906 to another optical fiber 906, the reflection of which may be detected by hardware, for example, in a surgical tray or console. In some embodiments, the actuating member 904 is a portion of a physical button that is configured to reflect light. In some embodiments, the actuating member 904 is a user's finger, in some embodiments a gloved finger.

In some embodiments, the two separate optical fibers 906 may also be implemented as, for example, a single fiber with two or more waveguides, for example the source light would propagate down the core and the return light down one or more claddings of the fiber, or vice versa. Also note that a single source fiber may in some embodiments supply light to multiple buttons, with each button paired with an independent return fiber or independent waveguide, for example, multiple claddings, in a custom-designed return fiber. Alternatively, each button may have a separate source fiber providing light modulated at a different frequency for each button, with a common shared return fiber, with the modulated signal allowing the processing hardware to distinguish between different signals.

In some embodiments, a technique for enabling multiple buttons incorporates a filter or attenuator that attenuates the light propagation through each button differently (for example, 100%, 50%, 25%, and/or the like) or filters the wavelength (assuming a broadband light source) through one or more or each button so that the remaining wavelengths or the power attenuation could be measured by the processing hardware, such as, for example, in the surgical tray or console. In some embodiments, the wavelength of the light may be broadband (for example, white light or multi-wavelength light) or it may be single wavelength (for example infrared) and may be modulated to minimize interference issues with other ambient sources of light.

FIG. 9B illustrates another embodiment of a surgical handpiece comprising an optical button. The embodiment illustrated in FIG. 9B comprises an optical fiber 906 terminating at an end or tip 907. An actuating member 904 may have light reflective properties such that, when the actuating member 904 is positioned adjacent the tip 907, light is reflected back into the fiber 906, which can then be detected by, for example, tray or console hardware. Sensitivity in some embodiments can be adjusted to require contact by the actuating member 904 with the tip 907 and/or handpiece enclosure 802, or just a proximity to the tip 907 and/or handpiece enclosure 802.

FIG. 9C depicts another embodiment of an optical button. The embodiment illustrated in FIG. 9C comprises two optical fibers 906 and an actuating member 904 which, when moved relative to the enclosure 802 and/or fibers 906, moves a reflective member 908. When the reflective member 908 is positioned in front of tips or ends 907 of the optical fibers 906, light is reflected from one optical fiber 906 to the other optical fiber 906, enabling detection of the button press by processing hardware located at, for example, the surgical tray or console.

FIG. 9D depicts another embodiment of an optical button, wherein a deflectable member or portion 910 connected to or part of one or more optical fibers 906 is positioned to be deformed when an actuating member 904 is moved relative to the handpiece enclosure 802. For example, when the actuating member 904 contacts and/or presses against the deflectable member 910, the deflectable member 910 may bend or otherwise deformed in a manner that may be detectable by processing hardware, such as processing hardware located in or as a part of the surgical tray or console. In this embodiment, if the button is depressed, the actuating member 904 will bend the deflectable member 910. If the deflectable member or portion 910 is deflected sufficiently, the propagation of light through the fiber will be significantly decreased or eliminated, which can be detected by the processing hardware and interpreted as a button press. In an alternate embodiment, more light instead of less light is allowed to propagate the harder or further the button is pressed.

In some embodiments, the optical button configuration illustrated in FIG. 9D can also be configured to provide linear or pressure sensitive feedback through one or more of several techniques. First, the decrease in light throughput will correlate to how much deflection or bending the fiber is experiencing. The amount of light detected can be used to determine the overall position of the button. So, for example, the harder or further the user pushes the button, the greater the measured change in light throughput. Similarly, the bending of the fiber will change the polarization of the light through the fiber. This can also be detected by processing hardware and used to determine the magnitude of deflection. More advanced optical theory can also be used. For example, the fiber button can be one arm of a fiber-based interferometer (michelson, common path, mach zehnder, and/or the like) such that the change in optical path length and the phase changes induced in the fiber due to stress or bending can be detected in the processing hardware and measured to determine how hard or far the button was depressed. Another technique is to include gratings in the fiber during manufacturing to produce a strain sensor, such as a Fiber Bragg Grating Sensor or long-period fiber grating, that can be used to provide linear or pressure sensitive button functionality due to the correlated change in wavelength resulting from strain on the fiber (for example, caused by pressing or bending the fiber). These grating sensors can also be used for multiple buttons with only a single fiber by designing a grating along the fiber with different properties for each button such that the properties of each grating are distinguishable from each other by the processing hardware.

Yet another embodiment can use a single fiber for multiple linear or pressure sensitive buttons by detecting where along the fiber a strain or bend was induced, and correlating this to the position of the one or more buttons. This detection can be implemented using principles of time domain reflectometry, wherein the time for a light pulse to propagate through the fiber and reflect back to the source is measured and the distance determined, with the reflection caused by the button inducing a strain or impedance in the fiber. This is more difficult over a shorter fiber length and would benefit in some embodiments from the addition of fiber between the buttons to increase an optical path length between buttons.

In some embodiments, an optical button configuration may comprise one or more optical waveguides in addition to or in lieu of one or more optical fibers, such as a plastic light pipe or the like. Further, in various embodiments disclosed herein that refer to optical fibers, it should be understood that those optical fibers may be a continuous optical fiber and/or may comprise one or more sections coupled together, and or may comprise one or more optical waveguides in series with a fiber.

In some embodiments, an optical button is configured to enable, disable, or attenuate the propagation of light from a source waveguide (or fiber) to a return waveguide (or fiber), for example, with a reflective or absorptive surface, including a finger, to enable detection of a button press.

In some embodiments, an optical button uses a single fiber or waveguide in a loop configuration and alters a property of light in a detectable fashion, for example, by bending the fiber or waveguide. This property can be the power or magnitude (for example, attenuating or increasing the light throughput), the polarization of the light, the wavelength of the light (for example, by filtering out some wavelengths of a broadband light source and detecting the remaining wavelengths; or by shifting or filtering the wavelength for example through a grating design), the optical path length or phase of the light (for example, by bending or straining the fiber which can be detected in an interferometer setup). A related embodiment relies on the principles of total internal reflection and "evanescent waves." For example, by touching the outer surface of the fiber (stripped of any outer protective coating, if present), the refractive indices at the fiber interface are changed (for example, fiber to finger instead of fiber to air) which can alter the propagation of light through the fiber. This change may be detectable with sufficiently sensitive amplification and processing equipment.

In some embodiments, an optical button uses one fiber for multiple buttons, for example by using custom fibers with multiple waveguides (and possibly modulating the signal to or from different buttons); by filtering out different wavelengths depending on which button is pressed (for example, using multi-wavelength or broadband light); by attenuating the light by different amounts depending on which button is pressed; by using different fiber grating parameters for each button; by measuring the time for reflected pulses to propagate (time domain reflectometry) where the reflection is caused by a deformation or strain in the fiber caused by the activation of a button.

Pneumatic/Hydraulic Buttons

In some embodiments, buttons that utilize pneumatic and/or hydraulic principles are incorporated into the handpiece, which can in some embodiments (similarly to as with the optical button embodiments) eliminate the need for any electronics or electrical interfacing between the handpiece and the tray or base unit.

In some embodiments, one or more buttons of the handpiece may be attached to or fluidly coupled with a flexible pneumatic tube (for example, flexible silicone, vinyl or PVC tubing or the like) that is connected to the tray or base unit electronics (either using a continuous section of tubing or two or more sections in fluid communication). The electronics may comprise, for example, a pressure sensor that can measure the pressure inside the tube. This can be used to determine whether or not a button is pressed. For example, a depressed button may seal or pinch the tube that is otherwise open, unobstructed, or patent, in such a way that is detectable by the pressure sensor. Similarly, in some embodiments, the tubing may terminate in the handpiece such that the surgeon may cover the hole in the end of the tubing (such as with his or her finger) to indicate a button press. A bladder or balloon, for example at the end of the tubing, may be included such that when the bladder or balloon is depressed or otherwise modified (such as by an external force, for example, from a finger or from a movable component of the handpiece), the change in internal air/fluid pressure can be detected and interpreted as a button press. In some embodiments, instead of relying on ambient pressure, the tubing may be fluidly connected to an air or vacuum source such that the measured pressure will be different depending on whether or not the tubing is patent or sealed. In this embodiment, each button would have its own independent tubing. In another embodiment, multiple buttons can share a single tube, for example if each button restricted the flow through the tube to a different magnitude, such that each button would be distinguishable from the rest. For example, the first button may restrict the tubing completely, while the second button restricts the inner lumen of the tubing 75%, the third button 50%, the fourth button 25%, and so on, which may be distinguishable by a fluidly-coupled sensor.

FIGS. 10A-10C illustrate example embodiments of handpieces comprising pneumatic or hydraulic buttons. FIG. 10A illustrates schematically an example wherein an actuating member 904, such as a finger or a portion of a button, deforms a deformable member 1002 fluidly connected with tubing 1004 to enable detection of a change in pressure in the deformable member 1002 and/or the tubing 1004. In some embodiments, a flexible tube (e.g. vinyl or silicone tubing) 1004 with a balloon or bladder 1002 attached to the end of the tube that has some gas or fluid within it (e.g. air)

can be used as a linear button. The harder the balloon or bladder 1002 is squeezed, pushed, or compressed, the higher the pressure inside the tube, which can be measured and processed by a pressure sensor and processing electronics located, for example, in the remote console or tray.

In some embodiments, the balloon or bladder 1002 may be directly pressed by the user's finger, or a button, lever, or other feature activated by the user's finger(s) or grip may apply the force to the balloon or bladder.

In some embodiments, the balloon or bladder 1002 does not have to be a separate component but can be integrated into the tubing 1004 itself. The tubing 1004 can be designed to have a ballooned area (for example, a segment with a larger diameter). A similar result can also be achieved (for example, the change in pressure can be detected and interpreted as a button press) by squeezing or compressing a tube that is simply sealed on the end. The advantage of a balloon or bladder with a larger diameter than the rest of the tubing is that the squeeze or compressive force will be amplified and therefore easier to measure by the pressure sensor and processing electronics and less susceptible to noise or interference.

In some embodiments, multiple buttons can be included in the handpiece by repeating the design of FIG. 10A; however it is also possible to incorporate multiple buttons using a single flexible tube with multiple balloons or bladders. Each balloon or bladder could, for example, in one embodiment, have a different diameter/volume, such that when pressed the processing hardware could determine which button was pressed (for example, which balloon was compressed) based on the amplitude of the signal. This permutation may be desirable to use with, for example, on/off or momentary buttons as opposed to linear buttons, although it could also be used with pressure-sensitive or linear buttons.

FIG. 10B illustrates another embodiment of a pneumatic or hydraulic button wherein a flexible tube 1004 (for example, vinyl or silicone tubing) that is open (for example unsealed) on the button end 1006 can be used to detect button presses. If the user presses their finger (or an another actuating surface) on the open end 1006 of the tube 1004, a pressure sensor and sensitive electronics that amplify and process the pressure signal can detect the changes in pressure and register a button press (for example, momentary or on/off).

FIG. 10C illustrates another embodiment of a pneumatic or hydraulic button wherein a flexible tube 1004 (for example, vinyl or silicone) can provide pressure sensitive, linear, or digital (for example, on/off or momentary) functionality. The tube 1004 is routed from the console or tray to the handpiece and back to the console or tray. There is an air source pumping air into one end of the tube and a pressure or flow sensor on the other end of the tube. When the user's finger (or another actuation surface) 904 presses against the tube (or against a button, lever, or similar, for example comprising opposing members 1008, 1010) the tube is constricted. The more the user squeezes, the more the tube is constricted, potentially to the point that no air can flow. Alternately, instead of squeezing the tube, the tube may be bent, which would likewise cause a reduction in air flow due to the collapsing wall of the pliable tubing. This change in air flow can be detected by the sensor and correlated to the amount of compression or deflection of the tube, thereby providing a linear style button output.

Embodiments of this and other designs can even use the pneumatic source that is often used to drive certain instruments such as aspirators and vitreous cutters.

Piezo Buttons

In some embodiments, buttons comprising piezo material (for example piezoelectric quartz or the like) provide user input functionality. Piezo crystals when bent, flexed, or otherwise deflected generate a voltage spike that can be used as an input mechanism. For example, a mechanical button designed to deflect a piezo material will generate a voltage when the button is pressed. If the piezo material is coupled via electrical wires to electronics in the tray or base unit (or in some embodiments in the handpiece), this voltage spike can be detected and interpreted as a button press. While the handpiece is tethered to the tray or base unit electronics with electrical wires in this embodiment, there are no active electronics required in the handpiece itself in this embodiment and it is not necessary to supply power to the handpiece via any wires or cables. Multiple buttons can be incorporated into the handpiece, each completing a separate circuit (for example, two independent wires per button or one independent wire and one shared ground wire); alternately, multiple buttons can share a single circuit or pair of wires to the tray or base unit by designing each piezo element to generate a different range of voltages such that each piezo element is distinguishable from the others based on the magnitude of the voltage generated when the button is pressed.

FIG. 11 illustrates an embodiment of a handpiece having a piezoelectric button comprising electrical wires 1102 coupled to piezoelectric material, such as a piezo crystal 1104 to detect deformation of the crystal via a voltage differential measured across the wires 1102. In some embodiments, the crystal 1104 is configured to be deformed by one or more of the actuating members 904, 904'.

In some embodiments, the piezo button incorporates one or more piezo crystals or elements that are connected electrically to the tray or console. No power is applied to the piezo crystal through the wires; instead the piezo element will produce a voltage when it is bent or deflected which can be detected by the tray or console electronics. The amplitude of the voltage that is generated is proportional to the amount of deflection of the piezo element—so the further the piezo is deflected, the higher the voltage spike. This property can be used to provide a pressure sensitive or linear-style output.

To incorporate multiple buttons without simply repeating the design for each button, multiple piezo elements can in some embodiments share a single set of wires if, for example, each piezo element is designed to provide a different voltage at a given deflection, such that the different voltage ranges are distinguishable from each other and can be correlated to a particular button. Alternately, each button can be designed to deflect its respective piezo element (assuming all piezo elements have approximately the same specifications) a different amount, thereby producing a different voltage amplitude range depending on which button is pressed.

In any of the illustrative embodiments disclosed in FIGS. 9A-11, the buttons can be binary on/off switches, or variable switches that produce responses or outputs that are linear, non-linear, or a combination of linear and non-linear with respect to the input received by the button.

Power Sources

Embodiments disclosed herein may employ one or more of a variety of power sources to perform the intended functions, including but not limited to actuation of the probe tip and aspiration as well as receiving and/or processing user input. The handpiece may in some embodiments be tethered to a console or tray that provides power (for example DC or AC voltage or current) via electrical wires. The handpiece may in some embodiments be powered by a rechargeable (secondary) internal battery (such as lithium ion/lithium polymer, NiMH, NiCd, or other chemistry), a non-rechargeable (primary) internal battery (such as alkaline, lithium manganese, or other chemistry), and/or an internal capacitor of sufficient capacity (such as a "super-capacitor" or "ultra-capacitor"). The handpiece can be in some embodiments powered wirelessly via a wireless power coupling system. For example, the handpiece may incorporate a "secondary" coil that can be inductively powered from a "primary" coil that is strategically located in proximity to the handpiece and driven by a power amplifier. For example, the primary coil can be mounted on the microscope and used to power a handpiece containing a secondary coil and positioned by the surgeon underneath the microscope during the surgical procedure. This inductive link (or a different inductive link) can also in some embodiments be used for bi-directional communication between the handpiece and the tray or console. The handpiece may also in some embodiments be powered pneumatically or hydraulically (tethered with tubing set to console or tray, for example) to provide emulsification and aspiration. The handpiece may in some embodiments be powered by a moving, reciprocating, or rotating cable transmission or torque transmission coil. The handpiece may in some embodiments be powered via a wound-up spring. The handpiece may in some embodiment comprise a turbine or other means of converting the cable, pneumatic or hydraulic power to electricity for powering, for example, internal microcontroller(s), sensor(s), actuator(s), and/or button(s). The handpiece may in some embodiments be powered by converting a squeezing, gripping, rotating, or sliding motion made by the surgeon on the handpiece grip into a useful motion (for example reciprocating or rotary motion to activate the probe tip). The handpiece may in some embodiments be powered by compressed air, for example a canister or cartridge inserted into the handpiece, or an external source. Additional power sources may be used to provide the desired functionality, and in some embodiments more than one power source may be used to power a handpiece (for example, an AC voltage driving a piezoelectric crystal mounted in a phaco handpiece for phacoemulsification and pneumatic power to provide the aspiration of the phaco handpiece).

Pressure-Sensitive Handpiece Tip

Some embodiments incorporate a pressure sensor in a distal tip of the handpiece to provide intra-ocular pressure readings from the anterior chamber or posterior chamber. The pressure sensor readings (and/or information derived from the pressure sensor readings) can be visually displayed (for example, on a stand-alone display, heads-up display, in-microscope display, or a display integrated into the tray or console) and/or audibly announced. In some embodiments, alarms and/or safety measures may be activated based on the pressure sensor readings. Furthermore the pressure sensor readings may be used in some embodiments in a feedback control loop to control the rate of infusion and/or aspiration during anterior segment or posterior segment procedures. The pressure sensor may in some embodiments be of the MEMS variety. The pressure sensor may in some embodiments be a fiber-based design. In some embodiments, the pressure sensor is incorporated into a separate component (for example, instead of distal tip of the handpiece) that is also inserted into or located adjacent to the anterior chamber or posterior chamber of the eye. For example, the pressure sensor may be incorporated into an infusion cannula or chandelier light source and the pressure measurements used to control the rate of infusion. Other embodiments may be configured to rely on external IOP measurements taken through established measurement techniques and processed by the handpiece or tray electronics.

Illumination

In some embodiments, the tray may comprise one or more light sources for providing illumination at the surgical site. Endoscope-based illuminators (endoilluminators) and other illumination devices, such as chandelier illuminators, can be coupled to the light source(s) via a single fiber or bundle of multiple fibers. The fiber(s) may in some embodiments have large numerical apertures to maximize coupling efficiency. The fiber(s) may in some embodiments be butt-coupled to the LED source or interfaced through a lensing system. The endoilluminator and chandelier illuminator, and/or the like can be permanently coupled to the light source via the fiber(s) or they may be coupled via an optical connector configuration that efficiently couples light from the light source into the fiber and allows the fiber of the handpiece to be attached and detached from the light source at will or on demand by the surgeon. The tray may in some embodiments comprise high brightness phosphor-based white LED(s) and/or RGB LED(s). More than one source may be provided to simultaneously accommodate, for example, one handpiece endoilluminator and one chandelier illumination device through an optical coupling; alternately, a single light source can be shared among two or more illumination components, for example through a free-space or fiber splitter. The constituent colors of the RGB LED(s) may in some embodiments be adjusted individually to provide improved visualization under different conditions, for example in the presence of a dye, stain, or indicator. Other embodiments comprise a xenon, mercury vapor, halogen, and/or other light source located in the tray and optical coupled to the handpiece via fiber. Alternate embodiments include a light source (for example, LED or laser) in the handpiece itself; the light source may be coupled (butt-coupled or otherwise) to a needle containing a light pipe, fiber, or fiber bundle that propagates the light to the distal tip of the endoilluminator probe. The fiber or fiber bundle may in some embodiments have a large numerical aperture to maximize coupling efficiency between the LED and the fiber. Alternately, the LED may be located at the distal tip of the needle, preferably sealed from the external environment (for example, behind a transparent window at the distal tip of the needle or potted in epoxy).

Laser Therapy

In some embodiments, the tray may comprise one or more laser sources for providing photocoagulation, ablation, cutting, and/or other laser therapy at the surgical site. For example, a laser therapy probe handpiece may comprise a fiber or fiber bundle mounted in an endoscopic needle inserted into the eye. The fiber probe may be configured to focus or collimate the therapeutic laser for use during surgery. The laser therapy probe can in some embodiments be permanently coupled to the light source via the fiber(s) or they may in some embodiments be coupled via a removable optical connector that couples light from the light source into the fiber. Alternate embodiments include a laser source in the handpiece itself; the laser source may be coupled (butt-coupled or otherwise) to a needle containing a light pipe, fiber, or fiber bundle that propagates the light to the distal tip of the laser therapy probe.

Display

In some embodiments, the tray may comprise one or more display(s) (for example, indicator(s), interface(s), LCD(s), and/or LED(s)) for displaying system information. The tray may also include audio feedback. The display(s) may also be located separate from the tray. Display(s) may be mounted in a heads-up configuration (for example, on the microscope) or projected into the optical path of the microscope for display within the visual field of the microscope. Display(s) may in some embodiments be located on or above the tray in the left and/or right periphery of the surgeon to enable viewing without turning the head. Display(s) may in some embodiments be located on the tray directly in front of the surgeon and viewable when looking downwards and provided with a shade or cover that prevents light pollution from the display from entering the microscope's objective lens or affecting the surgeon's vision. Alternately the display(s) may have a film, window, or other transparent cover that is polarized or contains lenticular grooves, parallax barriers, or other features that enable viewing from limited perspectives or are transparent from only a certain angle to prevent light pollution.

Audio Feedback

In some embodiments, the tray may comprise audio capabilities to provide feedback to the surgeon. The audio feedback may comprise in some embodiments a variety of tones with different frequencies, amplitudes, durations, and/or the like. The audio feedback may in some embodiments comprise voice prompts that are capable of providing more useful and thorough feedback information to the surgeon. The voice prompts may be digitized audio recordings/samples or synthesized speech, and the voice prompts may be stored in non-volatile memory (for example, flash memory or a hard drive). The tray electronics may in some embodiments comprise a microcontroller or microprocessor that controls the voice prompts (and/or tones, and/or other audio feedback), activating the proper audio feedback based on input from the surgeon, a handpiece's hardware or software, the tray's hardware/software, and/or the like.

Foot Pedal

In some embodiments, the tray may comprise or be connected to one or more foot pedals (tethered or wireless) that enable control of the handpiece and/or tray functions (including, for example, infusion and aspiration rates, cutter speed, illumination power, and/or the like).

Storage

In some embodiments, the tray may comprise one or more areas (for example, holes, cavities, containers, voids, pockets, hooks, fasteners, magnets, and/or the like) configured to hold, store, or secure items used during the surgical procedure, including, for example, the handpieces, sutures, syringes/needles, trocars, and/or other instruments or supplies. The tray may also in some embodiments comprise an integrated sharps container to safely secure or dispose of sharps. The tray may in some embodiments comprise a magnet or magnetic surface to hold needles, sharps, and other metal items/instruments in place.

Example Disposable Tray Embodiments

In one preferred embodiment, a tray system comprises a disposable tray that comprises disposable electronics and disposable pumps (for infusion and/or aspiration). The tray system also comprises disposable handpieces with electronics and functional components integrated into one or more of the handpieces (for example, motor for vitreous cutter, LED for illumination, and/or the like). In some embodiments, the entire tray system is intended to be disposed of after a single use or limited number of uses.

In a second preferred embodiment, a tray system comprises a disposable tray with disposable pumps but with little or no active electronics. The electronics are integrated into a reusable base that interfaces with the disposable tray and handpieces. The handpieces may comprise integrated electronics and functional components.

In a third preferred embodiment, the tray itself comprises only disposable fluidic components. The reusable base unit incorporates the electronics and pump drivers (for example, motors) while the disposable pump heads or a portion thereof are located in the disposable tray. The handpieces may include integrated electronics and functional components.

In a related preferred embodiment, the tray itself comprises only disposable fluidic components. The reusable base unit incorporates the electronics and pump drivers (for example, motors) while the disposable pump heads or a portion thereof are located in the disposable tray. Other functional components are also incorporated into the base instead of the handpieces. These include: a mechanical source for the cutter and similar instruments, which may be a pneumatic or hydraulic source or a motor source to drive a transmission cable or torque coil; a light source for endoillumination; a laser source for photocoagulation. In some cases, the handpieces have no integrated electronics and rely on fiber-based, pneumatic, piezo, or similar non-electronic methods of acquiring user input. Alternately the handpieces may not incorporate any buttons and all control is done via a footpedal or buttons on the tray or reusable base unit.

Anterior Chamber Surgical System

In an embodiment, the surgical systems illustrated herein can be configured for anterior chamber surgical procedures, for example lens or cataract removal (commonly known as phacoemulsification or phacomorcellation). The surgical system can include one or more of the following: a handpiece, a console, a surgical tray, a display, a foot pedal.

Handpiece

In an embodiment, the system includes a handpiece held by the surgeon, the distal end of which is inserted into the anterior chamber of the eye through a small incision. The distal tip of the handpiece can be inserted into the eye and can be, for example, a hypodermic needle, tube, cannula, or trocar of size 17, 18, 19, 20, 21, 22, 23, 24, 25, 26, or 27 gauge, or in some cases larger or smaller gauge and made of any of a variety of materials, including stainless steel, titanium, plastic, polyimide, or the like.

In an embodiment, one function of the distal tip that is inserted into the eye is to break up, emulsify, and/or morcellate the cataract or lens, through ultrasonic vibrations, mechanical cutting and/or agitation, ablation, laser, and/or other techniques. In an embodiment, the system can include a hollow channel inside the probe tip for the aspiration or infusion of fluids and tissues. In an embodiment, the system can include a separate hollow channel for infusion and aspiration that is located adjacent to or positioned near the probe tip that breaks up the cataract or lens.

In an embodiment, the system can include mechanisms for vibrating, oscillating, reciprocating, rotating, cantilevering, and/or otherwise translating the position of the needle in one or more axes, for example, at a frequency in the kilohertz or higher range. This motion can be generated through the use of piezoelectric materials (such as Lead-Zirconate-Titanate, aka PZT or a commonly available piezo bender element) that vibrate when driven by a time varying voltage signal; it can be generated through the use of electromagnetics, for example in a voice-coil actuator, solenoid, or motor configuration; it can be generated through pneumatics or hydraulics; it can be generated through transmission drive systems, such as a rotating or reciprocating cable, drive belt, geared transmission, or push-pull mechanism.

In an embodiment, the system can comprise mechanisms for mechanically cutting or agitating a tissue sample (e.g. lens, cataract). This can include a guillotine or rotating (360 degrees or a portion thereof, for example 180 degrees reciprocating) cutting mechanism such as those used for vitreous removal or tissue debridement. Other mechanisms can include a rotating or otherwise moving/translating a whisk or whisks at the distal end of the probe that break up the tissue of interest through the mechanical movement of the whisk.

In an embodiment, the system can be configured to utilize a monochromatic or narrow-band light source (for example, laser or LED or the like) or a broadband light source to prepare the cataract, lens, or other tissue of interest for removal via photochemical, photomechanical, and/or photothermal means. The light source may be located in the handpiece itself or located elsewhere (for example, in the console or tray) and optically routed to the handpiece via a single mode or multi-mode fiber or fiber bundle (as previously described).

In an embodiment, the system can be configured to utilize heat or RF energy to cauterize or ablate tissue of interest (including but not limited to cataracts and lens material).

In an embodiment, a second function of the distal tip of the handpiece that is inserted into the eye can be to aspirate tissue and fluid, including the lens and cataract fragments generated by the action of the probe tip. The probe tip can be connected to a pump system that creates vacuum pressure at the needle tip to aspirate fragments smaller than the inner diameter of the needle tip and to hold fragments larger than the inner diameter until they are emulsified, morcellated, or broken up by the action of the needle tip to a size small enough for aspiration. The aspiration can be provided by a pump or other means as described earlier. In an embodiment, the locate the aspiration mechanism (pump or otherwise) can be in a console or tray separate from the handpiece and tethered to the handpiece via tubing suitable for the aspiration of fluids, for example, flexible vinyl or PVC tubing. The close proximity of the tray reduces the length requirements of the tubing set, improving the performance and responsiveness of the aspiration. In an embodiment, the locate the aspiration mechanism (pump or otherwise) can be inside the handpiece or adjacent to the handpiece. This can be advantageous because such a design reduces the path length of the aspirated fluid, thereby reducing the requirements of the aspiration mechanism and eliminating long tubing sets that slow the response time (for example, when the surgeon changes the rate of aspiration) and can entangle the surgeon and assistants in the operating room.

Embodiments of the invention incorporate a pressure sensor in the distal tip of the handpiece as previously described, wherein the pressure sensor readings are used to control the rate of infusion (and/or aspiration) during a procedure. The control can be in the form of a feedback control loop (e.g. proportional-integral-derivative aka PID, a subset thereof, or similar). A simpler embodiment displays the pressure information to the surgeon, who can then manually control the rate of infusion. The system can alert the surgeon when the pressure falls outside of a preset range of pressures.

In an embodiment, the system can be configured to include some or all of the required functionality for anterior segment procedures, and in particular lens and cataract removal, in a single handpiece. The handpiece can include a mechanism for emulsification or morcellation (using one or more of the mechanisms previously described above). The handpiece can also comprise a mechanism for aspiration (such as a pump or one or more of the mechanisms previously described). The handpiece may include a mechanism for providing infusion into the eye (including any of the means previously described), or the infusion may be provided by a separate infusion cannula and infusion fluid source and controlled/driven by the handpiece or a separate nearby tray or console.

In the self-contained embodiments, the handpiece can include a reservoir that contains the infusion solution(s) (including BSS, viscoelastics, silicone oil, or the like) used during the procedure. The handpiece can also include a reservoir for the aspirated waste. The infusion and aspiration reservoirs can be contained within or fully integrated into the handpiece or they may be located directly adjacent to it (for example, a bag or bottle hanging from the handpiece or secured to the surgeon's hand, wrist, or arm). The reservoirs can also be located in, mounted on, or hanging from a nearby tray, surgeon arm support or patient headrest, or from the microscope.

In an embodiment, the system can be configured to use of a filter (for example, a porous membrane filter) in-line with the aspiration and infusions systems so that the aspirated fluid can be filtered and re-infused, significantly reducing the amount of required infusion solution and decreasing the size and weight requirements of a handheld system. The filter (and aspiration pump) can be located in the handpiece, or in some embodiments one or both may be located in a separate nearby tray or console with a short tubing set connecting the handpiece to the filter and/or pump. The filtered system can also be used for posterior segment and vitreo-retinal procedures.

In an embodiment, the self-contained handpiece can comprise the integrated pressure sensor previously described above, either in the distal tip of the needle or along the fluid path, utilized in a feedback control loop to control the rate of infusion (and/or aspiration).

In an embodiment, the system can be configured to be used with valved cannula(s) and/or valved trocar(s) to reduce leakage of infused fluid from the anterior chamber. These devices are commonly used in vitreoretinal surgery and orthopedic surgery but not typically in anterior segment procedures. However, incorporating them into the anterior procedure will reduce the required volume of infusion fluids, resulting in a smaller, lighter, and more compact system.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above.

What is claimed is:

1. A handheld medical instrument for surgical procedures, the handheld medical instrument comprising:
   a body having an exterior surface shaped to be held and manipulated by a human hand;
   a surgical tool extending from a distal end of the body;
   an aspiration pump inside the body;
   an inertial sensor configured to track a rotational motion of the body, the surgical tool being configured to control a variable of a function based on the rotational motion of the body, such that the variable is one of increased or decreased with detected clockwise rotational motion and is correspondingly decreased or increased with detected counterclockwise motion;
   wherein the variable is aspiration rate and wherein the aspiration rate of the aspiration pump is controlled using the tracked rotational motion of the body; and
   a pressure-sensitive button for controlling operation of the surgical tool, the pressure-sensitive button comprising:
      an actuation surface positioned adjacent the exterior surface of the body; and
      a pressure detection device, the pressure detection device configured to enable output of a signal for controlling a function of the surgical tool, the signal being proportional to a position of the actuation surface.

2. The handheld medical instrument of claim 1, wherein the pressure detection device comprises a force sensitive resistor that changes a resistance based on the position of the actuation surface.

3. The handheld medical instrument of claim 2, wherein the actuation surface extends circumferentially around an exterior of the body and is positioned at least partially around a conductive surface of the force sensitive resistor.

4. The handheld medical instrument of claim 1, wherein the pressure detection device comprises an optical fiber positioned such that movement of the actuation surface with respect to the body causes the optical fiber to deform.

5. The handheld medical instrument of claim 1, wherein the pressure detection device comprises an optical fiber and an optical detection member, wherein movement of the actuation surface with respect to the body causes the optical detection member to move in a way that affects a light signal of the optical fiber.

6. The handheld medical instrument of claim 1, wherein the pressure detection device comprises a deformable member coupled to the actuation surface such that movement of the actuation surface with respect to the body deforms the deformable member, causing a change in pressure within the deformable member.

7. The handheld medical instrument of claim 1, wherein the pressure detection device comprises a piezoelectric material coupled to the actuation surface such that movement of the actuation surface with respect to the body causes deformation of the piezoelectric material.

8. The handheld medical instrument of claim 1, wherein the surgical tool comprises at least one of: an endoillumination device, a laser therapy device, a lens removal device, a trabecular meshwork removal device, and a vitreous cutting device.

9. The handheld medical instrument of claim 1, wherein the variable of the function of the surgical tool further comprises at least one of: a speed and an intensity.

10. The handheld medical instrument of claim 1, wherein the proportionality of the signal in relation to the position of the actuation surface is linear.

11. The handheld medical instrument of claim 1, wherein the actuation surface is movable between a fully outward position and a fully depressed position, wherein the actuation surface is biased outward, such that the actuation surface remains in the fully outward position until an external force is applied that overcomes a biasing force.

12. The handheld medical instrument of claim 1, wherein the signal is configured to control simultaneously the function of the surgical tool and at least one other surgical function.

13. The handheld medical instrument of claim 1, further comprising a second pressure-sensitive button comprising a second actuation surface and second pressure detection device configured to enable controlling of a second surgical function.

14. The handheld medical instrument of claim 1, further comprising a tether coupled to a surgical tray.

15. The handheld medical instrument of claim 1, wherein the pressure detection device is configured to transmit the signal to a processor external to the medical instrument for interpretation of the signal for controlling of the function of the surgical tool.

16. The handheld medical instrument of claim 1, wherein the signal controls the function of the surgical tool without the signal being transmitted to a processor external to the medical instrument for interpretation.

17. The medical instrument of claim 1, wherein the body comprises at least one of the following: an elongate cylindrical shape and an elongate rounded shape.

18. The handheld medical instrument of claim 1, wherein the pressure detection device comprises a thin multilayer polyimide sheet.

19. The handheld medical instrument of claim 1, wherein controlling the variable of the function comprises increasing an aspiration rate of the surgical tool when the body is rotated and decreasing an aspiration rate of the surgical tool when the body is rotated.

* * * * *